United States Patent
Weeber

(10) Patent No.: US 11,022,815 B2
(45) Date of Patent: *Jun. 1, 2021

(54) MULTI-RING LENS, SYSTEMS AND METHODS FOR EXTENDED DEPTH OF FOCUS

(71) Applicant: AMO GRONINGEN B.V., Groningen (NL)

(72) Inventor: Hendrik A. Weeber, Groningen (NL)

(73) Assignee: AMO Groningen B.V., Groningen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/252,157

(22) Filed: Jan. 18, 2019

(65) Prior Publication Data

US 2019/0171036 A1 Jun. 6, 2019

Related U.S. Application Data

(60) Continuation of application No. 15/149,574, filed on May 9, 2016, now Pat. No. 10,197,815, which is a
(Continued)

(51) Int. Cl.
*G02C 7/02* (2006.01)
*G02C 7/04* (2006.01)
(Continued)

(52) U.S. Cl.
CPC ............ *G02C 7/041* (2013.01); *A61B 3/0025* (2013.01); *A61F 2/1602* (2013.01); *A61F 2/164* (2015.04);
(Continued)

(58) Field of Classification Search
CPC .. G02C 7/06; G02C 2202/20; G02C 2202/22; G02C 7/041; G02C 7/027; G02C 7/022;
(Continued)

(56) References Cited

U.S. PATENT DOCUMENTS 3,367,734 A 2/1968 Karl et al.
3,722,986 A 3/1973 Tagnon
(Continued)

FOREIGN PATENT DOCUMENTS

AU 2005230194 B2 12/2010
CA 2501217 A1 4/2004
(Continued)

OTHER PUBLICATIONS

Schwiegerling et al., "Representation of videokeratoscopic height data with Zernike polynomials," Journal of the Optical Society of America, 1995, 12 (10), 2105-2113.
(Continued)

*Primary Examiner* — Jordan M Schwartz
(74) *Attorney, Agent, or Firm* — Johnson & Johnson Surgical Vision, Inc.

(57) ABSTRACT

Systems and methods for providing enhanced image quality across a wide and extended range of foci encompass vision treatment techniques and ophthalmic lenses such as contact lenses and intraocular lenses (IOLs). Exemplary IOL optics can include an aspheric refractive profile imposed on a first or second lens surface, and a diffractive profile imposed on a first or second lens surface. The aspheric refractive profile can focus light toward a far focus. The diffractive profile can include a central zone that distributes a first percentage of light toward a far focus and a second percentage of light toward an intermediate focus. The diffractive profile can also include a peripheral zone, surrounding the central zone, which distributes a third percentage of light toward the far focus and a fourth percentage of light toward the intermediate focus.

25 Claims, 25 Drawing Sheets

Related U.S. Application Data division of application No. 14/014,701, filed on Aug. 30, 2013, now Pat. No. 9,335,563.

(60) Provisional application No. 61/695,806, filed on Aug. 31, 2012.

(51) Int. Cl.
  *G02C 7/06* (2006.01)
  *A61F 2/16* (2006.01)
  *G02B 27/00* (2006.01)
  *A61B 3/00* (2006.01)
  *A61F 2/14* (2006.01)

(52) U.S. Cl.
  CPC .......... *A61F 2/1613* (2013.01); *A61F 2/1618* (2013.01); *A61F 2/1637* (2013.01); *A61F 2/1654* (2013.01); *G02B 27/0075* (2013.01); *G02C 7/022* (2013.01); *G02C 7/024* (2013.01); *G02C 7/027* (2013.01); *G02C 7/044* (2013.01); *G02C 7/06* (2013.01); *A61F 2/1451* (2015.04); *A61F 2240/002* (2013.01); *G02C 2202/20* (2013.01); *G02C 2202/22* (2013.01)

(58) Field of Classification Search
  CPC ....... G02C 7/024; G02C 7/044; A61F 2/1613; A61F 2/1654; A61F 2/1637; A61F 2/164; A61F 2/1618; A61F 2/1602
  See application file for complete search history.

(56) References Cited

U.S. PATENT DOCUMENTS

| | | |
|---|---|---|
| 4,210,391 A | 7/1980 | Cohen et al. |
| 4,340,283 A | 7/1982 | Cohen et al. |
| 4,460,275 A | 7/1984 | Spriggs |
| 4,504,892 A | 3/1985 | Zulfilar |
| 4,504,982 A | 3/1985 | Burk |
| 4,580,883 A | 4/1986 | Shinohara |
| 4,606,626 A | 8/1986 | Shinohara |
| 4,637,697 A | 1/1987 | Freeman |
| 4,640,593 A | 2/1987 | Shinohara |
| 4,641,934 A | 2/1987 | Freeman |
| 4,642,112 A | 2/1987 | Freeman |
| 4,655,565 A | 4/1987 | Freeman |
| 4,710,193 A | 12/1987 | Volk |
| 4,762,408 A | 8/1988 | Shinohara |
| 4,778,462 A | 10/1988 | Grendahl |
| 4,795,462 A | 1/1989 | Grendahl |
| 4,798,608 A | 1/1989 | Grendahl |
| 4,798,609 A | 1/1989 | Grendahl |
| 4,856,234 A | 8/1989 | Goins |
| 4,856,889 A | 8/1989 | Guilino et al. |
| 4,881,804 A | 11/1989 | Cohen |
| 4,881,805 A | 11/1989 | Cohen |
| 4,898,461 A | 2/1990 | Portney |
| 4,932,970 A | 6/1990 | Portney |
| 4,936,666 A | 6/1990 | Futhey |
| 4,957,506 A | 9/1990 | Mercier |
| 4,978,211 A | 12/1990 | Cornu et al. |
| 4,995,714 A | 2/1991 | Cohen |
| 4,995,715 A | 2/1991 | Cohen |
| 5,016,977 A | 5/1991 | Baude et al. |
| 5,017,000 A | 5/1991 | Cohen |
| 5,019,098 A | 5/1991 | Mercier |
| 5,050,981 A | 9/1991 | Roffman |
| 5,054,905 A | 10/1991 | Cohen |
| 5,056,908 A | 10/1991 | Cohen |
| 5,061,058 A | 10/1991 | Guilino et al. |
| 5,066,301 A | 11/1991 | Wiley |
| 5,076,684 A | 12/1991 | Simpson et al. |
| 5,089,023 A | 2/1992 | Swanson |
| 5,089,024 A | 2/1992 | Christie et al. |
| 5,096,285 A | 3/1992 | Silberman |
| 5,100,226 A | 3/1992 | Freeman |
| 5,104,212 A | 4/1992 | Taboury et al. |
| 5,112,351 A | 5/1992 | Christie et al. |
| 5,114,220 A | 5/1992 | Baude et al. |
| 5,116,111 A | 5/1992 | Simpson et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,129,718 A | 7/1992 | Futhey et al. |
| 5,144,483 A | 9/1992 | Cohen |
| 5,148,205 A | 9/1992 | Guilino et al. |
| 5,161,057 A | 11/1992 | Johnson |
| 5,173,723 A | 12/1992 | Volk et al. |
| 5,178,636 A | 1/1993 | Silberman |
| 5,191,366 A | 3/1993 | Kashiwagi |
| 5,220,359 A | 6/1993 | Roffman |
| 5,225,858 A | 7/1993 | Portney |
| 5,229,797 A | 7/1993 | Futhey et al. |
| 5,236,970 A | 8/1993 | Christ et al. |
| 5,257,132 A | 10/1993 | Ceglio et al. |
| 5,260,727 A | 11/1993 | Oksman et al. |
| 5,322,649 A | 6/1994 | Rheinish et al. |
| 5,344,447 A | 9/1994 | Swanson |
| 5,349,394 A | 9/1994 | Freeman et al. |
| 5,349,471 A | 9/1994 | Morris et al. |
| 5,381,190 A | 1/1995 | Rehse et al. |
| 5,384,606 A | 1/1995 | Koch et al. |
| 5,408,281 A | 4/1995 | Zhang |
| 5,443,506 A | 8/1995 | Garabet |
| 5,443,507 A | 8/1995 | Jacobi |
| 5,444,106 A | 8/1995 | Zhou et al. |
| 5,446,508 A | 8/1995 | Kitchen |
| 5,448,312 A | 9/1995 | Roffman et al. |
| 5,485,228 A | 1/1996 | Roffman et al. |
| 5,581,405 A | 12/1996 | Meyers et al. |
| 5,589,982 A | 12/1996 | Faklis et al. |
| 5,629,800 A | 5/1997 | Hamblen |
| 5,652,638 A | 7/1997 | Roffman et al. |
| 5,674,284 A | 10/1997 | Chang et al. |
| 5,682,223 A | 10/1997 | Menezes et al. |
| 5,683,457 A | 11/1997 | Gupta et al. |
| 5,684,560 A | 11/1997 | Roffman et al. |
| 5,684,595 A | 11/1997 | Kato et al. |
| 5,699,142 A | 12/1997 | Lee et al. |
| 5,715,031 A | 2/1998 | Roffman et al. |
| 5,715,091 A | 2/1998 | Meyers |
| 5,724,258 A | 3/1998 | Roffman |
| 5,728,156 A | 3/1998 | Gupta et al. |
| 5,748,282 A | 5/1998 | Freeman |
| 5,760,871 A | 6/1998 | Kosoburd et al. |
| 5,777,719 A | 7/1998 | Williams et al. |
| 5,796,462 A | 8/1998 | Roffman et al. |
| 5,800,532 A | 9/1998 | Lieberman |
| 5,805,260 A | 9/1998 | Roffman et al. |
| 5,822,091 A | 10/1998 | Baker |
| 5,838,496 A | 11/1998 | Maruyama et al. |
| 5,847,802 A | 12/1998 | Menezes et al. |
| 5,888,122 A | 3/1999 | Gupta et al. |
| 5,895,422 A | 4/1999 | Hauber |
| 5,895,610 A | 4/1999 | Chang et al. |
| 5,929,969 A | 7/1999 | Roffman |
| 5,968,094 A | 10/1999 | Werblin et al. |
| 5,968,095 A | 10/1999 | Norrby |
| 5,982,543 A | 11/1999 | Fiala |
| 6,007,747 A | 12/1999 | Blake et al. |
| 6,019,472 A | 2/2000 | Koester et al. |
| 6,050,687 A | 4/2000 | Bille et al. |
| 6,070,980 A | 6/2000 | Obara et al. |
| 6,082,856 A | 7/2000 | Dunn et al. |
| 6,086,204 A | 7/2000 | Magnante |
| 6,089,711 A | 7/2000 | Blankenbecler et al. |
| 6,095,651 A | 8/2000 | Williams et al. |
| 6,120,148 A | 9/2000 | Fiala et al. |
| 6,126,283 A | 10/2000 | Wen et al. |
| 6,126,286 A | 10/2000 | Portney |
| 6,139,145 A | 10/2000 | Israel |
| 6,142,625 A | 11/2000 | Sawano et al. |

(56) References Cited

U.S. PATENT DOCUMENTS

| | | |
|---|---|---|
| 6,145,987 A | 11/2000 | Baude et al. |
| 6,154,323 A | 11/2000 | Kamo |
| 6,199,986 B1 | 3/2001 | Williams et al. |
| 6,210,005 B1 | 4/2001 | Portney |
| 6,215,096 B1 | 4/2001 | Von Wallfeld et al. |
| 6,224,211 B1 | 5/2001 | Gordon |
| 6,231,603 B1 | 5/2001 | Lang et al. |
| 6,270,220 B1 | 8/2001 | Keren |
| 6,271,915 B1 | 8/2001 | Frey et al. |
| 6,325,510 B1 | 12/2001 | Golub et al. |
| 6,338,559 B1 | 1/2002 | Williams et al. |
| 6,353,503 B1 | 3/2002 | Spitzer et al. |
| 6,413,276 B1 | 7/2002 | Werblin |
| 6,429,972 B1 | 8/2002 | Ota et al. |
| 6,439,720 B1 | 8/2002 | Graves et al. |
| 6,457,826 B1 | 10/2002 | Lett |
| 6,462,874 B1 | 10/2002 | Soskind |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,497,483 B2 | 12/2002 | Frey et al. |
| 6,511,180 B2 | 1/2003 | Guirao et al. |
| 6,520,638 B1 | 2/2003 | Roffman et al. |
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,391 B2 | 4/2003 | Ross, III et al. |
| 6,547,822 B1 | 4/2003 | Lang |
| 6,554,425 B1 | 4/2003 | Roffman et al. |
| 6,554,859 B1 | 4/2003 | Lang et al. |
| 6,557,992 B1 | 5/2003 | Dwyer et al. |
| 6,576,012 B2 | 6/2003 | Lang |
| 6,582,076 B1 | 6/2003 | Roffman et al. |
| 6,585,375 B2 | 7/2003 | Donitzky et al. |
| 6,609,673 B1 | 8/2003 | Johnson |
| 6,609,793 B2 | 8/2003 | Norrby et al. |
| 6,616,275 B1 | 9/2003 | Dick et al. |
| 6,655,802 B2 | 12/2003 | Zimmermann et al. |
| 6,685,315 B1 | 2/2004 | De Carle |
| 6,705,729 B2 | 3/2004 | Piers et al. |
| 6,709,103 B1 | 3/2004 | Roffman et al. |
| 6,755,524 B2 | 6/2004 | Rubinstein et al. |
| 6,791,754 B2 | 9/2004 | Ogawa |
| 6,802,605 B2 | 10/2004 | Cox et al. |
| 6,808,262 B2 | 10/2004 | Chapoy et al. |
| 6,818,158 B2 | 11/2004 | Pham et al. |
| 6,827,444 B2 | 12/2004 | Williams et al. |
| 6,830,332 B2 | 12/2004 | Piers et al. |
| 6,835,204 B1 | 12/2004 | Stork et al. |
| 6,846,326 B2 | 1/2005 | Zadno-Azizi et al. |
| 6,848,790 B1 | 2/2005 | Dick et al. |
| 6,851,803 B2 | 2/2005 | Wooley et al. |
| 6,884,261 B2 | 4/2005 | Zadno-Azizi et al. |
| 6,923,539 B2 | 8/2005 | Simpson et al. |
| 6,923,540 B2 | 8/2005 | Ye et al. |
| 6,951,391 B2 | 10/2005 | Morris et al. |
| 6,957,891 B2 | 10/2005 | Fiala |
| 6,972,032 B2 | 12/2005 | Aharoni et al. |
| 6,986,578 B2 | 1/2006 | Jones |
| 7,025,456 B2 | 4/2006 | Morris et al. |
| 7,036,931 B2 | 5/2006 | Lindacher et al. |
| 7,048,759 B2 | 5/2006 | Bogaert et al. |
| 7,048,760 B2 | 5/2006 | Cumming |
| 7,061,693 B2 | 6/2006 | Zalevsky |
| 7,073,906 B1 | 7/2006 | Portney |
| 7,093,938 B2 | 8/2006 | Morris et al. |
| 7,111,938 B2 | 9/2006 | Andino et al. |
| 7,137,702 B2 | 11/2006 | Piers et al. |
| 7,156,516 B2 | 1/2007 | Morris et al. |
| 7,159,983 B2 | 1/2007 | Menezes et al. |
| 7,188,949 B2 | 3/2007 | Bandhauer et al. |
| 7,198,640 B2 | 4/2007 | Nguyen |
| 7,217,375 B2 | 5/2007 | Lai |
| 7,221,513 B2 | 5/2007 | Cho et al. |
| 7,232,218 B2 | 6/2007 | Morris et al. |
| 7,287,852 B2 | 10/2007 | Fiala |
| 7,293,873 B2 | 11/2007 | Dai et al. |
| 7,365,917 B2 | 4/2008 | Zalevsky |
| 7,377,640 B2 | 5/2008 | Piers et al. |
| 7,377,641 B2 | 5/2008 | Piers et al. |
| 7,441,894 B2 | 10/2008 | Zhang et al. |
| 7,455,404 B2 | 11/2008 | Bandhauer et al. |
| 7,475,986 B2 | 1/2009 | Dai et al. |
| 7,481,532 B2 | 1/2009 | Hong et al. |
| 7,543,937 B2 | 6/2009 | Piers et al. |
| 7,572,007 B2 | 8/2009 | Simpson |
| 7,604,350 B2 | 10/2009 | Dursteler Lopez et al. |
| 7,615,073 B2 | 11/2009 | Deacon et al. |
| 7,654,667 B2 | 2/2010 | Blum et al. |
| 7,670,371 B2 | 3/2010 | Piers et al. |
| 7,677,725 B2 | 3/2010 | Piers et al. |
| 7,717,558 B2 | 5/2010 | Hong et al. |
| 7,753,521 B2 | 7/2010 | Wooley et al. |
| 7,871,162 B2 | 1/2011 | Weeber |
| 7,883,207 B2 | 2/2011 | Iyer et al. |
| 7,896,916 B2 | 3/2011 | Piers et al. |
| 7,922,326 B2 | 4/2011 | Bandhauer et al. |
| 7,984,990 B2 | 7/2011 | Bandhauer et al. |
| 7,998,198 B2 | 8/2011 | Angelopoulos et al. |
| 8,128,222 B2 | 3/2012 | Portney |
| 8,157,374 B2 | 4/2012 | Bandhauer et al. |
| 8,192,022 B2 | 6/2012 | Zalevsky |
| 8,197,063 B2 | 6/2012 | Iyer et al. |
| 8,216,307 B2 | 7/2012 | Schaper, Jr. |
| 8,231,219 B2 | 7/2012 | Weeber |
| 8,231,673 B2 | 7/2012 | Sacharoff et al. |
| 8,235,525 B2 | 8/2012 | Lesage et al. |
| 8,240,850 B2 | 8/2012 | Apter et al. |
| 8,241,354 B2 | 8/2012 | Hong et al. |
| 8,262,728 B2 | 9/2012 | Zhang et al. |
| 8,292,953 B2 | 10/2012 | Weeber et al. |
| 8,382,281 B2 | 2/2013 | Weeber |
| 8,388,137 B2 | 3/2013 | Dreher et al. |
| 8,430,508 B2 | 4/2013 | Weeber |
| 8,444,267 B2 | 5/2013 | Weeber et al. |
| 8,480,228 B2 | 7/2013 | Weeber |
| 8,500,805 B2 | 8/2013 | Kobayashi et al. |
| 8,506,075 B2 | 8/2013 | Bandhauer et al. |
| 8,529,623 B2 | 9/2013 | Piers et al. |
| 8,556,416 B2 | 10/2013 | Lawu |
| 8,556,417 B2 | 10/2013 | Das et al. |
| 8,573,775 B2 | 11/2013 | Weeber |
| 8,619,362 B2 | 12/2013 | Portney |
| 8,636,796 B2 | 1/2014 | Houbrechts et al. |
| 8,652,205 B2 | 2/2014 | Hong et al. |
| 8,678,583 B2 | 3/2014 | Cohen |
| 8,709,079 B2 | 4/2014 | Zhang et al. |
| 8,734,511 B2 | 5/2014 | Weeber et al. |
| 8,740,978 B2 | 6/2014 | Weeber et al. |
| 8,747,466 B2 | 6/2014 | Weeber et al. |
| 8,755,117 B2 | 6/2014 | Kobayashi et al. |
| 8,771,348 B2 | 7/2014 | Zhao |
| 8,827,446 B2 | 9/2014 | Iyer et al. |
| 8,906,089 B2 | 12/2014 | Piers et al. |
| 9,069,185 B2 | 6/2015 | Zhao |
| 9,078,745 B2 | 7/2015 | Zhang et al. |
| 9,122,074 B2 | 9/2015 | Piers et al. |
| 9,164,201 B2 | 10/2015 | Fermigier et al. |
| 9,223,148 B2 | 12/2015 | Fiala et al. |
| 9,304,329 B2 | 4/2016 | Zhao |
| 9,310,624 B2 | 4/2016 | Argal et al. |
| 9,320,594 B2 | 4/2016 | Schwiegerling |
| 9,329,309 B2 | 5/2016 | Van Heugten |
| 9,335,563 B2 | 5/2016 | Weeber |
| 9,335,564 B2 | 5/2016 | Choi et al. |
| 9,370,416 B2 | 6/2016 | Argal et al. |
| 9,518,864 B2 | 12/2016 | Grossinger et al. |
| 9,563,070 B2 | 2/2017 | Ando et al. |
| 9,622,856 B2 | 4/2017 | Weeber et al. |
| 9,869,580 B2 | 1/2018 | Grossinger et al. |
| 9,925,041 B2 | 3/2018 | Gerlach et al. |
| 2001/0018612 A1 | 8/2001 | Carson et al. |

(56) References Cited

U.S. PATENT DOCUMENTS

| | | |
|---|---|---|
| 2002/0082690 A1 | 6/2002 | Sarbadhikari |
| 2002/0093701 A1 | 7/2002 | Zhang et al. |
| 2002/0105617 A1 | 8/2002 | Norrby et al. |
| 2002/0118337 A1 | 8/2002 | Perrott et al. |
| 2002/0122153 A1 | 9/2002 | Piers et al. |
| 2003/0014107 A1 | 1/2003 | Reynard |
| 2003/0063254 A1 | 4/2003 | Piers et al. |
| 2003/0076478 A1 | 4/2003 | Cox |
| 2003/0169491 A1 | 9/2003 | Bender et al. |
| 2003/0171808 A1 | 9/2003 | Phillips |
| 2004/0021824 A1 | 2/2004 | Ye et al. |
| 2004/0080710 A1 | 4/2004 | Wooley et al. |
| 2004/0085515 A1 | 5/2004 | Roffman et al. |
| 2004/0088050 A1 | 5/2004 | Norrby et al. |
| 2004/0106992 A1 | 6/2004 | Lang et al. |
| 2004/0111153 A1 | 6/2004 | Woods et al. |
| 2004/0138746 A1 | 7/2004 | Aharoni et al. |
| 2004/0150789 A1 | 8/2004 | Jones |
| 2004/0156014 A1 | 8/2004 | Piers et al. |
| 2004/0169820 A1 | 9/2004 | Dai et al. |
| 2004/0189981 A1 | 9/2004 | Ross et al. |
| 2004/0230299 A1 | 11/2004 | Simpson et al. |
| 2004/0246440 A1 | 12/2004 | Andino et al. |
| 2004/0252274 A1 | 12/2004 | Morris et al. |
| 2005/0057720 A1 | 3/2005 | Morris et al. |
| 2005/0096226 A1 | 5/2005 | Stock et al. |
| 2005/0099589 A1 | 5/2005 | Ishak |
| 2005/0128432 A1 | 6/2005 | Altmann |
| 2005/0203619 A1 | 9/2005 | Altmann |
| 2005/0259222 A1 | 11/2005 | Kelch et al. |
| 2005/0264757 A1 | 12/2005 | Morris et al. |
| 2005/0267575 A1 | 12/2005 | Nguyen et al. |
| 2006/0004446 A1 | 1/2006 | Aharoni et al. |
| 2006/0009816 A1 | 1/2006 | Fang et al. |
| 2006/0030938 A1 | 2/2006 | Altmann |
| 2006/0034003 A1 | 2/2006 | Zalevsky |
| 2006/0055883 A1 | 3/2006 | Morris et al. |
| 2006/0066808 A1 | 3/2006 | Blum et al. |
| 2006/0098162 A1* | 5/2006 | Bandhauer ............ A61F 2/1618 351/159.44 |
| 2006/0098163 A1* | 5/2006 | Bandhauer ............ A61F 2/1613 351/159.41 |
| 2006/0109421 A1 | 5/2006 | Ye et al. |
| 2006/0116763 A1 | 6/2006 | Simpson |
| 2006/0116764 A1 | 6/2006 | Simpson |
| 2006/0139570 A1 | 6/2006 | Blum et al. |
| 2006/0176572 A1 | 8/2006 | Fiala |
| 2006/0238702 A1 | 10/2006 | Glick et al. |
| 2006/0244904 A1 | 11/2006 | Hong et al. |
| 2006/0244905 A1 | 11/2006 | Piers et al. |
| 2007/0002444 A1 | 1/2007 | Piers et al. |
| 2007/0052920 A1 | 3/2007 | Stewart et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0236769 A1 | 10/2007 | Zalevsky |
| 2007/0258143 A1 | 11/2007 | Portney |
| 2007/0268451 A1 | 11/2007 | Raghuprasad |
| 2007/0282438 A1 | 12/2007 | Hong et al. |
| 2008/0030677 A1* | 2/2008 | Simpson ............... A61F 2/1654 351/159.44 |
| 2008/0147185 A1 | 6/2008 | Hong et al. |
| 2008/0161913 A1 | 7/2008 | Brady et al. |
| 2008/0161914 A1 | 7/2008 | Brady et al. |
| 2008/0269891 A1 | 10/2008 | Hong et al. |
| 2008/0273169 A1 | 11/2008 | Blum et al. |
| 2008/0300679 A1 | 12/2008 | Altmann |
| 2009/0062911 A1 | 3/2009 | Bogaert |
| 2009/0088840 A1 | 4/2009 | Simpson et al. |
| 2009/0164008 A1 | 6/2009 | Hong et al. |
| 2009/0187242 A1 | 7/2009 | Weeber et al. |
| 2009/0210054 A1 | 8/2009 | Weeber et al. |
| 2009/0234448 A1 | 9/2009 | Weeber et al. |
| 2009/0240328 A1 | 9/2009 | Treushnikov et al. |
| 2009/0268155 A1 | 10/2009 | Weeber |
| 2009/0295295 A1 | 12/2009 | Shannon et al. |
| 2009/0323020 A1 | 12/2009 | Zhao et al. |
| 2010/0014049 A1 | 1/2010 | Bandhauer et al. |
| 2010/0016961 A1 | 1/2010 | Hong et al. |
| 2010/0057202 A1 | 3/2010 | Bogaert |
| 2010/0066973 A1 | 3/2010 | Portney |
| 2010/0087921 A1 | 4/2010 | Simpson |
| 2010/0097569 A1 | 4/2010 | Weeber et al. |
| 2010/0100177 A1 | 4/2010 | Zhao |
| 2010/0100178 A1 | 4/2010 | Weeber et al. |
| 2010/0131060 A1 | 5/2010 | Simpson et al. |
| 2010/0161048 A1 | 6/2010 | Schaper, Jr. |
| 2010/0161051 A1 | 6/2010 | Hong |
| 2010/0274233 A1 | 10/2010 | Dick et al. |
| 2010/0281021 A1 | 11/2010 | Weeber et al. |
| 2010/0312336 A1 | 12/2010 | Hong et al. |
| 2010/0312337 A1 | 12/2010 | Zhang et al. |
| 2010/0321635 A1 | 12/2010 | Apter et al. |
| 2011/0022170 A1 | 1/2011 | Simpson et al. |
| 2011/0098811 A1 | 4/2011 | Hong et al. |
| 2011/0109874 A1 | 5/2011 | Piers et al. |
| 2011/0125261 A1 | 5/2011 | Portney |
| 2011/0149236 A1 | 6/2011 | Weeber |
| 2011/0166652 A1 | 7/2011 | Bogaert et al. |
| 2011/0267693 A1 | 11/2011 | Kobayashi et al. |
| 2011/0270596 A1 | 11/2011 | Weeber |
| 2011/0292335 A1* | 12/2011 | Schwiegerling ...... A61F 2/1618 351/159.44 |
| 2011/0313522 A1 | 12/2011 | Hayes |
| 2011/0313523 A1 | 12/2011 | Hayes |
| 2011/0313525 A1 | 12/2011 | Cumming |
| 2011/0317124 A1 | 12/2011 | Weeber et al. |
| 2011/0317126 A1 | 12/2011 | Weeber |
| 2012/0029630 A1 | 2/2012 | Piers et al. |
| 2012/0059464 A1 | 3/2012 | Zhao |
| 2012/0140166 A1 | 6/2012 | Zhao |
| 2012/0143326 A1 | 6/2012 | Canovas Vidal et al. |
| 2012/0154740 A1 | 6/2012 | Bradley et al. |
| 2012/0165932 A1 | 6/2012 | Argal |
| 2012/0170121 A1 | 7/2012 | Okada et al. |
| 2012/0283825 A1 | 11/2012 | Houbrechts et al. |
| 2012/0320335 A1 | 12/2012 | Weeber et al. |
| 2012/0323321 A1 | 12/2012 | Simonov et al. |
| 2013/0035760 A1 | 2/2013 | Portney |
| 2013/0046381 A1 | 2/2013 | Zalevsky et al. |
| 2013/0060330 A1 | 3/2013 | Weeber et al. |
| 2013/0090730 A1 | 4/2013 | Weeber et al. |
| 2013/0107202 A1 | 5/2013 | Liang |
| 2013/0201445 A1 | 8/2013 | Das et al. |
| 2015/0022775 A1 | 1/2015 | Ando et al. |
| 2015/0029460 A1 | 1/2015 | Bradley et al. |
| 2015/0094807 A1 | 4/2015 | Piers et al. |
| 2015/0359625 A1 | 12/2015 | Argal et al. |
| 2016/0216535 A1 | 7/2016 | Zhao et al. |
| 2016/0220350 A1 | 8/2016 | Gerlach |
| 2016/0220352 A1 | 8/2016 | Choi et al. |
| 2016/0320633 A1 | 11/2016 | Weeber et al. |
| 2016/0334640 A1 | 11/2016 | De Juan, Jr. et al. |
| 2016/0341978 A1 | 11/2016 | Schwiegerling |
| 2017/0172088 A1 | 6/2017 | May |
| 2017/0209259 A1 | 7/2017 | Choi et al. |
| 2017/0216020 A1 | 8/2017 | Weeber et al. |
| 2017/0219846 A1 | 8/2017 | Ando |
| 2017/0227789 A1 | 8/2017 | Ando et al. |
| 2017/0239038 A1 | 8/2017 | Choi et al. |
| 2017/0245985 A1 | 8/2017 | Canovas Vidal et al. |
| 2017/0245986 A1 | 8/2017 | Canovas Vidal et al. |
| 2017/0245987 A1 | 8/2017 | Canovas Vidal et al. |
| 2017/0252151 A1 | 9/2017 | Mackool |
| 2018/0092739 A1 | 4/2018 | Pagnoulle et al. |
| 2018/0132996 A1 | 5/2018 | Tiwari et al. |
| 2018/0147050 A1 | 5/2018 | Choi et al. |
| 2018/0147052 A1 | 5/2018 | Hong et al. |
| 2018/0373060 A1 | 12/2018 | Knox et al. |
| 2019/0224000 A1 | 7/2019 | Choi et al. |
| 2019/0254810 A1 | 8/2019 | Tiwari et al. |
| 2019/0307557 A1 | 10/2019 | De Carvalho et al. |

(56) References Cited

U.S. PATENT DOCUMENTS

2019/0314148 A1 10/2019 Liu
2020/0038172 A1 2/2020 Hussain et al.

FOREIGN PATENT DOCUMENTS

| | | |
|---|---|---|
| CA | 2507659 A1 | 6/2004 |
| CA | 2590085 A1 | 6/2006 |
| CN | 1951340 A | 4/2007 |
| CN | 101181171 B | 4/2011 |
| CN | 102665611 A | 9/2012 |
| DE | 69715830 T2 | 8/2003 |
| EP | 335731 A2 | 10/1989 |
| EP | 342895 A2 | 11/1989 |
| EP | 0343067 A1 | 11/1989 |
| EP | 355230 A2 | 2/1990 |
| EP | 0369561 A2 | 5/1990 |
| EP | 375291 A2 | 6/1990 |
| EP | 412751 A2 | 2/1991 |
| EP | 0457553 A2 | 11/1991 |
| EP | 470811 A2 | 2/1992 |
| EP | 0537643 A1 | 4/1993 |
| EP | 605841 A1 | 7/1994 |
| EP | 0316162 B1 | 10/1995 |
| EP | 355230 B1 | 10/1995 |
| EP | 681198 A1 | 11/1995 |
| EP | 0537643 B1 | 3/1997 |
| EP | 0926531 A1 | 6/1999 |
| EP | 949529 A2 | 10/1999 |
| EP | 1376203 A2 | 1/2004 |
| EP | 1424049 A1 | 6/2004 |
| EP | 1862148 A1 | 12/2007 |
| EP | 1310267 B1 | 1/2008 |
| EP | 1891912 A1 | 2/2008 |
| EP | 2043558 A2 | 4/2009 |
| EP | 2045648 A1 | 4/2009 |
| EP | 1402308 B1 | 5/2009 |
| EP | 1424049 B1 | 6/2009 |
| EP | 2103279 A1 | 9/2009 |
| EP | 2113226 A1 | 11/2009 |
| EP | 2365379 A1 | 9/2011 |
| EP | 2377493 A1 | 10/2011 |
| EP | 2378319 A1 | 10/2011 |
| EP | 2290411 B1 | 5/2012 |
| EP | 2363097 B1 | 9/2012 |
| EP | 2527908 A1 | 11/2012 |
| EP | 2812882 A1 | 12/2014 |
| EP | 2813881 A1 | 12/2014 |
| EP | 2349093 B1 | 10/2015 |
| EP | 3150170 B1 | 12/2017 |
| IT | 1215851 B | 2/1990 |
| JP | 1154119 A | 6/1989 |
| JP | 2028615 A | 1/1990 |
| JP | 2079815 A | 3/1990 |
| JP | 2137814 A | 5/1990 |
| JP | 2249631 A | 10/1990 |
| JP | 3011315 A2 | 1/1991 |
| JP | 2000511299 A | 8/2000 |
| JP | 2003532157 A | 10/2003 |
| JP | 2010158315 A | 7/2010 |
| JP | 2013101323 A | 5/2013 |
| KR | 101154066 B1 | 6/2012 |
| RU | 2011154235 A | 7/2013 |
| RU | 2011154238 A | 7/2013 |
| WO | 9002963 A1 | 3/1990 |
| WO | 9222264 A1 | 12/1992 |
| WO | 9303409 A1 | 2/1993 |
| WO | 9413225 A1 | 6/1994 |
| WO | 9417435 A1 | 8/1994 |
| WO | 9724639 A1 | 7/1997 |
| WO | 9744689 A1 | 11/1997 |
| WO | 9831299 A2 | 7/1998 |
| WO | 9907309 A1 | 2/1999 |
| WO | 9923526 A1 | 5/1999 |
| WO | 0019906 A1 | 4/2000 |
| WO | 0076426 A2 | 12/2000 |
| WO | 0121061 A1 | 3/2001 |
| WO | 0163344 A1 | 8/2001 |
| WO | 0182839 A1 | 11/2001 |
| WO | 0189424 A1 | 11/2001 |
| WO | 0221194 A2 | 3/2002 |
| WO | 0234158 A2 | 5/2002 |
| WO | 02084381 A2 | 10/2002 |
| WO | 02088830 A1 | 11/2002 |
| WO | 03009053 A1 | 1/2003 |
| WO | 2004013680 A1 | 2/2004 |
| WO | 2004034129 A1 | 4/2004 |
| WO | 2004049979 A1 | 6/2004 |
| WO | 2004090611 A2 | 10/2004 |
| WO | 2004096014 A2 | 11/2004 |
| WO | 2004113959 A2 | 12/2004 |
| WO | 05019906 A1 | 3/2005 |
| WO | 06025726 A1 | 3/2006 |
| WO | 2006047698 A1 | 5/2006 |
| WO | 06060477 A2 | 6/2006 |
| WO | 2006060480 A2 | 6/2006 |
| WO | 2006067255 A1 | 6/2006 |
| WO | 2007092948 A1 | 8/2007 |
| WO | 2007133384 A2 | 11/2007 |
| WO | 2008045847 A2 | 4/2008 |
| WO | 2008150982 A1 | 12/2008 |
| WO | 2009017403 A1 | 2/2009 |
| WO | 2009027438 A2 | 3/2009 |
| WO | 2009043985 A1 | 4/2009 |
| WO | 2009058755 A1 | 5/2009 |
| WO | 2009076670 A1 | 6/2009 |
| WO | 2009130610 A2 | 10/2009 |
| WO | 2009148454 A1 | 12/2009 |
| WO | 2010046356 A1 | 4/2010 |
| WO | 2010054255 A1 | 5/2010 |
| WO | 2010059764 A1 | 5/2010 |
| WO | 2010079528 A1 | 7/2010 |
| WO | 2010093975 A2 | 8/2010 |
| WO | 2010100523 A1 | 9/2010 |
| WO | 2010104530 A1 | 9/2010 |
| WO | 2010144315 A1 | 12/2010 |
| WO | 2011024125 A1 | 3/2011 |
| WO | 2011055228 A2 | 5/2011 |
| WO | 2011075641 A2 | 6/2011 |
| WO | 2011075668 A1 | 6/2011 |
| WO | 2012004746 A2 | 1/2012 |
| WO | 2012031211 A1 | 3/2012 |
| WO | 2012070313 A1 | 5/2012 |
| WO | 2012078763 A1 | 6/2012 |
| WO | 2012085917 A1 | 6/2012 |
| WO | 2012122411 A1 | 9/2012 |
| WO | 2012140389 A1 | 10/2012 |
| WO | 2013018379 A1 | 2/2013 |
| WO | 2013028992 A1 | 2/2013 |
| WO | 2013093916 A1 | 6/2013 |
| WO | 2013114209 A2 | 8/2013 |
| WO | 2013116133 A1 | 8/2013 |
| WO | 2013118177 A1 | 8/2013 |
| WO | 2013118499 A1 | 8/2013 |
| WO | 2014008343 A1 | 1/2014 |
| WO | 2014033543 A2 | 3/2014 |
| WO | 2014091528 A1 | 6/2014 |
| WO | 2014111831 A1 | 7/2014 |
| WO | 2014189049 A1 | 11/2014 |
| WO | 2017137841 A1 | 8/2017 |
| WO | 2017149403 A1 | 9/2017 |
| WO | 2019130030 A1 | 7/2019 |

OTHER PUBLICATIONS

Seitz B., et al, "Corneal Topography," Current Opinion in Ophthalmolgy, 1997, vol. 8 (4), pp. 8-24.
Smith G. et al., "The spherical aberration of the crystalline lens of the human eye," Vision Res., 2001, 41 (2), 235-243.
Smith Kinney, "Sensitivity of the eye to spectral radiation at scotopic and mesopic intensity levels," Journal of the Optical Society of America, 1955, 45 (7), 507-514.

(56) References Cited

OTHER PUBLICATIONS

Thibos L. N. et al., "The chromatic eye: a new reduced-eye model of ocular chromatic aberration in humans," Applied Optics, 1992, 31 (19), 3594-3600.
Thibos L. N. et al., "Theork and measurement of ocular chromatic aberration," Vision Res, 1988, 30 (1), 33-49.
Townsley, "New Knowledge of the corneal contour," Contacto, 1970, pp. 38-43.
Verriest G., "The Spectral Curve of Relative Luminous Efficiency in Different Age Groups of Aphakic Eyes," Mod Probl Ophthalmol., 1974, 13, 314-317.
Wang J.Y., et al, "Wave-Front Interpretation With Zernike Polynomials," Applied Optics, 1980, vol. 19 (9), pp. 1510-1518.
Albert D.M., "(Book Review) Intraocular Lenses: Evolution, Designs, Complications, and Pathology, by David Apple et al.," Archieves of Opthalmology, 1990, vol. 108, pp. 650.
Alvarez S. L. et al., "Spectral threshold: measurement and clinical applications," British Journal of Ophthalmology, 1983, 67, 504-507.
Apple D.J., et al., Eds., "Intraocular Lenses: Evolution, Designs, Complications and Pathology," in: New Concepts in Intraocular Lens Implantation, Williams & Wilkins publisher, Jan. 1989, vol. 22 (36), pp. 205-221.
Apple D.J., et al., Eds., "Intraocular Lenses: Evolution, Designs, Complications and Pathology," in: New Concepts in Intraocular Lens Implantation, Williams & Wilkins publisher, Jan. 1989, vol. 36 (1), pp. 21-36.
Artal P., et al., "Contributions of the Cornea and the Lens to the Aberrations of the Human Eye," Optics Letters, 1998, vol. 23 (21), pp. 1713-1715.
Atchinson D.A., "Design of Aspheric Intraocular Lens," Ophthamic & Physiological Optics, 1991, vol. 11 (2), pp. 137-146.
Atchinson D.A., et al., "Optical Design of Intraocular Lenses. II. Off-Axis performance," Optometry & Vision Science, 1989, vol. 66 (9), pp. 579-590.
Atchinson D.A., et al., "Third-Order Aberrations of Pseudophakic Eyes," Ophthalmic and Physiological Optics, 1989, vol. 9, pp. 205-211.
Atchinson D.A., "Optical Design of Intraocular Lenses. I. On-Axis Performance," American Academy of Optometry, 1989, vol. 66 (8), pp. 492-506.
Atchinson D.A., "Optical design of intraocular lenses III. On-Axis Performance in the Presence of Lens Displacement," American Academy of Optometry, 1989, vol. 66 (10), pp. 671-681.
Atchinson, "Refractive errors induced by displacement of intraocular lenses within the pseudophakic eye," Optometry & Vision Science, 1989, 66 (3), 146-152.
Bonnet R., et al, "New Method of Topographical Ophthalmometry-Its Theoretical and Clinical Applications," American Journal of Optometry, 1962, vol. 39 (5), pp. 227-251.
Bradley A. et al., "Achromatizing the Human Eye" Optometry & Vision Science, 1991, vol. 68 (8), pp. 608-616.
Buralli D.A., et al, "Optical Performance of Holographic Kinoforms," Applied Optics, Mar. 1989, vol. 28 (5), pp. 976-983.
Cohen A.L., "Diffractive Bifocal Lens Design," Optometry and Vision Science, Jun. 1993, vol. 70 (6), pp. 461-468.
Cohen A.L., "Practical Design of a Bifocal Hologram Contact Lens or Intraocular Lens," Applied Optics, Jul. 1, 1992, vol. 31 (19), pp. 3750-3754.
Dwyer W. O. et al., "Racial Differences in Color Vision: Do They Exist", American Journal of Optometry & Physiological Optics, 1975, 52, 224-229.
El Hage S.G., et al., "Contribution of the Crystalline Lens to the Spherical Aberration of the Eye," 1973, vol. 63 (2), pp. 205-211.
European Search Report for Application No. 12181569, dated Sep. 18, 2012, 7 pages.
Futhey J.A., "Diffractive Bifocal Intraocular Lens," SPIE, 1989, vol. 1052, pp. 142-148.
Geun Y., et al., "Visual Performance after Correcting the Monochromatic and Chromatic Aberrations of the Eye," Journal of the Optical Society of America, 2002, vol. 19 (2), pp. 266-275.

Glasser A. et al., "Presbyopia and the optical changes in the human crystalline lens with age," Vision Res, 1998, 38 (2), 209-229.
Greivenkamp J.E., et al., "Visual Acuity Modeling Using Optical Raytracing of Schematic Eyes," American Journal of Ophthalmology, 1995, vol. 120 (2), pp. 227-240.
Griswold Scott et al., "Scotopic Spectral Sensitivity of Phakic and Aphakic Observers Extending into the Near Ultraviolet," Vision res, 1992, 32 (9), 1739-1743.
Guirao A., et al., "Corneal Wave Aberration from Videokeratography: Accuracy and Limitations of the Procedure," Journal of the Optical Society of America, 2000, vol. 17 (6), pp. 955-965.
International Preliminary Examination Report for PCT/EP03/13683, dated Sep. 16, 2004, 2 pages.
International Preliminary Report on Patentability and Written Opinion for Application No. PCT/US2005/038820, dated May 1, 2007, 6 pages.
International Preliminary Report on Patentability and Written Opinion for Application No. PCT/US2005/38821, dated May 1, 2007, 6 pages.
International Search Report and Written Opinion for Application No. PCT/IB2013/002390 dated May 12, 2014, 24 pages.
International Search Report for Application No. PCT/EP03/13683, dated Mar. 29, 2004, 6 pages.
International Search Report for Application No. PCT/US2005/38820, dated Mar. 3, 2006, 3 pages.
International Search Report for Application No. PCT/US2005/38821, dated Mar. 3, 2006, 3 pages.
IOVS, 1999, 40 (4), S535.
Kiely et al., "The mean shape of the human cornea," Optica ACTA, 1982, 29 (8), 1027-1040.
Kokoschka S., et al., "Influence of Field Size on the Spectral Sensitivity of the Eye in the Photopic and Mesopic Range," American Journal of Optometry and Physiological Optics, 1985, vol. 62 (2), pp. 119-126.
Liang J., et al, "Objective Measurement of Wave Aberrations of the Human Eye With the Use of a Hartmann-Shack Wave-Front Sensor," Journal of the Optical Society of America, 1994, vol. 11 (7), pp. 1949-1957.
Lindsay R., et al., "Descriptors of Corneal Shape," Optometry and Vision Science, 1998, vol. 75 (2), pp. 156-158.
Lotmar, "Theoretical eye model with aspherics," Journal of the Optical Society of America, 1971, 61 (11), 1522-1529.
Malacara D., et al., "Wavefront Fitting With Discrete Orthogonal Polynomials in a Unit Radius Circle," Optical Engineering, 1990, vol. 29 (6), pp. 672-675.
Mandell R.B., et al., "Mathematical Model of the Corneal Contour," 1965, School of Optometry, University of California, Berkeley, pp. 183-197.
Marcos S., et al., "A New Approach to the Study of Ocular Chromatic Aberrations," Vision Research, 1999, vol. 39 (26), pp. 4309-4323.
Mordi J.A., et al., "Influence of Age of Chromatic Aberration of the Human Eye," American Journal of Optometry & Physiological Optics, 1985, vol. 62 (12), pp. 864-869.
Navarro R., et al., "Accommodation-Dependent Model of the Human Eye with Aspherics," Journal of the Optical Society of America, Aug. 1985, vol. 2 (8), pp. 1273-1281.
Norrby S., et al., "Model Eyes for Evaluation of Intraocular Lenses," Applied Optics, Sep. 7, 2007, vol. 46 (26), pp. 6595-6605.
Office Action dated Jul. 5, 2011 for Japanese Application No. 2007539132 filed Oct. 25, 2005.
"Optical Design," Military Standardization Handbook, 1962, Chapter 4, U.S. Department of Defense MIL-HDBK-141, 4-1-4-19.
Oshika T., et al., "Changes in Corneal Wavefront Aberrations with Aging," Investigative Ophthalmology & Visual Science, 1999, vol. 40 (7), pp. 1351-1355.
Patel S., et al., "Shape and Radius of Posterior Corneal Surface," Refractive and Corneal Surgery, 1993, vol. 9 (3), pp. 173-181.
Piers P.A., et al., "Theoretical Comparison of Aberration-Correcting Customized and Aspheric Intraocular Lenses," Journal of Refractive Surgery, Apr. 2007, vol. 23 (4), pp. 374-384.

(56) References Cited

OTHER PUBLICATIONS

Said et al., "The Variation with Age of the Spectral Transmissivity of the Living Human Crystalline Lens," Gerontologia, 1959, 213-231.
Alfonso J.F., et al., "Prospective Study of the Acri.LISA Bifocal Intraocular Lens," Journal of Cataract Refractive Surgery, Nov. 2007, vol. 33 (11), pp. 1930-1935.
Canovas C., et al., "Hybrid Adaptive-Optics Visual Simulator," Optical Letters, Jan. 15, 2010, vol. 35 (2), pp. 196-198.
Diffractive Lenses for Extended Depth of Focus and Presbyopic Correction, Presentation from Wavefront Congress held on Feb. 15, 2008, Rochester, New York.
Doskolovich L.L., et al., "Special Diffractive Lenses," Lens and Optical Systems Design, Apr. 1992, vol. 1780, pp. 393-402.
Liou H.L., et al., "Anatomically Accurate, Finite Model Eye for Optical Modeling," Journal of Optical Society of America, Aug. 1997, vol. 14 (8), pp. 1684-1695.
Marsack J.D., et al., "Metrics of Optical Quality Derived from Wave Aberrations Predict Visual Performance," Journal of Vision, Apr. 2004, vol. 4 (4), pp. 322-328.
Monsoriu J.A., et al., "Devil's Lenses," Optics Express, Oct. 17, 2007, vol. 15 (21), pp. 13858-13864.
Morlock, R., et al., "Patient-Reported Spectacle Independence Questionnaire (PRSIQ): Development and Validation," American Journal of Ophthalmology, Jun. 2017, vol. 178, pp. 101-114.
Piers P.A., et al., "Eye Models for the Prediction of Contrast Vision in Patients with New Intraocular Lens Designs," Optics Letters, Apr. 1, 2004, vol. 29 (7), pp. 733-735.
Siedlecki D., et al., "Radial Gradient index Intraocular Lens: a Theoretical Model," Journal of Modern Optics, Feb. 20-Mar. 10, 2008, vol. 55 (4-5), pp. 639-647.
Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.
Van Den Berg T.J., "Analysis of Intraocular Straylight, Especially in Relation to Age," Optometry and Vision Science Feb. 1995, vol. 72 (2), pp. 52-59.
Van Meeteren A., "Calculations on the Optical Modulation Transfer Function of the Human Eye for White Light," Optica Acta, May 1974, vol. 21 (5), pp. 395-412.
Villegas E.A., et al., "Correlation between Optical and Psychophy, Sical Parameters as a Function of Defocus," Optometry and Vision Science, Jan. 1, 2002, vol. 79 (1), pp. 60-67.
Castignoles F., et al., "Comparison of the Efficiency, MTF and Chromatic Properties of Four Diffractive Bifocal Intraocular Lens Designs," Optics Express, Mar. 2010, vol. 18 (5), pp. 5245-5256.
Sokolowski M., et al. "Hybrid Heptafocal Intraocular Lenses, " Optica Applicata, Dec. 2015, vol. 45 (3), pp. 285-298.

* cited by examiner

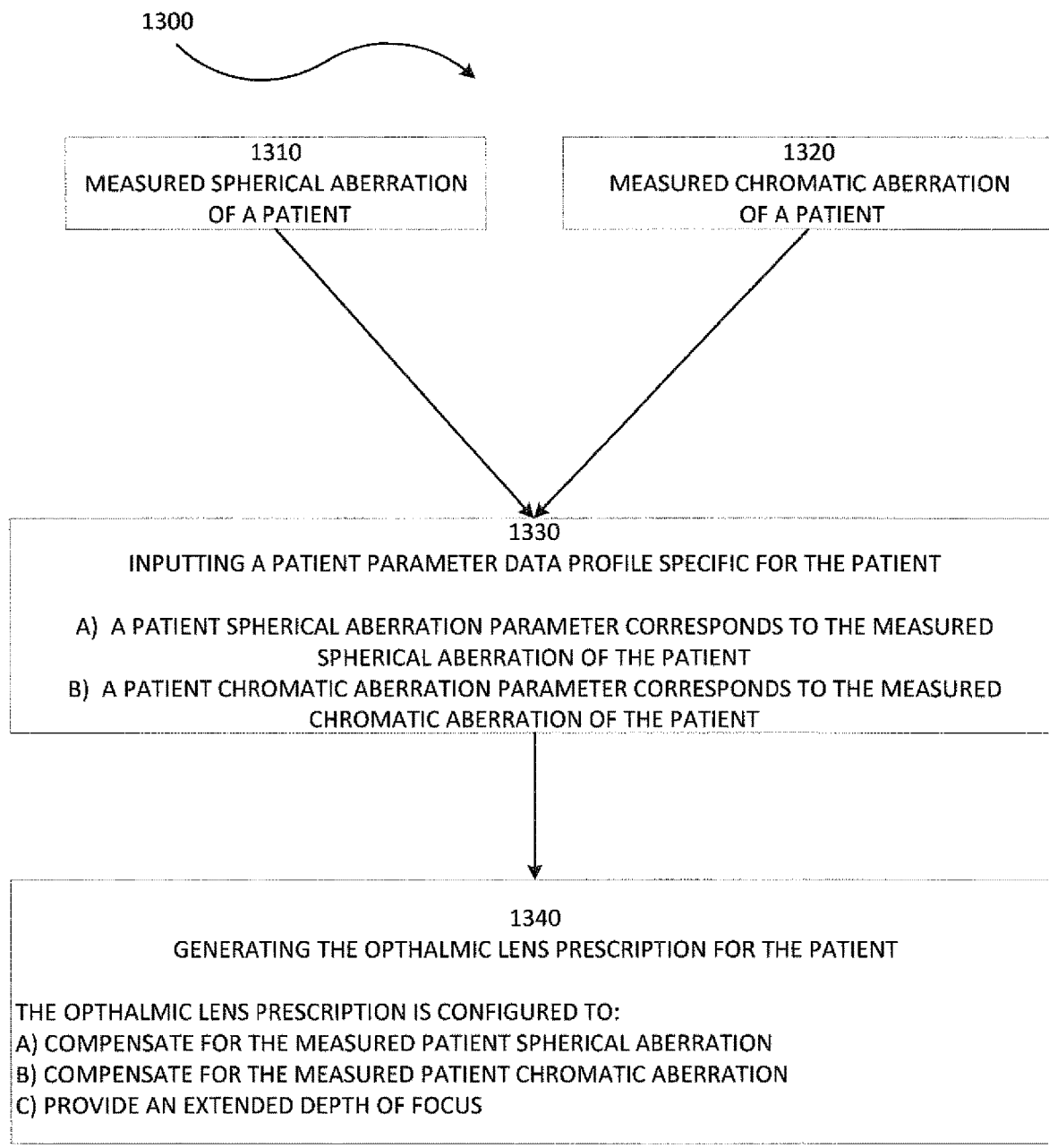

1410
INPUTTING AN OPTHALMIC LENS PRESCRIPTION FOR A PATIENT

THE OPTHALMIC LENS PRESCRIPTION IS CONFIGURED TO:
A) COMPENSATE FOR THE MEASURED PATIENT SPHERICAL ABERRATION
B) COMPENSATE FOR THE MEASURED PATIENT CHROMATIC ABERRATION
C) PROVIDE AN EXTENDED DEPTH OF FOCUS

1420
FABRICATING AN OPTHALMIC LENS BASED ON THE PRESCRIPTION

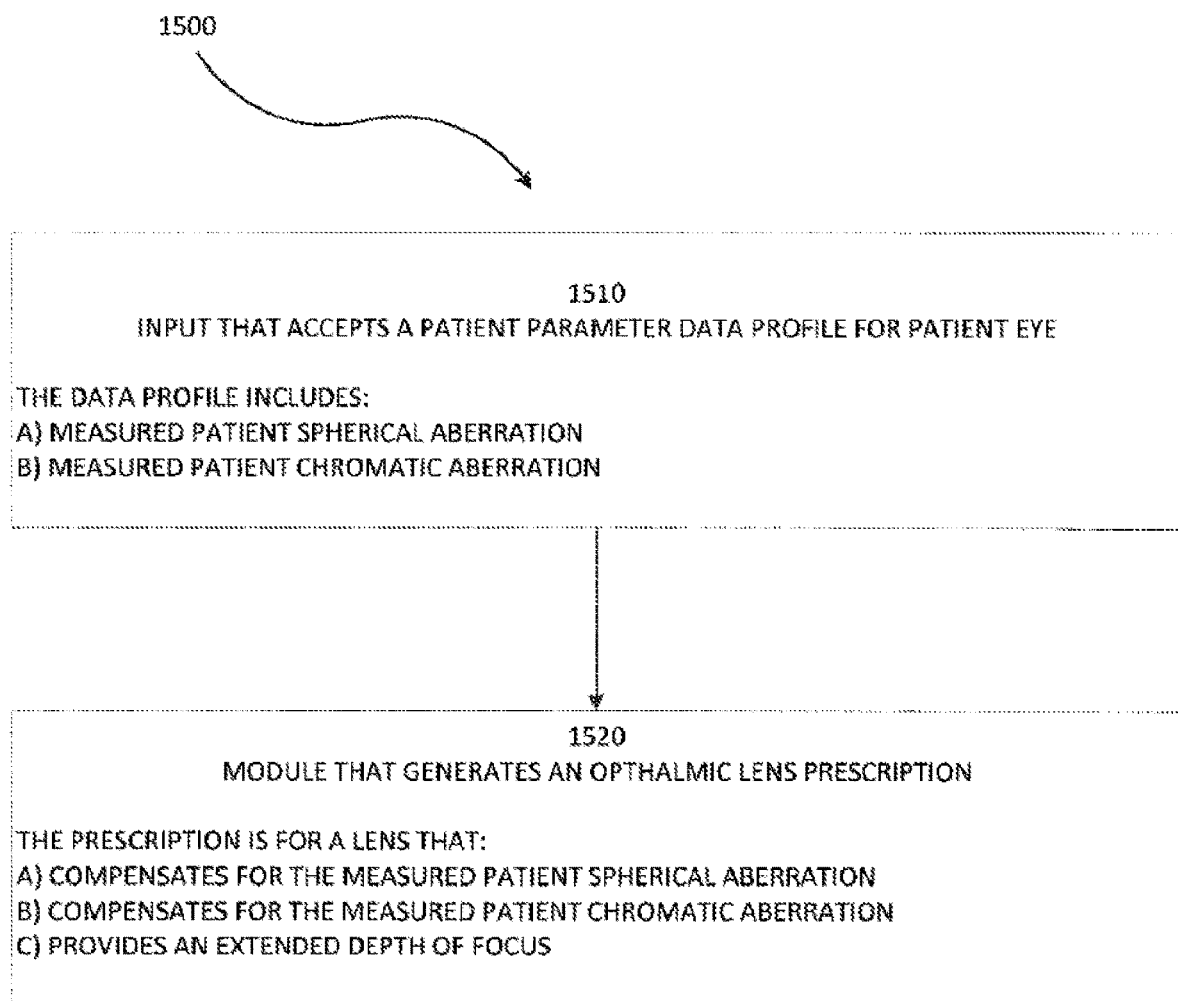

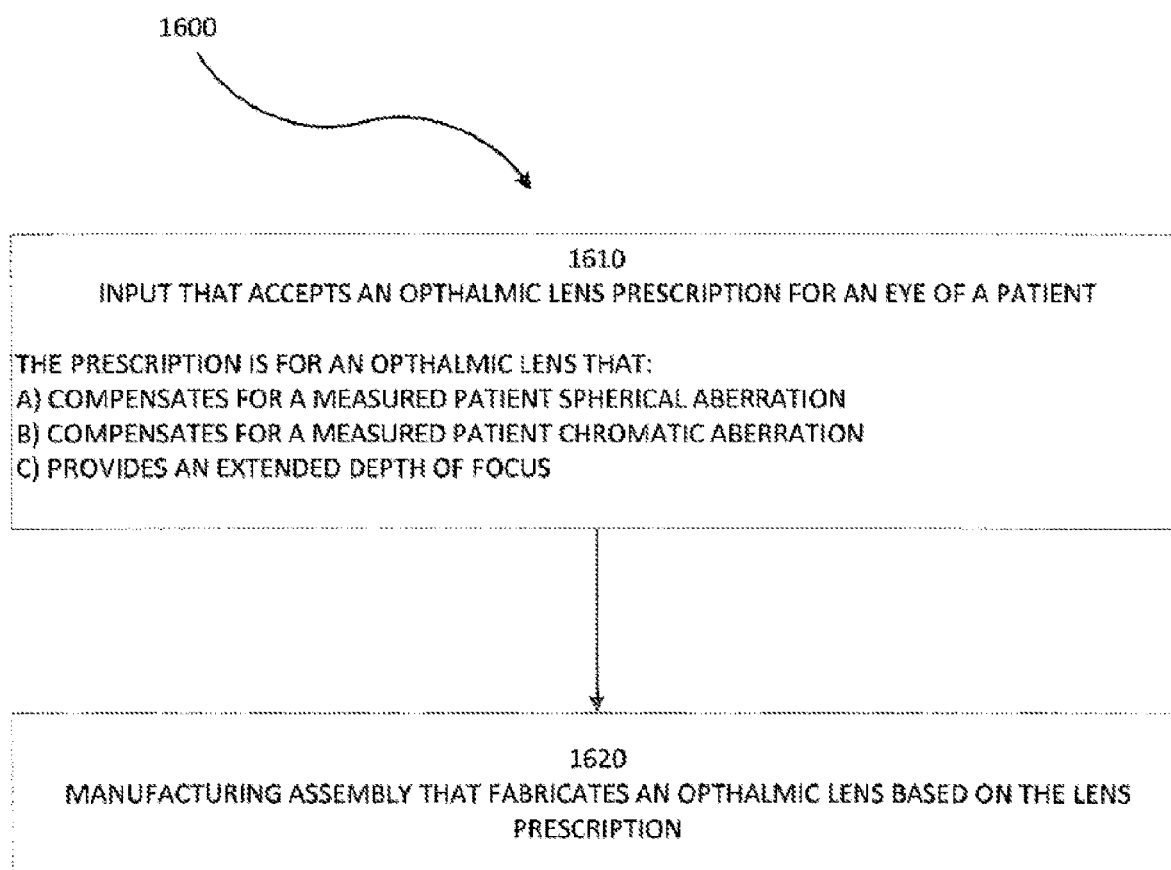

MULTI-RING LENS, SYSTEMS AND METHODS FOR EXTENDED DEPTH OF FOCUS

CROSS-REFERENCES TO RELATED APPLICATIONS

The present application is a continuation application of and claims priority to U.S. application Ser. No. 15/149,574, filed on May 9, 2016, which is a divisional application of and claims priority to U.S. application Ser. No. 14/014,701, filed on Aug. 30, 2013, now U.S. Pat. No. 9,335,563, which claims priority under 35 U.S.C. § 119(e) to U.S. Provisional Application No. 61/695,806, filed on Aug. 31, 2012. This application is related to U.S. patent application Ser. No. 12/971,607 filed Dec. 17, 2010, now U.S. Pat. No. 8,480,228, which issued on Jul. 9, 2013, which claims the benefit of priority to U.S. Provisional Patent Application No. 61/288,255 filed Dec. 18, 2009. Further, this application is related to the following applications which were filed Dec. 17, 2010: Single Microstructure Lens, Systems and Methods, U.S. patent application Ser. No. 12/971,506, now U.S. Pat. No. 8,430,508, which issued on Apr. 30, 2013; Ophthalmic Lens, Systems And Methods With Angular Varying Phase Delay, U.S. patent application Ser. No. 12/971,889, now U.S. Pat. No. 8,444,267, which issued on May 21, 2013; and Ophthalmic Lens, Systems And Methods Having At Least One Rotationally Asymmetric Diffractive Structure, U.S. Patent Application No. 61/424,433. This application is also related to the following U.S. Patent Application No. 61/047,699 and Ser. No. 12/109,251, now U.S. Pat. No. 7,871,162, which issued on Jan. 18, 2011, both filed on Apr. 24, 2008; Ser. No. 12/429,155 filed on Apr. 23, 2009, now U.S. Pat. No. 8,231,219, which issued on Jul. 31, 2012; Ser. No. 12/372,573 filed on Feb. 17, 2009, now abandoned; Ser. No. 12/197,249 filed on Aug. 23, 2008; Ser. No. 12/120,201 filed on Apr. 13, 2008, and Ser. No. 12/771,550 filed on Apr. 30, 2010. What is more, this application is related to U.S. Pat. Nos. 6,830,332 and 7,896,916. The entire disclosure of each of the above filings is incorporated herein by reference for all purposes. Full Paris Convention priority is hereby expressly reserved.

BACKGROUND OF THE INVENTION

Embodiments of the present invention relate to vision treatment techniques and in particular, to ophthalmic lenses such as, for example, contact lenses, corneal inlays or onlays, or intraocular lenses (IOLs) including, for example, phakic IOLs and piggyback IOLs (i.e. IOLs implanted in an eye already having an IOL).

Presbyopia is a condition that affects the accommodation properties of the eye. As objects move closer to a young, properly functioning eye, the effects of ciliary muscle contraction and zonular relaxation allow the lens of the eye to change shape, and thus increase its optical power and ability to focus at near distances. This accommodation can allow the eye to focus and refocus between near and far objects.

Presbyopia normally develops as a person ages, and is associated with a natural progressive loss of accommodation. The presbyopic eye often loses the ability to rapidly and easily refocus on objects at varying distances. The effects of presbyopia usually become noticeable after the age of 45 years. By the age of 65 years, the crystalline lens has often lost almost all elastic properties and has only limited ability to change shape.

Along with reductions in accommodation of the eye, age may also induce clouding of the lens due to the formation of a cataract. A cataract may form in the hard central nucleus of the lens, in the softer peripheral cortical portion of the lens, or at the back of the lens. Cataracts can be treated by the replacement of the cloudy natural lens with an artificial lens. An artificial lens replaces the natural lens in the eye, with the artificial lens often being referred to as an intraocular lens or "IOL".

Monofocal IOLs are intended to provide vision correction at one distance only, usually the far focus. Predicting the most appropriate IOL power for implantation has limited accuracy, and an inappropriate IOL power can leave patients with residual refraction following surgery. Accordingly, it may be necessary for a patient who has received an IOL implant to also wear spectacles to achieve good far vision. At the very least, since a monofocal IOL provides vision treatment at only one distance and since the typical correction is for far distance, spectacles are usually needed for good near vision and sometimes intermediate vision. The term "near vision" generally corresponds to vision provided when objects are at a distance from the subject eye of between about 1 to 2 feet are substantially in focus on the retina of the eye. The term "distant vision" generally corresponds to vision provided when objects at a distance of at least about 6 feet or greater are substantially in focus on the retina of the eye. The term "intermediate vision" corresponds to vision provided when objects at a distance of about 2 feet to about 5 feet from the subject eye are substantially in focus on the retina of the eye.

There have been various attempts to address limitations associated with monofocal IOLs. For example, multifocal IOLs have been proposed that deliver, in principle, two foci, one near and one far, optionally with some degree of intermediate focus. Such multifocal or bifocal IOLs are intended to provide good vision at two distances, and include both refractive and diffractive multifocal IOLs. In some instances, a multifocal IOL intended to correct vision at two distances may provide a near add power of about 3.0 or 4.0 Diopters.

Multifocal IOLs may, for example, rely on a diffractive optical surface to direct portions of the light energy toward differing focal distances, thereby allowing the patient to clearly see both near and far objects. Multifocal ophthalmic lenses (including contact lenses or the like) have also been proposed for treatment of presbyopia without removal of the natural crystalline lens. Diffractive optical surfaces, either monofocal or multifocal, may also be configured to provide reduced chromatic aberration.

Diffractive monofocal and multifocal lenses can make use of a material having a given refractive index and a surface curvature which provide a refractive power. Diffractive lenses have a diffractive profile which confers the lens with a diffractive power that contributes to the overall optical power of the lens. The diffractive profile is typically characterized by a number of diffractive zones. When used for ophthalmic lenses these zones are typically annular lens zones, or echelettes, spaced about the optical axis of the lens. Each echelette may be defined by an optical zone, a transition zone between the optical zone and an optical zone of an adjacent echelette, and an echelette geometry. The echelette geometry includes an inner and outer diameter and a shape or slope of the optical zone, a height or step height, and a shape of the transition zone. The surface area or diameter of the echelettes largely determines the diffractive power(s) of the lens and the step height of the transition between echelettes largely determines the light distribution between the different add powers. Together, these echelettes form a diffractive profile.

A multifocal diffractive profile of the lens may be used to mitigate presbyopia by providing two or more optical powers; for example, one for near vision and one for far vision. The lenses may also take the form of an intraocular lens placed within the capsular bag of the eye, replacing the original lens, or placed in front of the natural crystalline lens. The lenses may be in the form of a contact lens, most commonly a bifocal contact lens, or in any other form mentioned herein.

Although multifocal ophthalmic lenses lead to improved quality of vision for many patients, additional improvements would be beneficial. For example, some pseudophakic patients experience undesirable visual effects (dysphotopsia), e.g. glare or halos. Halos may arise when light from the unused focal image creates an out-of-focus image that is superimposed on the used focal image. For example, if light from a distant point source is imaged onto the retina by the distant focus of a bifocal IOL, the near focus of the IOL will simultaneously superimpose a defocused image on top of the image formed by the distant focus. This defocused image may manifest itself in the form of a ring of light surrounding the in-focus image, and is referred to as a halo. Another area of improvement revolves around the typical bifocality of multifocal lenses. Since multifocal ophthalmic lenses typically provide for near and far vision, intermediate vision may be compromised.

A lens with an extended depth of focus may provide certain patients the benefits of good vision at a range of distances, while having reduced or no dysphotopsia. Various techniques for extending the depth of focus of an IOL have been proposed. For example, some approaches are based on a bulls-eye refractive principle, and involve a central zone with a slightly increased power. Other techniques include an asphere or include refractive zones with different refractive zonal powers.

Although certain proposed treatments may provide some benefit to patients in need thereof, still further advances would be desirable. For example, it would be desirable to provide improved IOL systems and methods that confer enhanced image quality across a wide and extended range of foci without dysphotopsia. Embodiments of the present invention provide solutions that address the problems described above, and hence provide answers to at least some of these outstanding needs.

BRIEF SUMMARY OF THE INVENTION

Embodiments of the present invention generally provide improved lenses and imaging techniques. Exemplary embodiments provide improved ophthalmic lenses (such as, for example, contact lenses, corneal inlays or onlays, or intraocular lenses (IOLs) including, for example, phakic IOLs and piggyback IOLs) and associated methods for their design and use.

Embodiments of the present invention encompass IOL optics having a circular surface structure with one to four echelettes surrounding the surface structure. The profile is designed such that it increases the depth of focus of the pseudophakic eye, where the natural crystalline lens of the eye is substituted with a synthetic lens. Such limited ring IOL techniques suppress the distinct bifocality associated with traditional multifocal IOLs which have many diffractive rings. Consequently, dysphotopsia (e.g., halo effects) associated with traditional multifocal IOLs can be alleviated by lenses according to embodiments of the present invention.

An exemplary limited ring IOL includes an anterior face and a posterior face. A profile can be imposed on the anterior or posterior surface or face. The profile can have an inner portion and an outer portion. The inner portion typically presents a parabolic curved shape. The inner portion may also be referred to as a microstructure, or a central or inner echelette. Between the inner portion and the outer portion, there may be a transition zone that connects the inner and outer portions. The outer portion may be comprised of four or fewer echelettes.

In addition to parabolic shapes, the central/inner echelette can have any of a variety of shapes including hyperbolic, spherical, aspheric, and sinusoidal. The transition between the inner and outer portions of the central/inner echelette can be a sharp transition, or it can be a smooth transition.

The surface of the outer portion at the outside of the microstructure can have any spherical or aspherical shape and is comprised of a limited number of echelettes, preferably less than four. The shape of the outer portion can be optimized for having the desired optical performance for a range of pupil sizes. The desired optical performance can be based on elements such as the depth of focus, the optical quality in the far focus, and the change in best focus (or far focus) position as a function of the pupil size. Optimization rules may be applied as if the shape were a refractive monofocal IOL, or a refractive IOL having an extended depth of focus, or a refractive design that corrects or modifies the ocular spherical aberration. Specific designs can be made in which the interplay between the central echelette and the outer zone is incorporated in the design or optimization. The techniques described herein are well suited for implementation with any of a variety of ophthalmic lenses, including IOLs, corneal inlays or onlays, and/or contact lenses.

In one aspect, embodiments of the present invention encompass ophthalmic lens systems and methods for treating an eye of a patient. An exemplary lens may include an anterior face with an anterior refractive profile and a posterior face with a posterior refractive profile. The faces may be disposed about an optical axis. The lens may also include a diffractive profile imposed on the anterior refractive profile or the posterior refractive profile. In some cases, the diffractive profile may include no more than 5 echelettes. Optionally, the central echelette can be disposed within a central zone of the lens. Relatedly, the central echelette may be disposed within an annular ring surrounding a central refractive zone of the lens. In some cases, the lens includes a peripheral zone with a limited number of echelettes that surround the central echelette or annular ring. The limited number of echelettes may be characterized by a constant phase shift.

According to some embodiments, an ophthalmic lens can include a limited number of echelettes that are characterized by parabolic curves. The central echelette can have a diameter within a range from about 1 mm to about 4 mm. For example, the central echelette may have a diameter of about 1.5 mm. In some cases, the central echelette can have a diameter within a range from about 1.0 mm to about 5.0 mm. Lens embodiments may include a peripheral portion comprised of a limited number of echelettes and a refractive portion. Central and peripheral echelettes can have a surface area that is between 1 and 7 $mm^2$. For example, the echelettes may have a surface area that is 2.3 $mm^2$. In some cases, a lens may include a peripheral portion which surrounds the echelettes. A lens may include a peripheral portion having an outer diameter within a range from about 4 mm to about 6 mm. In some cases, the peripheral portion will have an outer diameter within a range of about 1 mm to about 7 mm. For example, a lens may include a peripheral portion having an outer diameter of about 5 mm.

The echelettes may be characterized by a step height having a value within a range from about 0.5 µm and about 4 µm. According to some embodiments, a transition can be characterized by a step height having a value within a range of about 1.5 µm and 2.5 µm. According to some embodiments, a transition can be characterized by a step height having a value of about 1.7 µm. In other embodiments, the step height may have a value of about 2.0 µm.

Optionally, a diffractive profile can be characterized by a design wavelength, and a lens can include a transition characterized by a step height producing a phase shift between about 0.25 and about 1 times the design wavelength. In some cases, a diffractive profile can be characterized by a design wavelength, and the lens can include a transition characterized by a step height producing a phase shift between about 0.15 and about 2 times the design wavelength.

In some aspects, embodiments of the present invention encompass systems and methods involving an ophthalmic lens that include an anterior face with an anterior refractive profile and a posterior face with a posterior refractive profile, such that the faces are disposed about an optical axis, and a diffractive profile imposed on the anterior refractive profile or the posterior refractive profile, such that the diffractive profile includes an inner echelette and four or fewer outer echelettes. According to some embodiments, an inner echelette can be disposed within a central zone of the lens. In some cases, an inner echelette can be disposed within an annular ring surrounding a central zone of the lens. Optionally, an inner echelette and outer echelettes can be characterized by a parabolic curve. In some cases, an inner echelette and outer echelettes can be characterized by a constant phase shift. According to some embodiments, an ophthalmic lens may include an accommodating lens and/or a multifocal lens.

In one aspect, embodiments of the present invention encompass ophthalmic lenses, and systems and methods for their design and fabrication. Exemplary ophthalmic lenses may include a first surface and a second surface, where the first and second surfaces are disposed about an optical axis, an aspheric refractive profile imposed on the first or second surface, and a diffractive profile imposed on the first or second surface. The aspheric refractive profile can focus or direct light toward a far focus. The diffractive profile may include a central zone that distributes a first percentage of light toward a far focus and a second percentage of light toward an intermediate focus, and a peripheral zone, surrounding the central zone, that distributes a third percentage of light toward the far focus and a fourth percentage of light toward the intermediate focus. In some instances, the intermediate focus corresponds to an intraocular add power within a range between 1 Diopter and 2.5 Diopters. In some instances, the intermediate focus corresponds to an add power between 0.75 and 2 Diopters in the spectacle plane. In some instances, the intermediate focus corresponds to an intraocular add power of 1.75 Diopters. According to some embodiments, the far focus corresponds to a first diffractive order of the diffractive profile. In some cases, the far focus corresponds to a second diffractive order of the diffractive profile. In some cases, the far focus corresponds to a third diffractive order of the diffractive profile. In some cases, a difference between the intermediate focus and the far field focus corresponds to a power value within a range from about 1 Diopter to about 2.5 Diopters. Optionally, a difference between the intermediate focus and the far field focus may correspond to a power of about 1.75 Diopters. According to some embodiments, the central zone has an outer diameter within a range from about 1 mm to about 3 mm. According to some embodiments, the central zone has an outer diameter of about 2.2 mm. In some instances, the percentage of light distributed by the central zone toward the far focus is within a range between 41% and 63%, and the percentage of light distributed by the central zone toward the intermediate focus is within a range between 21% and 41%. In some instances, the percentage of light distributed by the central zone toward the far focus is 41% and the percentage of light distributed by the central zone toward the intermediate focus 41%. In some instances, the percentage of light distributed by the peripheral zone toward the far focus is within a range between 41% and 100% and the percentage of light distributed by the peripheral zone toward the intermediate focus is within a range from 0% to 41%. In some instances, the percentage of light distributed by the peripheral zone toward the far focus is 63% and the percentage of light distributed by the peripheral zone toward the intermediate focus is 21%. Optionally, the central zone may include one or more echelettes each having a step height, and the peripheral zone may include a plurality of echelettes each having a step height that is less than the step height of each central zone echelette. In some instances, the central zone includes two or more echelettes. Optionally, the central zone may include three or more echelettes. In some instances, the central zone may include two, three, four echelettes. According to some embodiments, the central zone includes at least one echelette having a step height of about 0.006 millimeters, and the peripheral zone includes at least one echelette having a step height of about 0.0055 millimeters. In some instances, the central zone includes at least one echelette having an optical path difference of 1.5 wavelengths, and the peripheral zone includes at least one echelette having an optical path difference of 1.366 wavelengths. In some instances, the central zone includes two echelettes each having a step height, and the peripheral zone includes seven echelettes each having a step height less than the step heights of the central zone echelettes. In some instances, the central zone includes an inner echelette having an outer diameter of 1.6 mm and an outer echelette having an outer diameter of 2.2 mm, where the inner and outer echelettes of the central zone each have a step height, and the peripheral zone includes seven echelettes each having a step height less than the step heights of the central zone echelettes. For an add power range of 1.0-2.5 Diopters, there may be one to five echelettes in the central zone and three to twenty four echelettes in the peripheral zone. For an add power range of 0.75-2.0 Diopters, there may be one to four echelettes in the central zone and three to nineteen echelettes in the peripheral zone. In some instances, the peripheral zone may have in the range of five to twelve echelettes. Optionally, the lens may provide an MTF at 50 c/mm of 24 at the intermediate focus and an MTF at 50 c/mm of 44 at the far focus.

In another aspect, embodiments of the present invention encompass ophthalmic lenses that include means for compensating for ocular spherical aberration, means for compensating for ocular chromatic aberration, and means for providing an extended depth of focus. In some instances, the means for providing an extended depth of focus includes a lens surface having a diffractive profile. In some instances, the means for providing an extended depth of focus includes a lens surface having a refractive profile. In some instances, the means for providing an extended depth of focus includes a lens surface having a diffractive and a refractive profile. In some instances, the means for providing an extended depth of focus includes a lens surface having a profile that is neither diffractive nor refractive.

In another aspect, embodiments of the present invention encompass ophthalmic lenses that include means for compensating for ocular spherical aberration, and means for compensating for ocular chromatic aberration. The means for compensating for ocular chromatic aberration and the means for compensating for ocular spherical aberration when combined can provide a far focus corresponding to a base power and an intermediate focus corresponding to an add power, and a difference between the base power and the add power can define an extended depth of focus for the lens. In some instances, the base power is within a range from 5 to 34 Diopters and the add power is within a range from 1 to 2.5 Diopters. In some instances, the means for compensating for ocular spherical aberration includes a lens surface having an aspherical profile. In some instances, the means for compensating for ocular chromatic aberration includes a lens surface having a diffractive profile. In some instances, the means for compensating for ocular chromatic aberration includes a lens material construction, the construction having a first material providing a first optical dispersion and a second material providing a second optical dispersion different from the first optical dispersion.

In still another aspect, embodiments of the present invention encompass ophthalmic lenses that include means for compensating for corneal spherical aberration, means for compensating for ocular chromatic aberration, and means for providing an extended depth of focus. In some instances, the means for providing an extended depth of focus includes a lens surface having a diffractive profile. In some instances, the means for providing an extended depth of focus includes a lens surface having a refractive profile. In some instances, the means for providing an extended depth of focus includes a lens surface having a diffractive and a refractive profile. In some instances, the means for providing an extended depth of focus includes a lens surface having a profile that is neither diffractive nor refractive.

In yet another aspect, embodiments of the present invention encompass ophthalmic lenses that include means for compensating for corneal spherical aberration, and means for compensating for ocular chromatic aberration. The means for compensating for ocular chromatic aberration and the means for compensating for ocular spherical aberration when combined can provide a modulation transfer function value at 50 cycles per millimeter of at least 10, for an intermediate focus, at 3 mm and 5 mm pupil diameters. In some cases, the means for compensating for corneal spherical aberration includes a lens surface having an aspherical profile. In some cases, the means for compensating for ocular chromatic aberration includes a lens surface having a diffractive profile. In some cases, the diffractive profile includes a central zone that distributes a first percentage of light toward a far focus and a second percentage of light toward the intermediate focus, and a peripheral zone, surrounding the central zone, that distributes a third percentage of light toward the far focus and a fourth percentage of light toward the intermediate focus. In some cases, the means for compensating for ocular chromatic aberration includes a lens material construction, the construction having a first material providing a first optical dispersion and a second material providing a second optical dispersion different from the first optical dispersion.

In yet another aspect, embodiments of the present invention encompass methods for generating an ophthalmic lens prescription for a patient. Exemplary methods may include inputting a patient parameter data profile specific for the patient, where the patient parameter data profile includes a patient spherical aberration parameter corresponding to a measured spherical aberration of the patient and a patient chromatic aberration parameter corresponding to a measured chromatic aberration of the patient. Methods may also include generating the ophthalmic lens prescription for the patient. The ophthalmic lens prescription can be configured to compensate for the measured patient spherical aberration and the measured patient chromatic aberration and to provide a far focus corresponding to a base power and an intermediate focus corresponding to an add power, where a difference between the base power and the add power defines an extended depth of focus for the ophthalmic lens. In some instances, the ophthalmic lens prescription may include a contact lens prescription, a phakic intraocular lens prescription, a pseudophakic intraocular lens prescription, or a corneal inlay prescription. In some instances, the patient spherical aberration parameter includes an ocular spherical aberration parameter. In some instances, the patient spherical aberration parameter includes a corneal spherical aberration parameter. In some instances, the patient chromatic aberration parameter includes an ocular chromatic aberration parameter. In some instances, the patient chromatic aberration parameter includes a corneal chromatic aberration parameter.

In still yet another aspect, embodiments of the present invention encompass methods for fabricating an ophthalmic lens prescription for a patient. Exemplary methods may include inputting an ophthalmic lens prescription for a patient, and fabricating the ophthalmic lens based on the prescription. In some cases, the ophthalmic lens is configured to compensate for a patient spherical aberration and a patient chromatic aberration, and the lens is configured to provide a far focus corresponding to a base power and an intermediate focus corresponding to an add power, where a difference between the base power and the add power defines an extended depth of focus for the ophthalmic lens. In some cases, the ophthalmic lens is a contact lens, a phakic intraocular lens, a pseudophakic intraocular lens, or a corneal inlay.

In another aspect, embodiments of the present invention encompass systems for generating an ophthalmic lens prescription for an eye of a patient. Exemplary systems may include an input that accepts a patient parameter data profile specific for the patient eye, where the patient parameter data profile includes a patient spherical aberration parameter corresponding to a measured spherical aberration of the patient eye and a patient chromatic aberration parameter corresponding to a measured chromatic aberration of the patient eye. Systems may also include a module having a tangible medium embodying machine-readable code that generates the ophthalmic lens prescription for the eye. The ophthalmic lens prescription can be configured to compensate for the measured spherical and chromatic aberrations and to provide a far focus corresponding to a base power and an intermediate focus corresponding to an add power, where a difference between the base power and the add power defines an extended depth of focus for the ophthalmic lens.

In one aspect, embodiments of the present invention encompass systems for fabricating an ophthalmic lens for an eye of a patient. Exemplary systems may include an input that accepts an ophthalmic lens prescription for the patient eye, where the ophthalmic lens prescription is configured to compensate for a measured patient spherical aberration and a measured patient chromatic aberration of the patient eye, and to provide a far focus corresponding to a base power and an intermediate focus corresponding to an add power. A difference between the base power and the add power can define an extended depth of focus for the ophthalmic lens prescription. Systems may also include a manufacturing assembly that fabricates the ophthalmic lens based on the lens prescription.

For further understanding of the nature and advantages of the present invention, reference should be made to the ensuing detailed description taken in conjunction with the accompanying drawings.

BRIEF DESCRIPTION OF THE DRAWINGS

FIGS. 8, 8-1, and 8A to 8E depict aspects of ophthalmic lenses according to embodiments of the present invention.

FIG. 13 depicts aspects of ophthalmic lens prescription generation methods according to embodiments of the present invention.

FIG. 14 depicts aspects of ophthalmic lens fabrication methods according to embodiments of the present invention.

FIG. 15 depicts aspects of ophthalmic lens prescription generation systems according to embodiments of the present invention.

FIG. 16 depicts aspects of ophthalmic lens fabrication systems according to embodiments of the present invention.

Figure 1A:
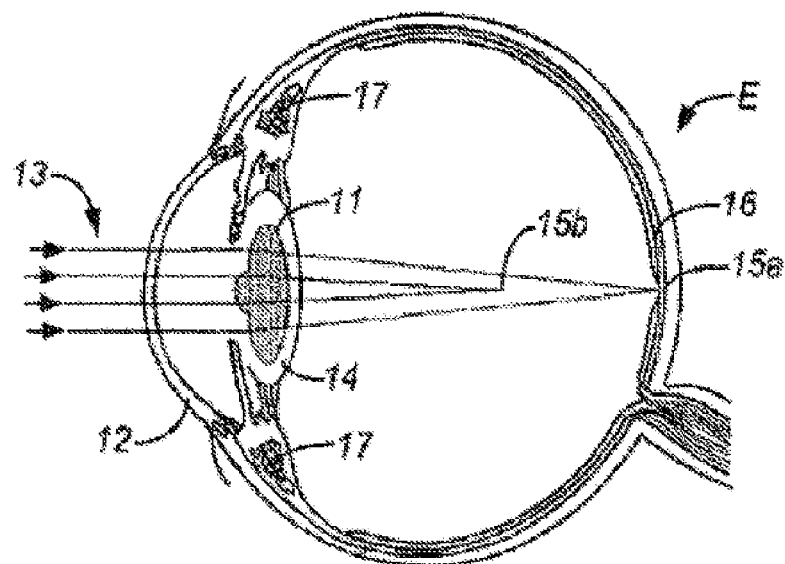
FIG. 1A is a cross-sectional view of an eye with a multifocal refractive intraocular lens.

For illustration purposes, the profile geometries shown in certain aforementioned figures were not drawn exactly to scale. The heights of the profiles shown in some of the figures are generally on the order of about 0.1 μm to about 8.0 μm although the heights may vary depending on factors such as the amount of correction needed by the patient, the refractive index of the lens material and surrounding medium, and the desired distribution of light between wanted diffraction orders.

DETAILED DESCRIPTION OF THE INVENTION

It is to be understood that the figures and descriptions of the present invention have been simplified to illustrate elements that are relevant for a clear understanding of the present invention, while eliminating, for the purpose of clarity and brevity, many other elements found in typical ophthalmic lenses, implantable optic apparatuses, systems and methods. Those of ordinary skill in the art may thus recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

Embodiments of the present invention encompass systems and methods that provide improved image quality over an extended range of focal points or foci. Systems and methods disclosed herein can encompass various ophthalmic lenses such as, for example, contact lenses, intraocular lenses, spectacle lenses, and corneal inlays or onlays. Exemplary embodiments include ophthalmic lenses having an extended depth of focus, as compared to conventional monofocal lenses, and reduced dysphtopsia as compared to conventional multifocal ophthalmic lenses. In some cases, such techniques involve an IOL approach that includes a limited number of rings or echelettes, and typically involves an expanded depth of focus. Advantageously, such approaches can provide a patient with good distance vision, as well as good vision at intermediate and/or near distances without dysphotopsia.

Embodiments of the present invention generally provide improved lenses and imaging systems and may be incorporated into any system in which a lens with an extended depth of focus may be advantageous, such as camera/video lenses, including those used for surveillance or for surgical procedures, as well as for cameras in mobile phones or other related devices. Embodiments of the invention may find their most immediate use in the form of improved ophthalmic devices, systems, and methods. Exemplary embodiments of the present invention provide improved ophthalmic lenses (including, for example contact lenses, intraocular lenses (IOLs), corneal implants and the like) and associated methods for their design and use. Embodiments of the present invention may be used with monofocal diffractive or refractive lenses, bifocal diffractive or refractive lenses, and multifocal diffractive or refractive lenses, e.g. embodiments of the present invention could be added to the opposite surface of multifocal IOLs. In other words, an extended depth of focus feature may be added to, for example the opposite surface of a diffractive or refractive multifocal embodiment.

In addition, an extended depth of focus feature may be added to, for example, a toric IOL, an IOL that modifies ocular spherical and/or chromatic aberration, and/or an accommodating IOL. In general, an extended depth of focus feature may be added to an IOL that modifies ocular aberrations.

Reading is often done in bright light conditions in which the pupil is small. In contrast, night-time driving is done in low light conditions in which the pupil is large. Embodiments of the present invention encompass lenses that relatively emphasize intermediate or near vision for small pupil sizes, while also relatively emphasizing far vision for large pupil sizes. In some such ophthalmic lenses, a greater proportion of light energy may be transmitted to the far focus from a peripheral portion of the lens to accommodate for low light, far viewing conditions such as night time driving, with the near or intermediate viewing receiving relatively more light energy from a central portion of the diffractive profile—for reading or computer work for example and/or to provide depth of focus and intermediate or near viewing under low light reading conditions as in for example reading restaurant menus.

FIG. 1A is a cross-sectional view of an eye E fit with a multifocal IOL 11. As shown, multifocal IOL 11 may, for example, comprise a bifocal IOL. Multifocal IOL 11 receives light from at least a portion of cornea 12 at the front of eye E and is generally centered about the optical axis of eye E. For ease of reference and clarity, FIGS. 1A and 1B do not disclose the refractive properties of other parts of the eye, such as the corneal surfaces. Only the refractive and/or diffractive properties of the multifocal IOL 11 are illustrated.

Each major face of lens 11, including the anterior (front) surface and posterior (back) surface, generally has a refractive profile, e.g. biconvex, plano-convex, plano-concave, meniscus, etc. The two surfaces together, in relation to the properties of the surrounding aqueous humor, cornea, and other optical components of the overall optical system, define the effects of the lens 11 on the imaging performance by eye E. Conventional, monofocal IOLs have a refractive power based on the refractive index of the material from which the lens is made, and also on the curvature or shape of the front and rear surfaces or faces of the lens.

In a young, healthy eye contraction and relaxation of ciliary muscles 17 surrounding the capsular bag 14 contribute to accommodation of the eye, the process by which the eye increases optical power to maintain focus on objects as they move closer. As a person ages, the degree of accommodation decreases and presbyopia, the diminished ability to focus on near objects, often results. A patient may therefore conventionally use corrective optics having two optical powers, one for near vision and one for far vision, as provided by multifocal IOL 11.

Multifocal lenses may optionally also make special use of the refractive properties of the lens. Such lenses generally include different powers in different regions of the lens so as to mitigate the effects of presbyopia. For example, as shown in FIG. 1A, a perimeter region of refractive multifocal lens 11 may have a power which is suitable for viewing at far viewing distances. The same refractive multifocal lens 11 may also include an inner region having a higher surface curvature and a generally higher overall power (sometimes referred to as a positive add power) suitable for viewing at near distances.

Figure 1B:
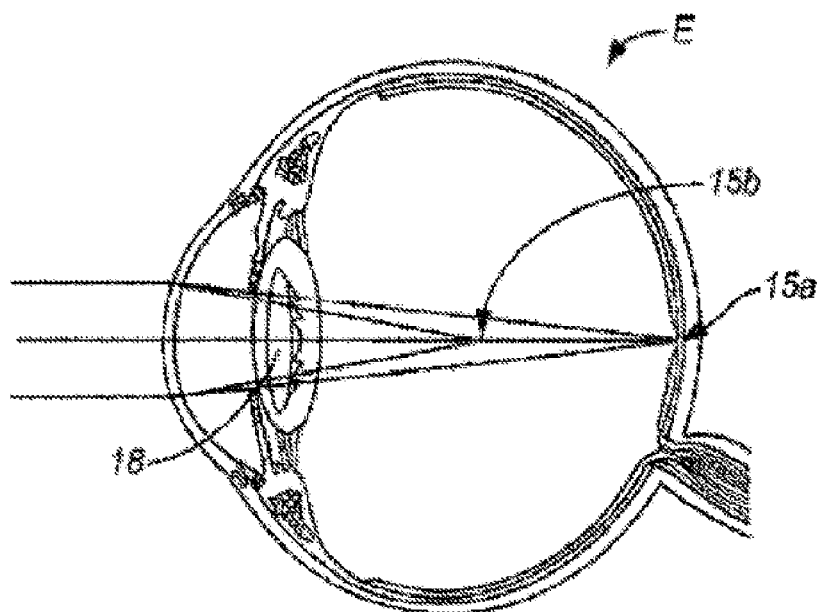
FIG. 1B is a cross-sectional view of an eye having an implanted multifocal diffractive intraocular lens.

Rather than relying entirely on the refractive properties of the lens, multifocal diffractive IOLs or contact lenses can also have a diffractive power, as illustrated by the IOL 18 shown in FIG. 1B. The diffractive power can, for example, comprise positive or negative add power, and that add power may be a significant (or even the primary) contributor to the overall optical power of the lens. The diffractive power is conferred by a plurality of concentric diffractive zones which form a diffractive profile. The diffractive profile may either be imposed on the anterior face or posterior face or both.

The diffractive profile of a diffractive multifocal lens directs incoming light into a number of diffraction orders. As light 13 enters from the front of the eye, the multifocal lens 18 directs light 13 to form a far field focus 15a on retina 16 for viewing distant objects and a near field focus 15b for viewing objects close to the eye. Depending on the distance from the source of light 13, the focus on retina 16 may be the near field focus 15b instead. Typically, far field focus 15a is associated with $0^{th}$ diffractive order and near field focus 15b is associated with the $1^{st}$ diffractive order, although other orders may be used as well.

Multifocal ophthalmic lens 18 typically distributes the majority of light energy into the two viewing orders, often with the goal of splitting imaging light energy about evenly (50%:50%), one viewing order corresponding to far vision and one viewing order corresponding to near vision, although typically, some fraction goes to non-viewing orders.

In some embodiments, corrective optics may be provided by phakic IOLs, which can be used to treat patients while leaving the natural lens in place. Phakic IOLs may be angle supported, iris supported, or sulcus supported. The phakic IOL can be placed over the natural crystalline lens or piggy-backed over another IOL. It is also envisioned that the present invention may be applied to inlays, onlays, accommodating IOLs, spectacles, and even laser vision correction.

Figure 2A:
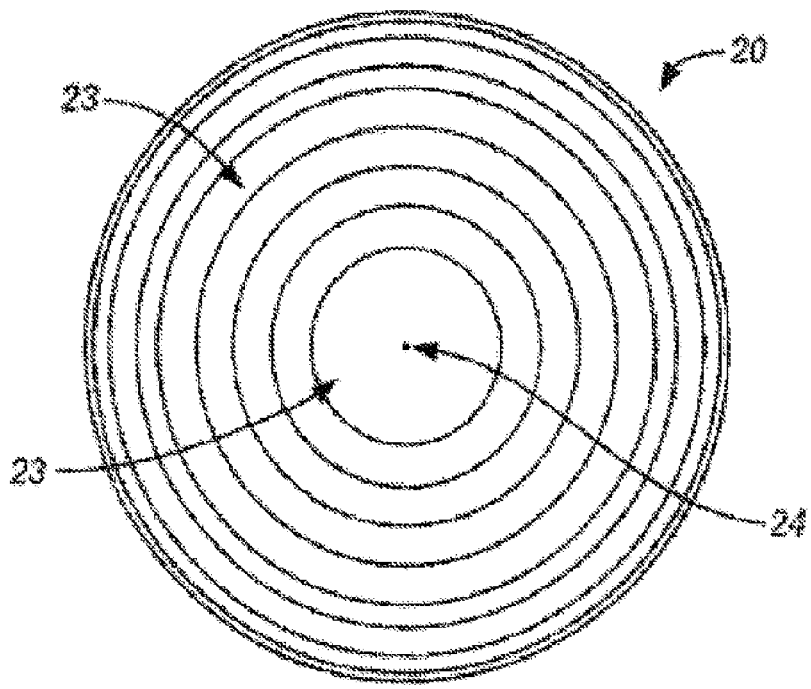
FIG. 2A is a front view of a diffractive multifocal ophthalmic lens.
Figure 2B:
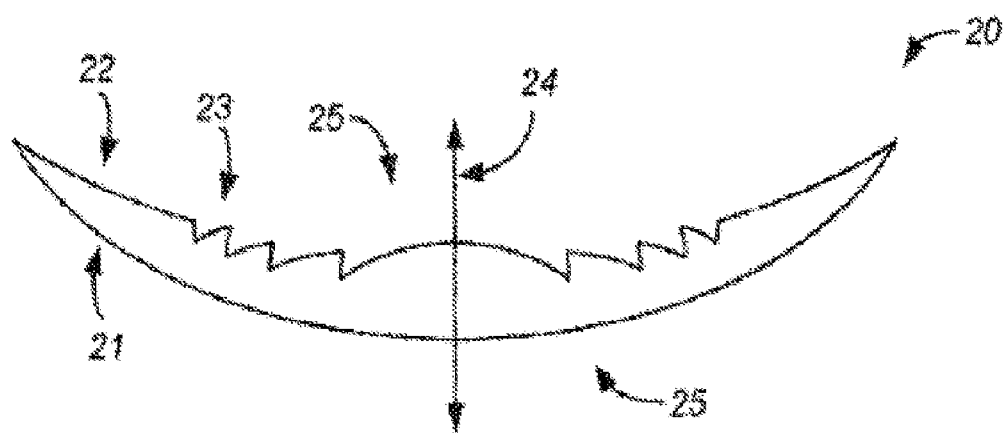
FIG. 2B is a cross-sectional view of the lens of FIG. 2A.

FIGS. 2A and 2B show aspects of a standard diffractive multifocal lens 20. Multifocal lens 20 may have certain optical properties that are generally similar to those of multifocal IOLs 11, 18 described above. Multifocal lens 20 has an anterior lens face 21 and a posterior lens face 22 disposed about optical axis 24. The faces 21, 22 of lens 20 typically define a clear aperture 25. As used herein, the term "clear aperture" means the opening of a lens or optic that restricts the extent of a bundle of light rays from a distant source that can be imaged or focused by the lens or optic. The clear aperture is usually circular and is specified by its diameter, and is sometimes equal to the full diameter of the optic.

When fitted onto the eye of a subject or patient, the optical axis of lens 20 is generally aligned with the optical axis of eye E. The curvature of lens 20 gives lens 20 an anterior refractive profile and a posterior refractive profile. Although a diffractive profile may also be imposed on either anterior face 21 and posterior face 22 or both, FIG. 2B shows posterior face 22 with a diffractive profile. The diffractive profile is characterized by a plurality of annular optical zones or echelettes 23 spaced about optical axis 24. While analytical optics theory generally assumes an infinite number of echelettes, a standard multifocal diffractive IOL typically has at least 9 echelettes, and may have over 30 echelettes. For the sake of clarity, FIG. 2B shows only 4 echelettes. Typically, an IOL is biconvex, or possibly plano-convex, or convex-concave, although an IOL could be plano-plano, or other refractive surface combinations.

Figure 3A:
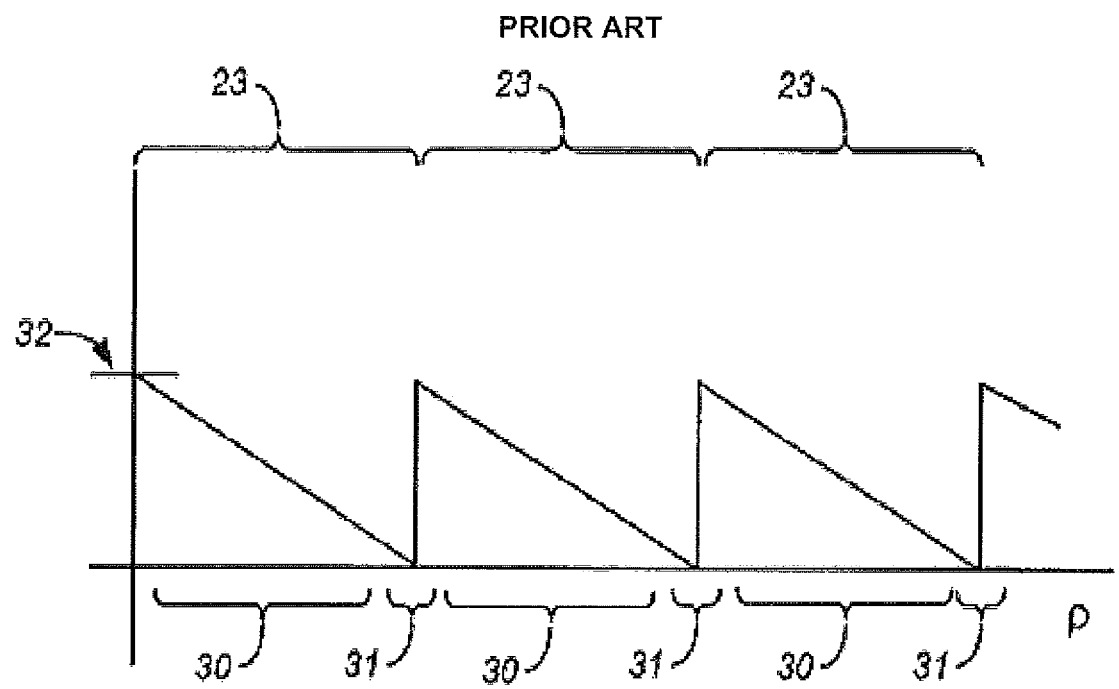
FIGS. 3A-3B are a graphical representations of a portion of the diffractive profile of a conventional diffractive multifocal lens.
Figure 3B:
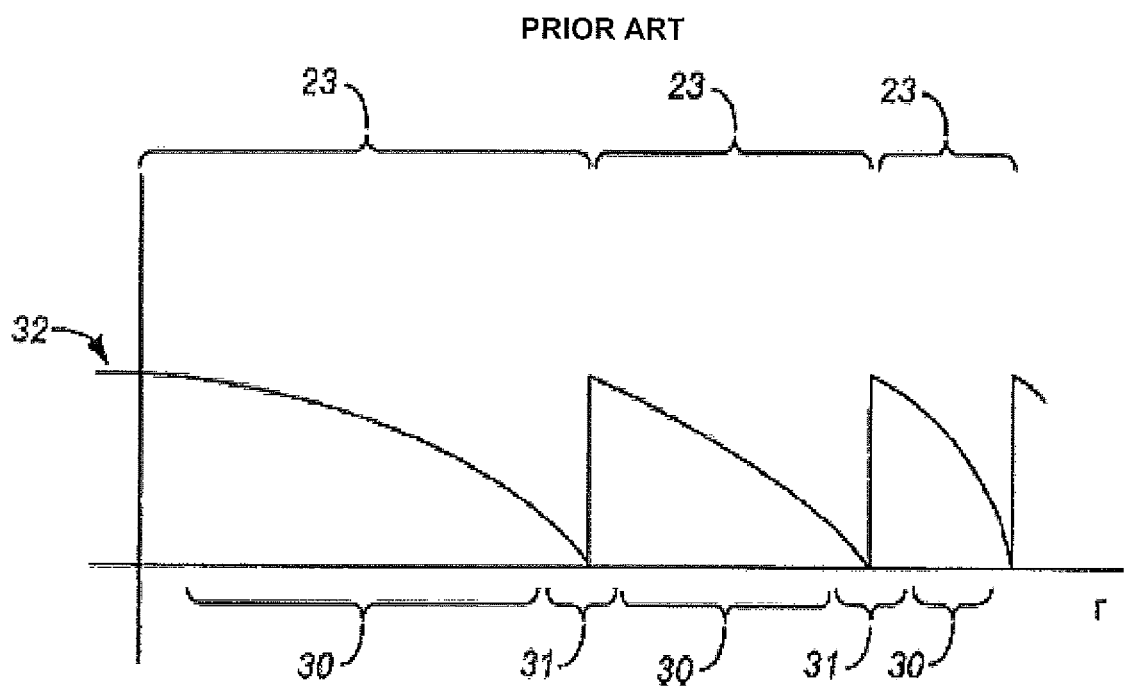

FIGS. 3A and 3B are graphical representations of a portion of a typical diffractive profile of a multifocal lens. While the graph shows only 3 full echelettes, typical diffractive lenses extend to at least 9 echelettes to over 32 echelettes. In FIG. 3A, the height of the surface relief profile (from a plane perpendicular to the light rays) of each point on the echelette surface is plotted against the square of the radial distance ($r^2$ or $\rho$) from the optical axis of the lens. In multifocal lenses, each echelette 23 may have a diameter or distance from the optical axis which is often proportional to $\sqrt{n}$, n being the number of the echelette 23 as counted from optical axis 24. Each echelette has a characteristic optical zone 30 and transition zone 31. Optical zone 30 has a shape or downward slope that may be linear when plotted against $\rho$ as shown in FIG. 3A. When plotted against radius r, optical zone 30 has a shape or downward slope that is parabolic as shown in FIG. 3B. As for the typical diffractive multifocal lens, as shown here, all echelettes have the same surface area. The area of echelettes 23 determines the add power of lens 20, and, as area and radii are correlated, the add power is also related to the radii of the echelettes.

As shown in FIGS. 3A and 3B, transition zone 31 between adjacent echelettes is sharp and discontinuous. The height of the lens face sharply transitions from sloping steadily downwards to stepping vertically upwards, and the transitions abruptly back to sloping steadily downwards again. In doing so, echelettes 23 also have a characteristic step height 32 defined by the distance between the lowest point and height point of the echelette. Hence, the slope (or first derivative) and/or the curvature (second derivative) of the diffractive surface are discontinuous adjacent the transitions.

Structure of Central Echelette

Figure 4:
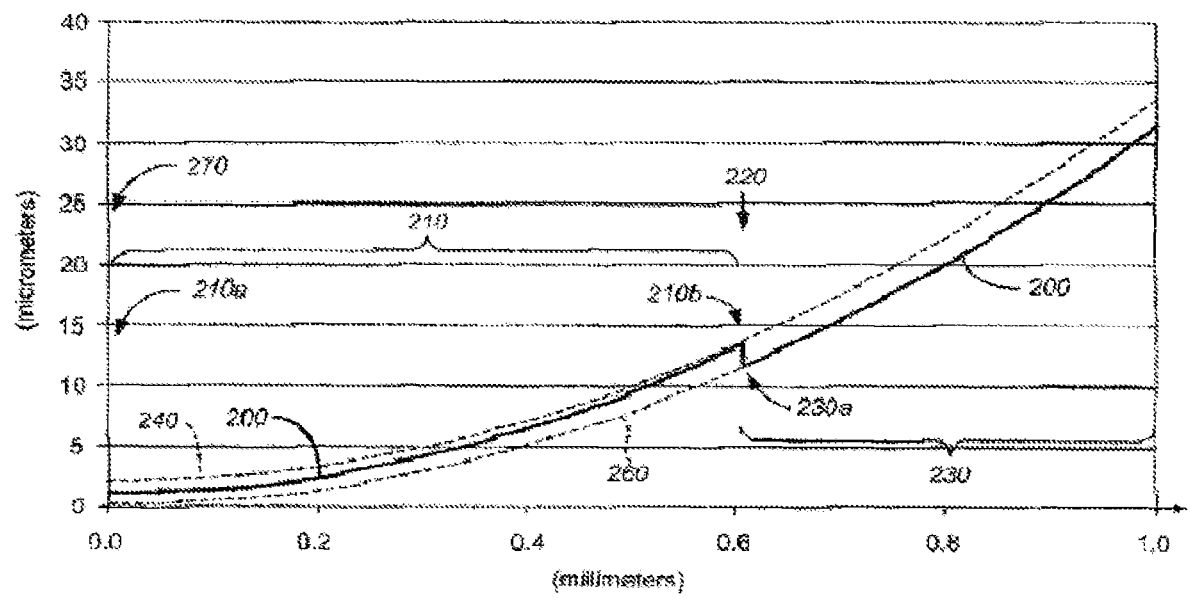
FIG. 4 shows aspects of the central echelette of a lens according to embodiments of the present invention.

FIG. 4 provides a graphical representation of a cross section of a portion of an exemplary lens illustrating the central echelette structure. The lens profile 200 has a ring diameter of 1.21 mm and a step height at 220 of 2.05 µm, corresponding with a phase delay of 0.5 lambda (see table 2). In this example, the ring diameter was reduced from 1.5 mm (which is the inner ring diameter for a 2.0 Diopter conventional IOL diffractive lens) to 1.21 mm by a scaling factor √2, as described in U.S. Pat. No. 5,121,980 (Cohen). Only the inner portion and part of the outer portion of half of the lens is shown, although since the lens is rotationally symmetric, the other half is a mirror image.

The adjacent echelette(s) in the outer portion (not shown) are detailed below. Profile 200 includes an inner portion 210 or single ring, a step or transition 220, and an outer portion 230. The outer portion 230 extends beyond that disclosed in FIG. 4F to 2.5 mm and may be comprised of limited additional echelettes. Inner portion 210 extends between a central location 210 of profile 200 and transition 220. Outer portion 230 extends between transition 220 and a peripheral location (not shown). In some cases, transition 220 can be disposed at a distance from the optical axis that is within a range from about 0.5 mm to about 2.0 mm, and peripheral location can be disposed at a distance from the optical axis that is within a range from about 2.0 to about 3.5 mm, or bigger (for example, for contact lenses, the ranges would be approximately 15% larger due to the optically more powerful position of contact lens compared to an IOL; those skilled in the art would appropriately scale certain dimensions depending on the application).

The inner portion or echelette 210 includes a center 210a and a peripheral edge 210b. At center or central section 210a of inner portion 210 where radial distance is zero, the sag (d) of inner portion is between the sag (d) of the diffractive base curve 240 and the sag (d) of the peripheral curve 260 at 1.03 µm from the peripheral curve 260, corresponding with a phase delay of 0.25 lambda (see table 2). At peripheral edge 210b, the sag (d) of inner portion 210 is substantially equivalent to the sag (d) of diffractive base curve 240 at 13.8 µm. The value of sag (d) between radial distance zero and radial distance at the peripheral edge 210b at 0.61 mm, gradually and smoothly changes from 1.03 µm (at r=0) to the value of the base curve 240 (at r=0.61 mm) which is 13.8 µm. This change occurs in a parabolic fashion. As shown here, inner portion can present a parabolic shape, for example as described in Equation 4a of Cohen, Applied Optics, 31:19, pp. 3750-3754 (1992), incorporated herein by reference.

At the peripheral edge 210b where the radial distance (r) is 0.61 mm, the value of sag (d) steps or changes from the value of diffractive base curve 240 to the value of peripheral curve 260. Where radial distance (r) corresponds to transition 220, sag (d) of inner portion is equivalent to the value of the diffractive base curve 240. Relatedly, the displacement of the profile approaches that of the diffractive base curve as the radial distance increases from a value of zero to a value of about 0.61 mm. The step height is 2.05 µm resulting in a phase delay of 0.5.

The outer portion 230 includes an inner or central edge 230a and a peripheral edge (not shown). At inner edge 230a, the sag (d) of outer portion is substantially equivalent to the sag (d) of peripheral curve 260. At peripheral edge, the sag (d) of outer portion remains substantially equivalent to the sag (d) of peripheral curve 260. As detailed below, a limited number of echelettes may be located between inner edge 230a and peripheral edge.

Figure 4A:
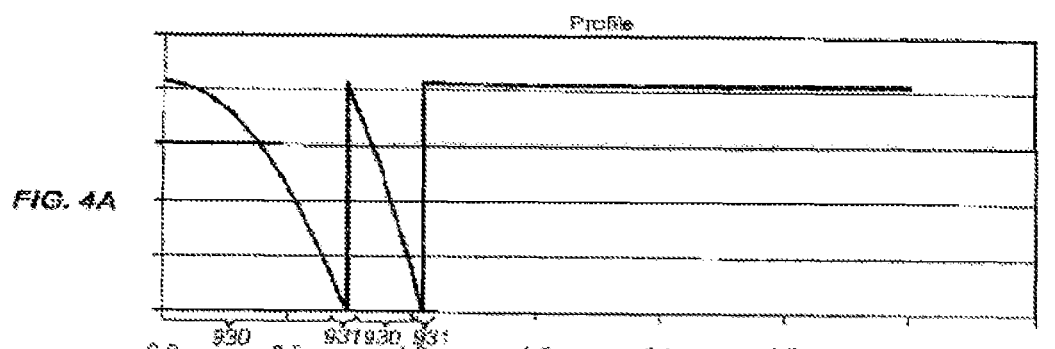
FIG. 4A-4E illustrates aspects of a lens profile according to embodiments of the present invention.

FIG. 4A provides a graphical representation of a portion of a lens diffractive profile with a central echelette and one peripheral adjacent echelette according to embodiments of the present invention. In FIG. 4A, the height of the surface relief profile (from a plane perpendicular to the light rays) of each point on the echelettes surface is plotted against the distance from the optical axis of the lens. The echelettes can have a characteristic optical zone 930 and transition zone 931. Optical zone 930 can have a shape or downward slope that may be linear when plotted against p as shown in FIG. 4A. When plotted against radius r, optical zone 930 can have a shape or downward slope that is parabolic. Central and peripheral echelettes can have a surface area that is between 1 and 7 mm². For example, the echelettes may have a surface area that is 2.3 mm². An outer (refractive) zone can follow the base radius with a fixed offset.

As shown in FIG. 4A, transition zones 931 between the optical zones 930 and the adjacent optical zones can be sharp and discontinuous. Similarly, a vertical transition between adjacent echelettes and also the peripheral portion or refractive zone can be sharp and discontinuous. The height of the lens face sharply transitions from sloping steadily downwards (e.g. across optical zones 930) to stepping vertically upwards (e.g. at transition zone 931), and the transitions abruptly back to sloping steadily downward or substantially horizontal at outer refractive zone. In doing so, echelette 930 also has a characteristic step height 932 defined by the distance between the lowest point and highest point of the echelette. Hence, the slope (or first derivative) and/or the curvature (second derivative) of the diffractive surface are discontinuous adjacent the transition. The first derivative can be indicated by the direction of the lines, and the second derivative can be indicated by the curve of the line.

According to some embodiments, light comes from below, in the direction indicated by arrow A, and only hits the echelettes 930 of the profile. According to some embodiments, in theoretical terms light does not hit the vertical connection of the optical zones, and hence the profile can be said to have no transition zone. According to some embodiments, in practice when one attempts to produce such a profile, for instance by lathe cutting, it may be difficult to reproduce the sharp corner (e.g. at where the optical zone connects with the adjacent optical zone) and hence the corner may be rounded to some extent due to the finite chisel radius. Such rounding may have a negligible effect on the optical performance. According to related embodiments, transition zone 931, which can be referred to as the transition from the echelette to the adjacent zone or zones, can be shaped in a specific way, so as to optimize the optical performance, for example to minimize scatter from a sharp transition.

Profile Parameters

The profile design can be characterized in terms of a set of parameters. For example, the limited echelette profile can be described as having a central echelette with a diameter and surface area, an adjacent echelette(s) with the same surface area, and an associated step height at each transition resulting in a phase delay. The central echelette may have a diameter within a range from about 1 mm to about 5 mm. For example, the central echelette may have a diameter of about 1.5 mm. Central echelette may have a surface area that is between 1 and 7 mm$^2$. For example, the central echelette may have a surface area that is 2.3 mm$^2$. The peripheral echelette(s) may have a surface area equal to the central echelette. In particular, Table 1 discloses the dimensions of the radius and diameter of the central echelette, along with the surface area of the central and peripheral echelettes.

| R (mm) | De (mm) | Area (mm$^2$) |
|--------|---------|---------------|
| 1.48   | 3       | 6.9           |
| 1.05   | 2.1     | 3.5           |
| 0.86   | 1.7     | 2.3           |
| 0.74   | 1.5     | 1.7           |
| 0.66   | 1.3     | 1.4           |
| 0.61   | 1.2     | 1.2           |

The step height or profile height can determine the phase delay or phase shifting profile. A greater step height can correspond to a greater phase shift. According to some embodiments, a lens can include a transition characterized by a step height producing a phase shift between about 0.25 and about 1 times the design wavelength. In some cases, a diffractive profile can be characterized by a design wavelength, and the lens can include a transition characterized by a step height producing a phase shift between about 0.15 and about 2 times the design wavelength. According to some embodiments the lens may include a transition characterized by a step height producing a phase shift of about 0.5. In other embodiments, the lens may include a transition characterized by a step height of about 0.4.

Table 2 provides dimensions of various samples disclosing the relationship between phase delay (in wavelengths) and step height (in μm), as valid for an example IOL material.

TABLE 2

| Phase Delay | Step height |
|-------------|-------------|
| 0.896       | 3.68        |
| 0.700       | 2.87        |
| 0.590       | 2.42        |
| 0.509       | 2.09        |
| 0.500       | 2.05        |
| 0.423       | 1.74        |
| 0.366       | 1.50        |
| 0.350       | 1.44        |
| 0.250       | 1.03        |
| 0.150       | 0.62        |

Figure 4B:
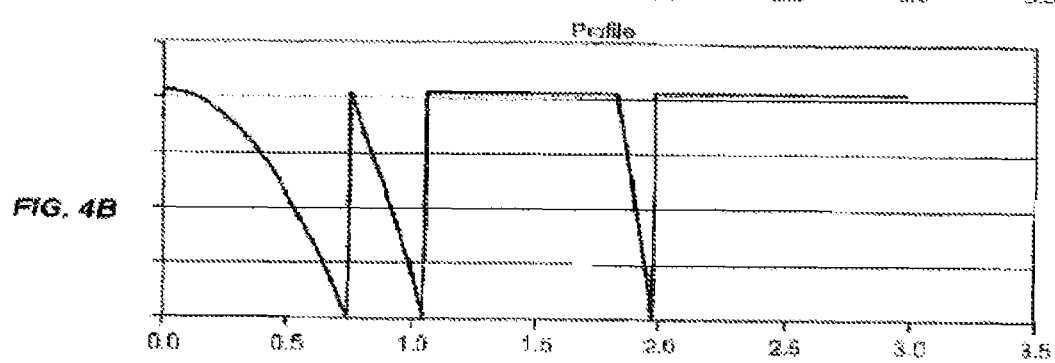

FIG. 4B provides a graphical representation of a portion of a lens diffractive profile with a central echelette and two peripheral echelettes according to embodiments of the present invention. The height of the surface relief profile (from a plane perpendicular to the light rays) of each point on the echelettes surface is plotted against the distance from the optical axis of the lens. According to some embodiments, a lens with a central and peripheral adjacent echelette, as disclosed in FIG. 4A may also be comprised of an additional peripheral echelette with a refractive region between the outermost echelette and the interior echelettes.

Figure 4C:
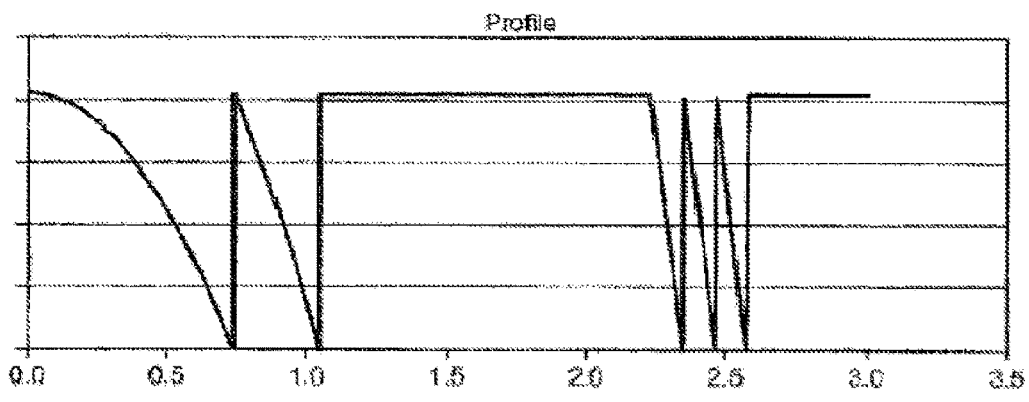

FIG. 4C also details a portion of a lens diffractive profile with a central echelette and two peripheral echelettes. In this embodiment, however, the refractive zone is immediately adjacent to the central echelette and separates the central echelette from three peripheral and adjacent echelettes.

Figure 4D:
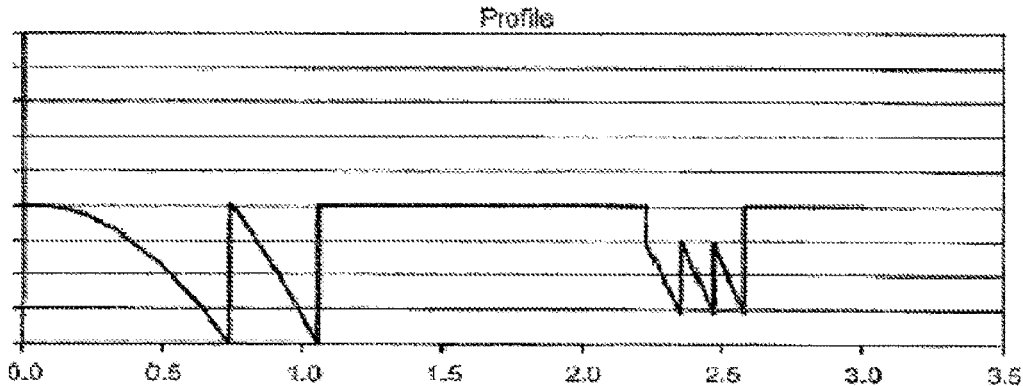

Although the above preferred embodiments disclose lenses with echelettes that have equal step heights, preferred embodiments herein also include lenses with echelettes with varying step heights as detailed in, for example, FIG. 4D. FIG. 4D. discloses a four echelette embodiment wherein a refractive region separates the central and adjacent echelette from three peripheral adjacent echelettes. As seen in FIG. 4D, the step height (defined by the distance between the lowest point and highest point of the echelette) of the three outer echelettes is less than the step height of the inner echelettes. Of course, in addition to covering embodiments where the step height of the outer echelette(s) is less than the inner echelette(s), the step height of the inner echelette(s) may be less than the outer echelette(s). In addition, for embodiments with multiple central rings, the central rings may have gradually changing step heights. It is further envisioned that the rings in the periphery may also have gradually changing step heights. It is also foreseeable that the step heights may increase, decrease, or alternate.

Figure 4E:
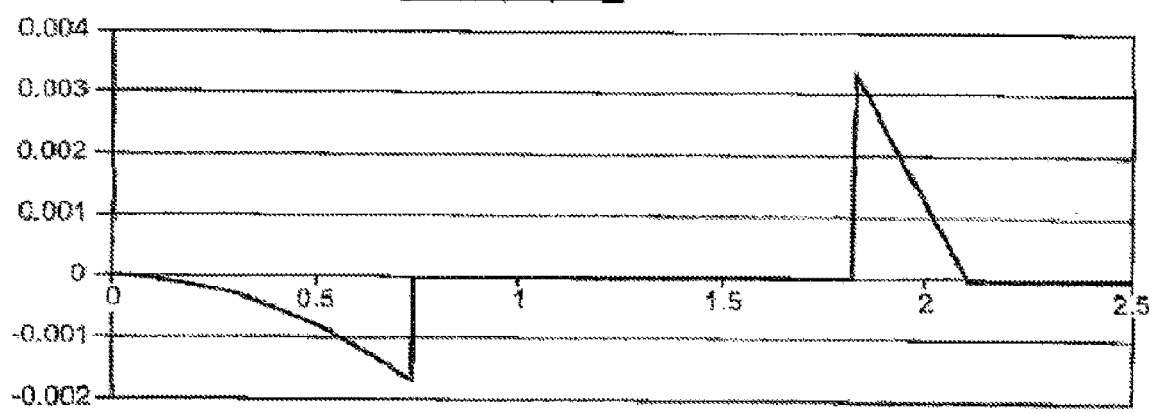

FIG. 4E provides a graphical representation of a portion of a lens diffractive profile with a central echelette and a peripheral echelette which is not adjacent to the central echelette. The central echelette may have a shape or downward slope that is parabolic. A refractive region may then separate the central echelette from the peripheral echelette. The peripheral echelette may then be characterized by a sharp and discontinuous step height followed by a downward slope. As in the embodiments above, a peripheral refractive region may surround the outermost echelette. Additionally, other exemplary embodiments include non-adjacent echelette variations analogous to FIG. 4A-4D. By way of non-limiting example, two echelettes that are not separated by a refractive region may also be non-adjacent.

Pupil Dependence

The size of the human pupil varies with illumination. In bright light the pupil is small, and in dim or low light conditions the pupil is large. In addition, the size of the human pupil varies with accommodative effort. Without accommodative effort, the pupil is larger than with accommodative effort. Hence, for a smaller pupil, it may be desirable to provide a design that places a relative emphasis on intermediate or near vision. For a larger pupil, it may be desirable to provide a design that places a relative emphasis on far vision.

In typical reading or near vision conditions where the light is bright, the size of the pupil is small, e.g. between about 1 mm and 2 mm in diameter, and the eye has a large depth of focus (for example from a pinhole effect), almost irrespective of the optics of the IOL. When the size of the pupil is large, e.g. larger than about 4-5 mm in diameter, the situation generally applies to low light conditions, and is often associated with distance vision for which the power of the IOL is typically established. Therefore, many patients would benefit most from an IOL that enhances the depth of focus in order to view at intermediate distances. An IOL having a central echelette with limited adjacent echelettes may effectively increase the depth of focus for intermediate pupil sizes, while maintaining the general increased depth of focus of small pupil sizes, and also maintaining an emphasis on far vision for large pupil sizes.

At the same time, since the limited echelettes and the remaining surface area of the optic or remaining lens portion ("non-echelette") have unequal surface areas for almost all pupil sizes, there is an incomplete split between the foci. The condition of dysphotopsia (e.g. halos) that is present for multifocal lenses is observed to be dominated by separation of two foci and pupil size effects. Accordingly, pursuant to exemplary embodiments of the present invention, the lens may include only a limited number of echelettes, so that light separation between distinct foci is not complete, as compared to standard diffractive multifocal IOLs. Since the split of light is incomplete, the separation of foci is incomplete. The incomplete separation of foci contributes to the extended depth of focus and the attenuation of dysphotopsia (e.g. halos).

In an exemplary embodiment, the limited echelette design has an optical performance that depends on the pupil size. For very small pupils, where the pupil is smaller than the size of the central and adjacent echelette(s), the echelette will act as a refractive lens, having a very large depth of focus due to the pinhole effect. For medium and higher pupil sizes, where the pupil covers the central echelette and the adjacent echelette, the lens will act as a diffractive/refractive lens, directing the light to several foci. For higher pupil sizes, more light is being directed to the lower order foci. The size of the central and adjacent echelette(s) influences the pupil dependence of the lens. As such, the size of the central and adjacent echelette(s) can be chosen, depending on the pupil sizes of a specific patient. For example, the pupil sizes of a patient may be measured in bright light, in dim light, during far vision and during near vision, and in the different combinations of light level and accommodative effort. These different pupil sizes, which may be defined as pupil dynamics, can be used as input parameters for an optimal design of the limited echelette design.

For example, if a patient has a pupil diameter during near vision (e.g. viewing target at close distance, with high accommodative effort) smaller than 2 mm, having this pupil dimension with both bright and dim light, then the size of the central and adjacent echelette(s) may be selected to be smaller than 2 mm (e.g. outer diameter of the adjacent echelette of FIG. 4A), as to provide adequate near and intermediate vision. Relatedly, if a patient has a pupil diameter during near vision larger than 2 mm, having this pupil dimension with both bright and dim light, then the size of the central and adjacent echelette(s) may be 2 mm or larger, as to provide adequate near and intermediate vision. In general, the diameter of the central and adjacent echelette(s) can be smaller than the smallest pupil size the patient has under any condition (e.g. bright/dim light; near/far vision). For any type of pupil dynamics, the size, the profile, and the offsets may be chosen to maximize the lens performance for that specific patient, or group of patients. Generally, this is a trade off between the different vision circumstances (combinations of light level and accommodative effort) at which the pupil of the patient is measured. Accordingly, exemplary embodiments include a method of designing ophthalmic lens comprised of utilizing pupil size measurements and based on the measurements determining the size of an isolated echelette to impose on the surface of a lens. The pupil size measurements may be based on a group of patients.

Evaluation of Variations of a Specific Example

Figure 5:
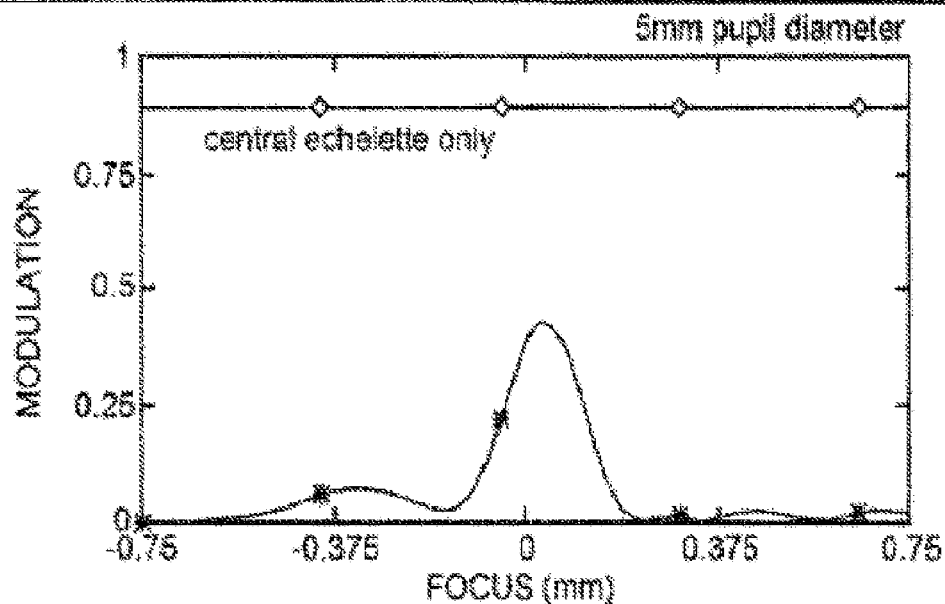
FIG. 5 shows aspects of calculated defocus curves according to a central echelette embodiment.
Figure 6:
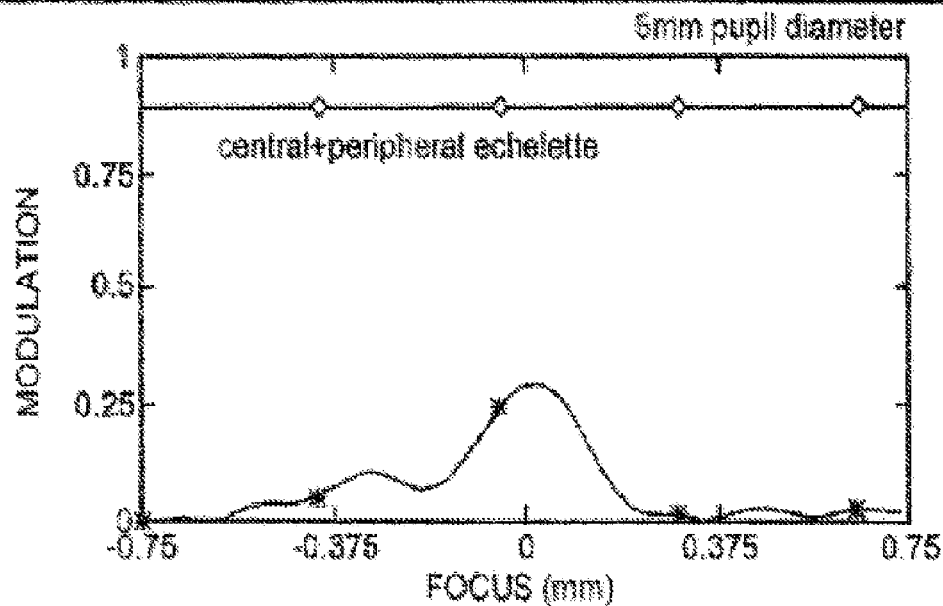
FIG. 6 shows aspects of calculated defocus curves according to a embodiments of the present invention.

FIGS. 5 and 6 show calculated defocus curves in the ACE eye model of an embodiment with a central ring diameter of 1.48 mm, an echelette surface area of 1.7 mm$^2$, and a phase delay of 0.4 wavelength. The horizontal axis denotes the defocus value in the image plane, in millimeters. Negative defocus values represent the myopic eye, and therefore, simulate vision at intermediate and near distances. The vertical axis denotes the modulus (MTF) at 50 cycles per millimeter. Data for 5 mm pupil diameters is included. FIG. 5 shows the defocus curve for an embodiment having only a single central echelette. FIG. 6 shows an exemplary embodiment as disclosed in section 4E, having, in addition to the central echelette, a peripheral echelette. The peripheral echelette and has a surface area of 3.5 mm$^2$, and a phase delay of 0.82 wavelength. The MTF at intermediate vision distances, with defocus values of about −0.2 mm to −0.3 mm, as shown in FIG. 6 is higher than the MTF at corresponding defocus values in FIG. 5. As illustrated in the figures, a central plus peripheral echelette increases the depth of focus as compared to a central echelette only.

Embodiments of the present invention may be combined with a multifocal lens design, and with that extend the depth of focus of each focus of the multifocal lens. Similarly, embodiments of the present invention may be combined with an accommodating lens design, by which the range of accommodation of the accommodating lens can be extended. In addition, embodiments of the present invention may be combined with lenses correcting ocular aberrations, like toric lenses, aspherical lenses, lenses correcting chromatic aberrations, and the like.

Embodiments of the present invention may be combined with a lens design correcting chromatic aberrations. In one embodiment, the phase delay of the echelettes in the preceding examples is increased by a discrete multiple of wavelengths, in order to correct for chromatic aberration. For example, if a phase delay of 0.5 was used, corresponding to a step height of 2.05 µm, an alternative embodiment would have a phase delay of 1.5, corresponding to a step height of 6.15 µm. This embodiment directs the first order diffraction to the far focus, and the second order diffraction establishes the depth of focus at the intermediate and near range.

Further Aspects of Multi-Ring Lenses for Extended Depth of Focus

Embodiments of the present invention encompass ophthalmic lenses having an aspheric anterior surface and a diffractive posterior surface, which provide extended depth of focus and compensate for natural chromatic and spherical aberration produced by the eye. Although many of the examples provided herein describe a diffractive profile disposed at the posterior of an ophthalmic lens, it is understood that a diffractive profile can also be disposed at the anterior lens surface, or in some cases at both anterior and posterior surfaces, with similar results. Similarly, although many of the examples provided herein describe an aspherical anterior surface, it is understood that an aspherical profile can also be disposed at the posterior lens surface, or in some cases at both anterior and posterior surface, with similar results.

Exemplary ophthalmic lenses include contact lenses, phakic lenses, pseudophakic lenses, corneal inlays, and the like.

Figure 7:
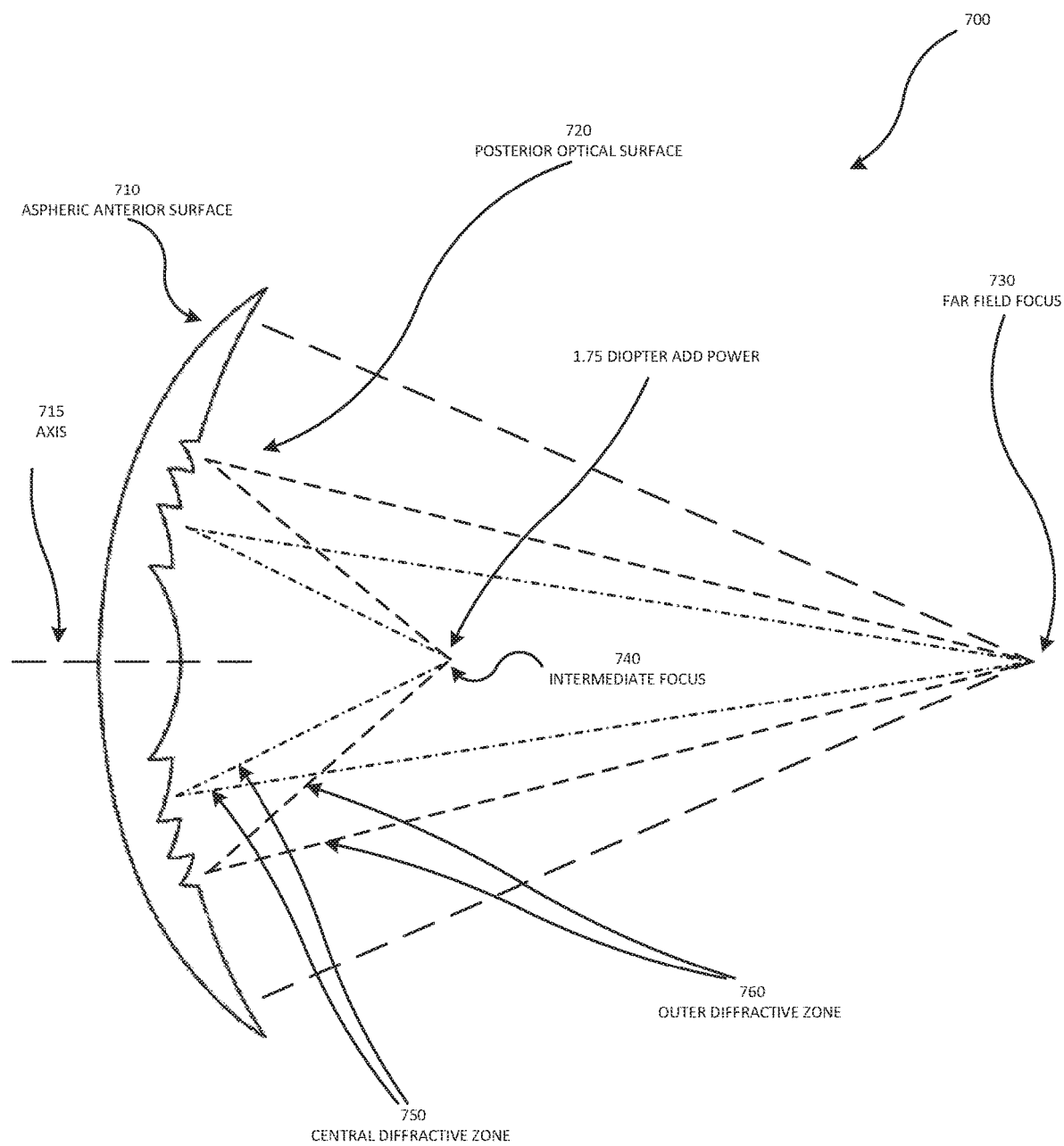
FIGS. 7 and 7-1 depict aspects of ophthalmic lenses according to embodiments of the present invention.

FIG. 7 depicts an exemplary ophthalmic lens 700 having an anterior surface 710 and a posterior surface 720. Each of the anterior and posterior surfaces are disposed about an optical axis 715. The anterior surface can incorporate an aspheric shape, and the posterior surface can incorporate a diffractive shape. In some instances, lens 700 may have a bi-convex configuration (e.g. FIG. 7-1), where each of the anterior and posterior surfaces presents a generally convex shape or profile. The anterior surface 710 can include an aspheric shape that extends across the entire front of the lens. Hence, an aspheric anterior surface 710 may include a full anterior surface that is refractive. Similarly, the posterior surface 720 can include a diffractive profile that extends across the entire back of the lens. Hence, the posterior optical surface 720 may include a diffractive profile that extends across the entire posterior surface. The anterior surface 710 operates to refractively direct light toward the far field focus 730. In this way, the far focus 730 may correspond to a refractive aspect of the lens 700. The posterior surface operates to diffractively direct light toward the far field focus 730 and the intermediate focus 740. In this way, each of the far focus 730 and the intermediate focus 740 may correspond to a diffractive aspect of the lens. An aspheric shape can provide a means for fully or at least partially compensating for or treating natural spherical aberration which may be produced by the eye (e.g. ocular spherical aberration or corneal spherical aberration). The diffractive profile can provide a means for fully or at least partially compensating for or treating natural chromatic aberration which may be produced by the eye (e.g. ocular chromatic aberration). In some instances, the means for compensating for ocular chromatic aberration and the means for compensating for ocular spherical aberration, when combined, provide a far focus corresponding to a base power and an intermediate focus corresponding to an add power. The difference between the base power and the add power can define an extended depth of focus for the lens.

The far field focus 730 may correspond to a base power of the lens, and the intermediate focus 740 may correspond to an add power of the lens. In some cases, the far focus 730 corresponds to a first diffractive order of the diffractive profile. Optionally, the far focus 730 may correspond to a second diffractive order of the diffractive profile. Similarly, the far focus may correspond to a third diffractive order of the diffractive profile. Often, the intermediate focus 740 corresponds to a diffractive order (e.g. $2^{nd}$) of the diffractive profile that is higher than the diffractive order (e.g. $1^{st}$) corresponding to the far focus 730. The base power value for the lens may vary depending on the type of lens. Similarly, the add power for the lens may vary depending on the type of lens. For an intraocular lens, the base power value may be within a range between 5 to 34 Diopters, or even wider. For a contact lens, the base power value may be within a range between −10 to +5 Diopters or even wider. For an exemplary intraocular lens, the base power can be 20 Diopters, and the add power can be 1.75 Diopters. It is understood that other similar add powers corresponding to the intermediate focus can be used. Such an add power is substantially lower than many current multifocal intraocular lenses, which often provide an add power in the range from 3.0 to 4.0 Diopters. For an exemplary contact lens, the add power may be about 1.3 Diopters.

As shown here, the diffractive profile includes a central diffractive zone 750 and an outer or peripheral diffractive zone 760. The central zone 750 encompasses two inner echelettes, or rings, having diameters of 1.6 mm and 2.2 respectively. The central zone 750 operates to direct 41% of incident or incoming light to far field focus 730, and 41% of incident or incoming light to intermediate focus 740. In this sense, the central zone 750 can be said to provide a light distribution between far and intermediate of 50:50%. That is, the percentage of light directed to each of the far and intermediate focus points is 50% of the sum of the light distributed between the far focus and intermediate focus (i.e. 41/(41+41)=50%). It is understood that other diffractive profile central zones providing different light distributions may be used.

The peripheral zone 760 operates to direct 63% of incident or incoming light to far field focus 730, and 21% of incident or incoming light to intermediate focus 740. In this sense, the peripheral zone 760 can be said to provide a light distribution between far and intermediate of 75:25%. That is, the percentage of light directed to the far focus is 75% of the sum of the light distributed to the far focus and intermediate focus (i.e. 63/(63+21)=75%), and the percentage of light directed to the intermediate focus is 25% of the sum of the light distributed between the far focus and intermediate focus (i.e. 21/(63+21)=25%). It is understood that other diffractive profile peripheral zones providing different light distributions may be used.

In this way, the diffractive optical element includes multiple zones, where each zone acts to concentrate or direct incident light in specific directions according to specific diffractive orders. In some instances, about 16% to 18% of the light is lost to spurious diffractive orders. According to some embodiments, the zeroth order is not used for vision treatment purposes.

Figure 12A:
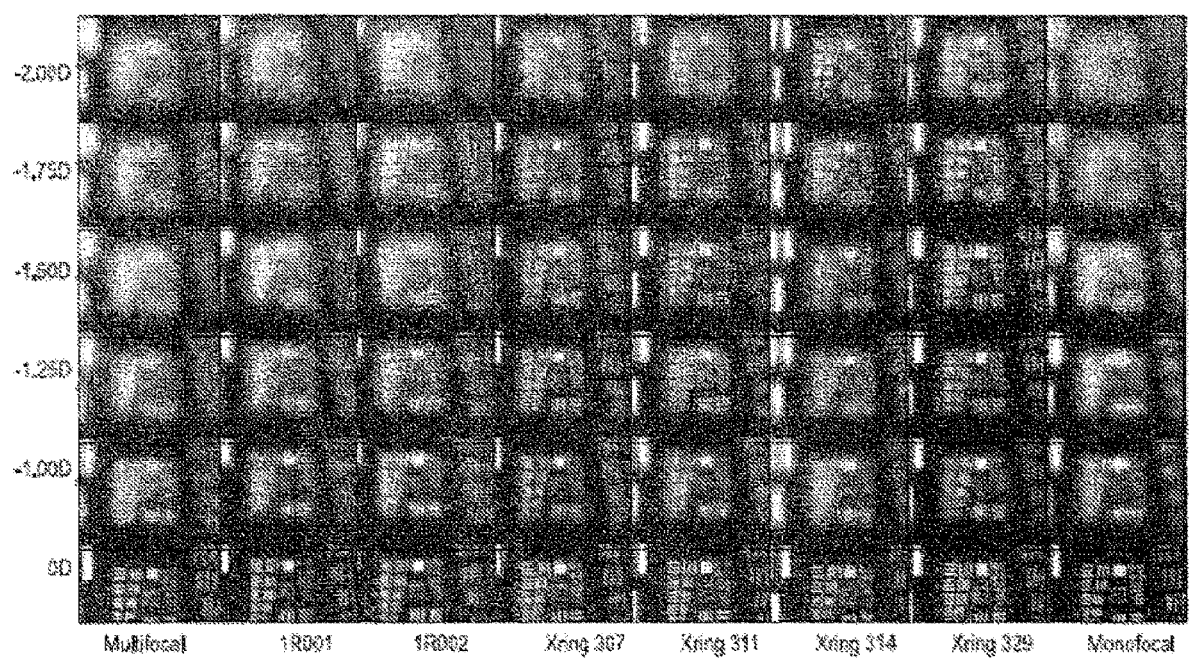
FIGS. 12A and 12B depict aspects of ophthalmic lenses according to embodiments of the present invention.
Figure 12B:
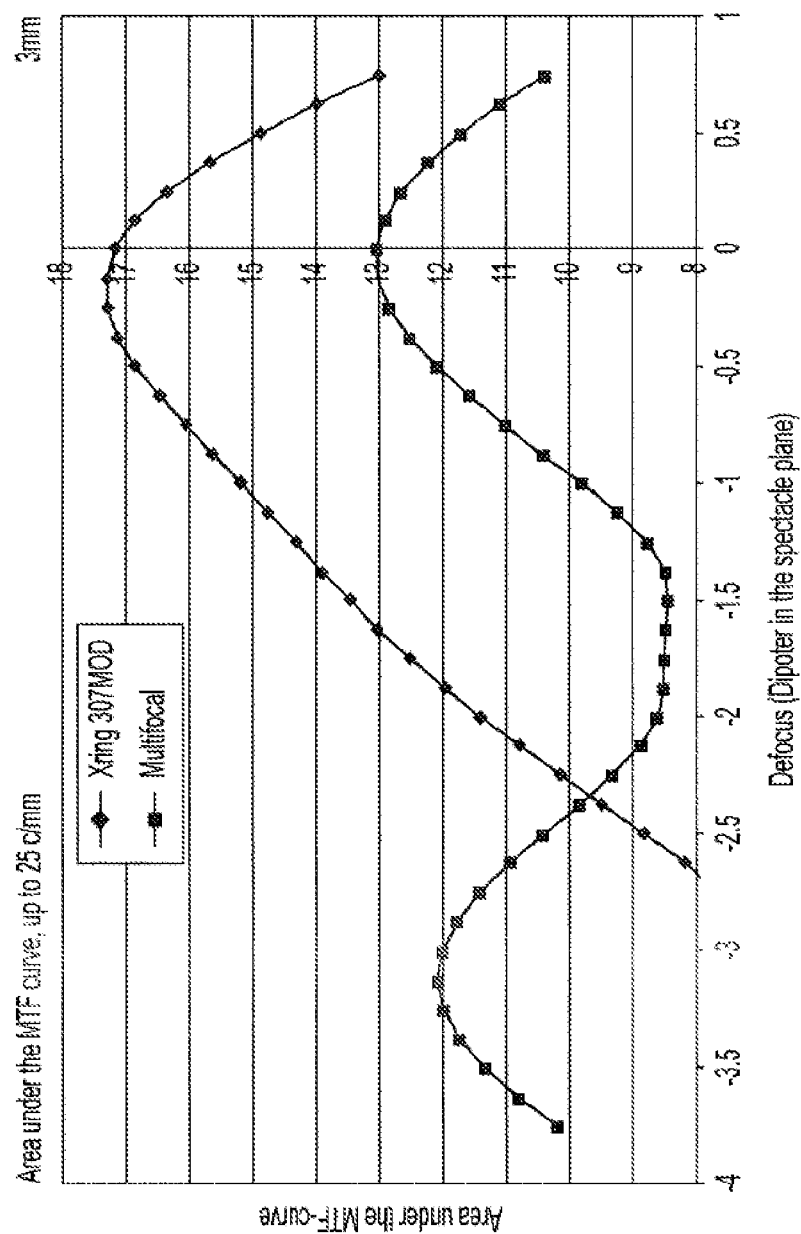

The lens 700 provides an extended depth of focus to an eye of a patient. For example, the lens can bring faraway objects and objects at intermediate distances into focus for the patient simultaneously. When the lens is administered to the patient, the patient will not perceive two distinct focal images (e.g. two images corresponding to far and intermediate focus, respectively), but rather will experience a true extended depth of focus, with a constant or gradual decrease in visual quality when objects become closer to the eye. FIGS. 12A, 12B, and 13, discussed elsewhere herein, demonstrate how exemplary lens designs can improve optical quality across an extended depth of focus.

By combining an aspheric anterior surface that corrects for spherical aberration, and posterior diffractive surface that corrects for chromatic aberration, lenses as disclosed herein provide excellent contrast properties in addition to an extended depth of focus. For example, the diffractive surface combined with the aspheric surface can correct or reduce chromatic aberration produced by the eye at various foci.

It is understood that in some embodiments, correction or treatment of chromatic aberration can also be achieved by providing a lens containing a combination of two materials having different dispersion characteristics, for example as described by Bradley et al. "Achromatizing the human eye" Optom. Vis. Sci. 68, 608-16 (1991), the content of which is incorporated herein by reference. For example, lens design can use pairings of materials that have the same refractive index at some intermediate wavelength, e.g., 588 nm, but different amounts of chromatic dispersion to create lenses with zero power at 588 nm but with opposite power at wavelengths above and below 588 nm. An alternative embodiment of the present invention involves the correction of chromatic aberration using two materials having different dispersion characteristics, in combination with an aspherical refractive surface and diffractive rings to extend the depth of focus.

Embodiments of the present invention encompass ophthalmic lenses and lens prescriptions, as well as systems and methods for producing such lenses and prescriptions. Exemplary lenses include lens surfaces, disposed about an optical axis, which provide aspheric and diffractive profiles. The aspheric profile can direct light toward a far focus, and the diffractive profile includes (i) a central zone that distributes a first percentage of light toward a diffractive order at the far focus and a second percentage of light toward another diffractive order at an intermediate focus disposed anterior to the far focus, and (ii) a peripheral zone, surrounding the central zone, that distributes a first percentage of light toward the diffractive order at the far focus and a second percentage of light toward the other diffractive order at the intermediate focus. In some instances, the aspheric profile is provided by an anterior face of the lens. In some cases, the diffractive profile is provided by the posterior face of the lens.

As noted elsewhere herein, different diffractive zones can provide different light distributions to different focus points (e.g. between far and intermediate). Table 3 provides an illustrative example.

TABLE 3

| Zone | Far ($1^{st}$ diffractive order) | Intermediate ($2^{nd}$ diffractive order) | Distribution (Far:Intermediate) |
| --- | --- | --- | --- |
| Central | 41% | 41% | 50:50 |
| Peripheral | 63% | 21% | 75:25 |

As noted elsewhere herein, the intermediate focus corresponds to the add power. Hence, lens designs such as those represented by Table 3 are different than currently known lens designs which the entirety of the lens directs 50% of the light toward the add power. Such known lens designs may not sufficiently correct or treat chromatic aberration in the far focus. Further, such known lens designs have an add power that is substantially larger than that provided by embodiments of the present invention. In some instances of the present invention, exemplary lens designs include a peripheral zone which directs 25% of the distributed light toward the add power. What is more, because lens designs according to embodiments of the present invention may provide a diffractive profile across the entire lens or a substantial portion thereof, such lenses are different than currently known lens designs which do not provide a diffractive profile or diffractive effect at large pupil sizes.

Figures 1, 7:
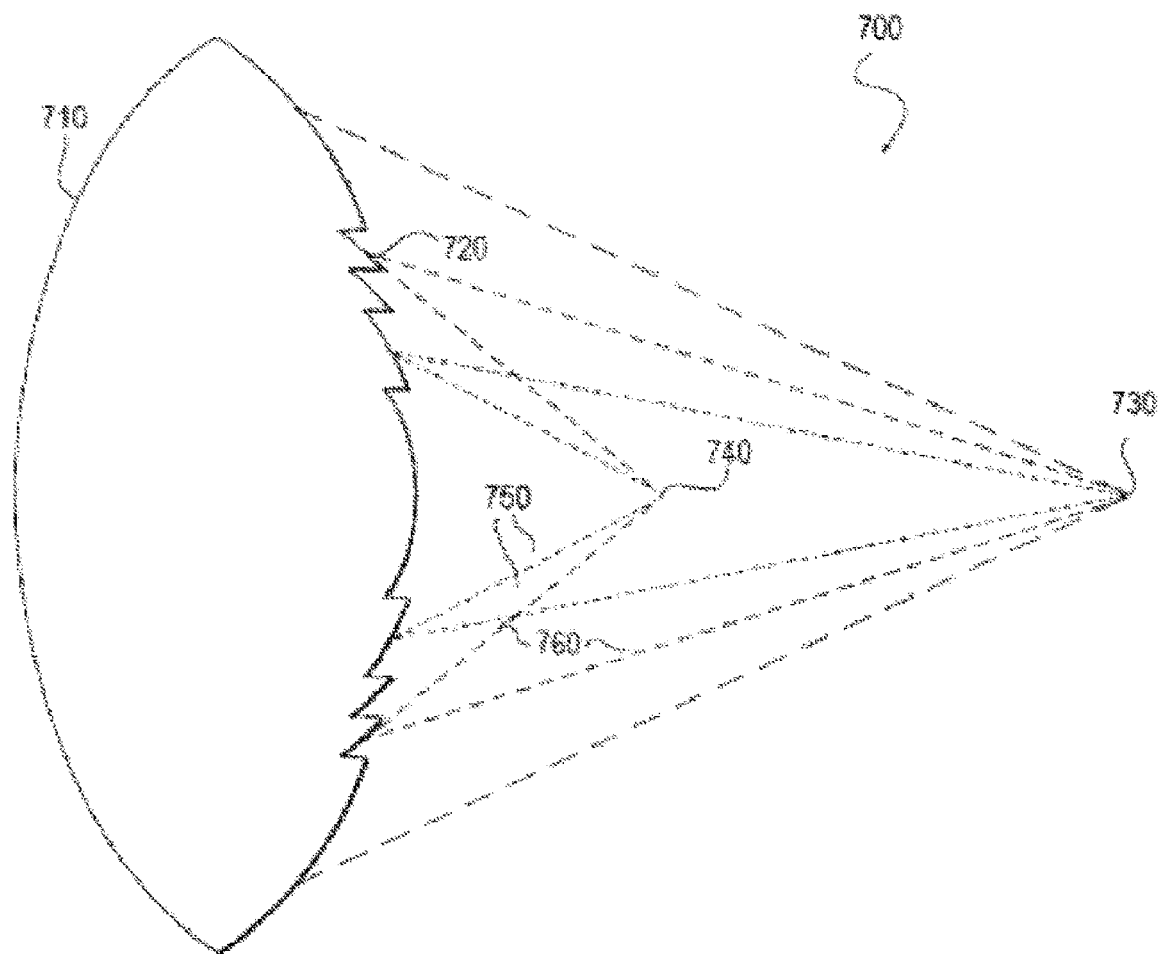
Figure 8:
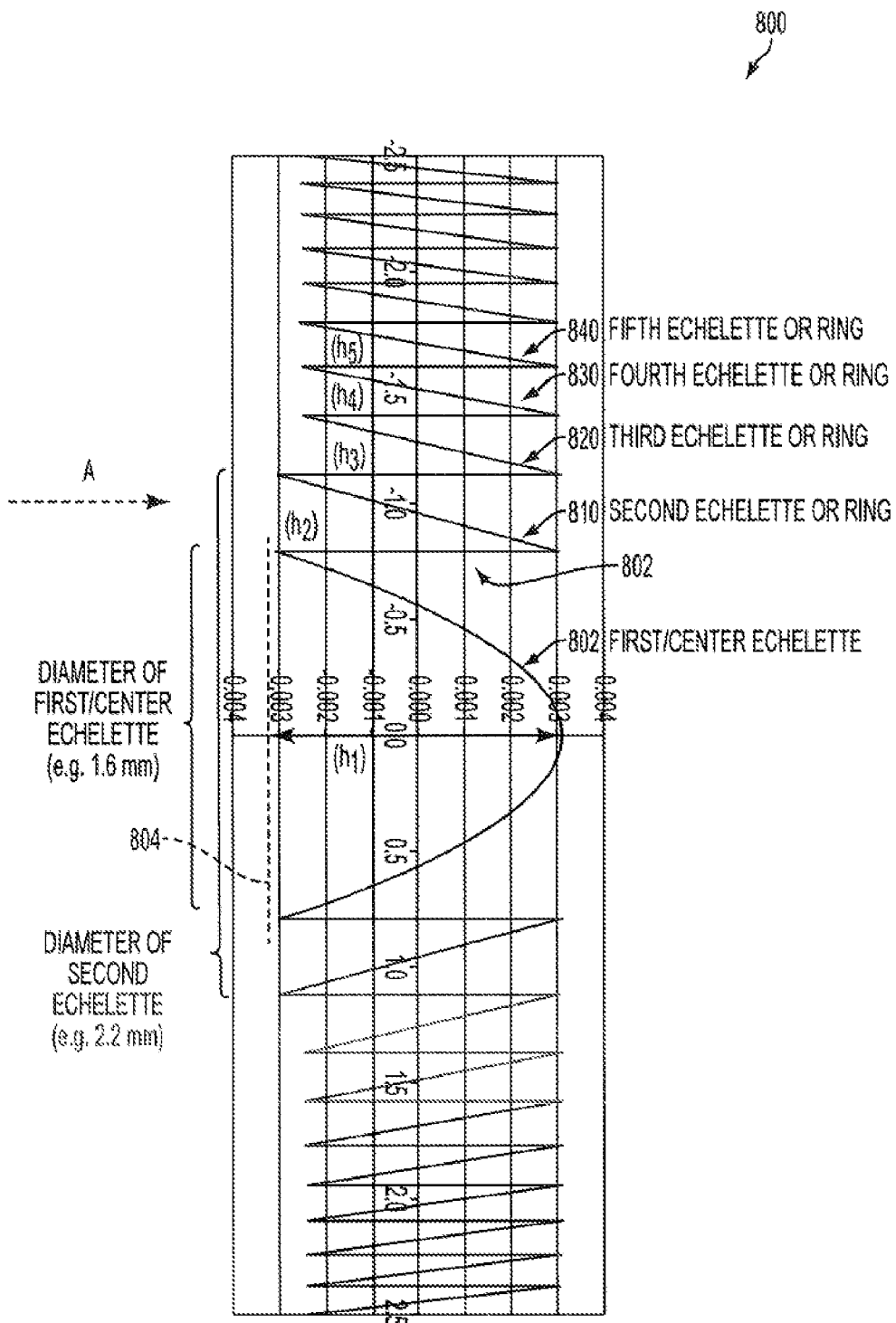
Figures 1, 8:
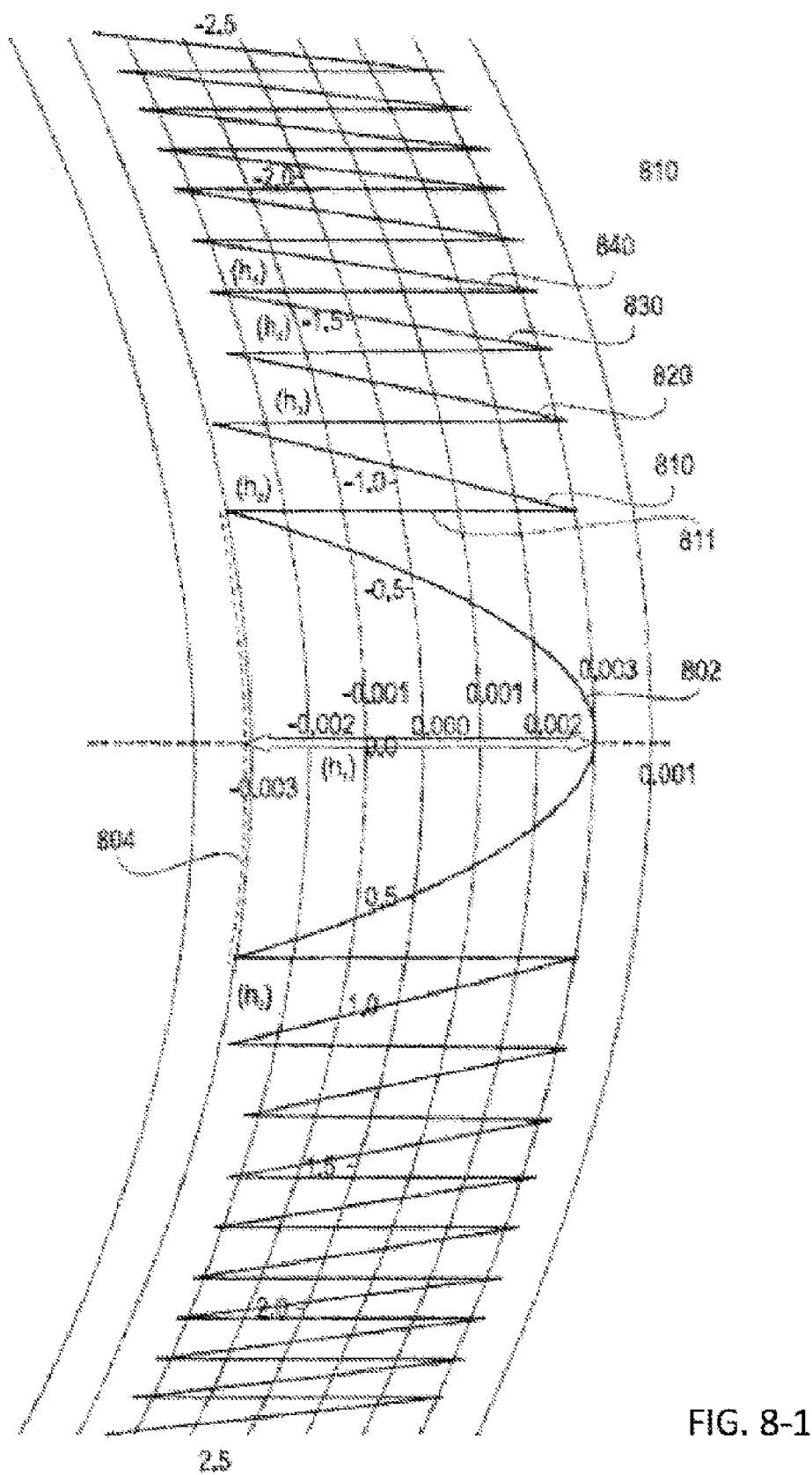

FIG. 8 illustrates aspects of a diffractive profile 800 of an ophthalmic lens according to embodiments of the present invention. As shown here, a center portion or (first) echelette 802 of the diffractive profile has a height ($h_1$) relative to a base shape or curvature 804 of the profile. A second echelette 810 is disposed peripherally adjacent to the first echelette 802, with a first transition zone 811 disposed therebetween. The transition zone 811 can be characterized by a step height ($h_2$). Hence, each echelette can have a characteristic height or step height, for example as defined by the distance between the inner (or central), highest point of the echelette (e.g. as measured relative to the base shape), and the outer (or peripheral), lowest point of the echelette (e.g. as measured relative to the base shape). As shown here, the lower point of the echelette can correspond to the location of the base shape. In this example, the step height of the center or first echelette 802 is ($h_1$), the step height of the second peripheral echelette 810 is ($h_2$), the step height of the third peripheral echelette 820 is ($h_3$), the step height of the fourth peripheral echelette 830 is ($h_4$), and the step height of the fifth peripheral echelette 840 is ($h_5$). FIG. 8-1 shows a related diffractive profile embodiment, here depicted relative to a convex posterior base.

In some instances, a diffractive profile includes 9 rings on a 5 mm diameter optic surface. The diffractive profile can include two central rings each having a step height that is larger than the step heights of the other seven peripheral rings. The diffractive profile can provide a monofocal diffractive surface that at least partially corrects or compensates for natural chromatic aberration produced by the patient's eye. The aspheric anterior surface of the ophthalmic lens can operate to correct or treat spherical aberration of the eye. In some instances, lens system and methods embodiments of the present invention may incorporate features of lenses and treatments disclosed in U.S. Pat. No. 6,830,332, which discusses lenses having both aspheric anterior surfaces and diffractive posterior surfaces. In some cases, lens designs may also incorporate diffractive surfaces, for example which direct 63% of the total light to the far focus and 21% to a near or intermediate focus. In some instances, a diffractive surface can provide an add power of 1.75 D, with a central 2.2 mm diameter zone that directs 41% of the total light to far focus and 41% to intermediate focus, surrounded by an outer zone which directs 63% of the total light to the far focus and 21% to the intermediate focus. Exemplary diffractive surfaces can be pupil independent, have an add power of 1.75 Diopters, and provide a central zone light distribution between the far focus and the intermediate focus of 50%:50% and a peripheral zone light distribution between the far focus and the intermediate focus of 75%:25%. In optical terms, the diffractive profile provides a plurality of foci.

Figure 8A:
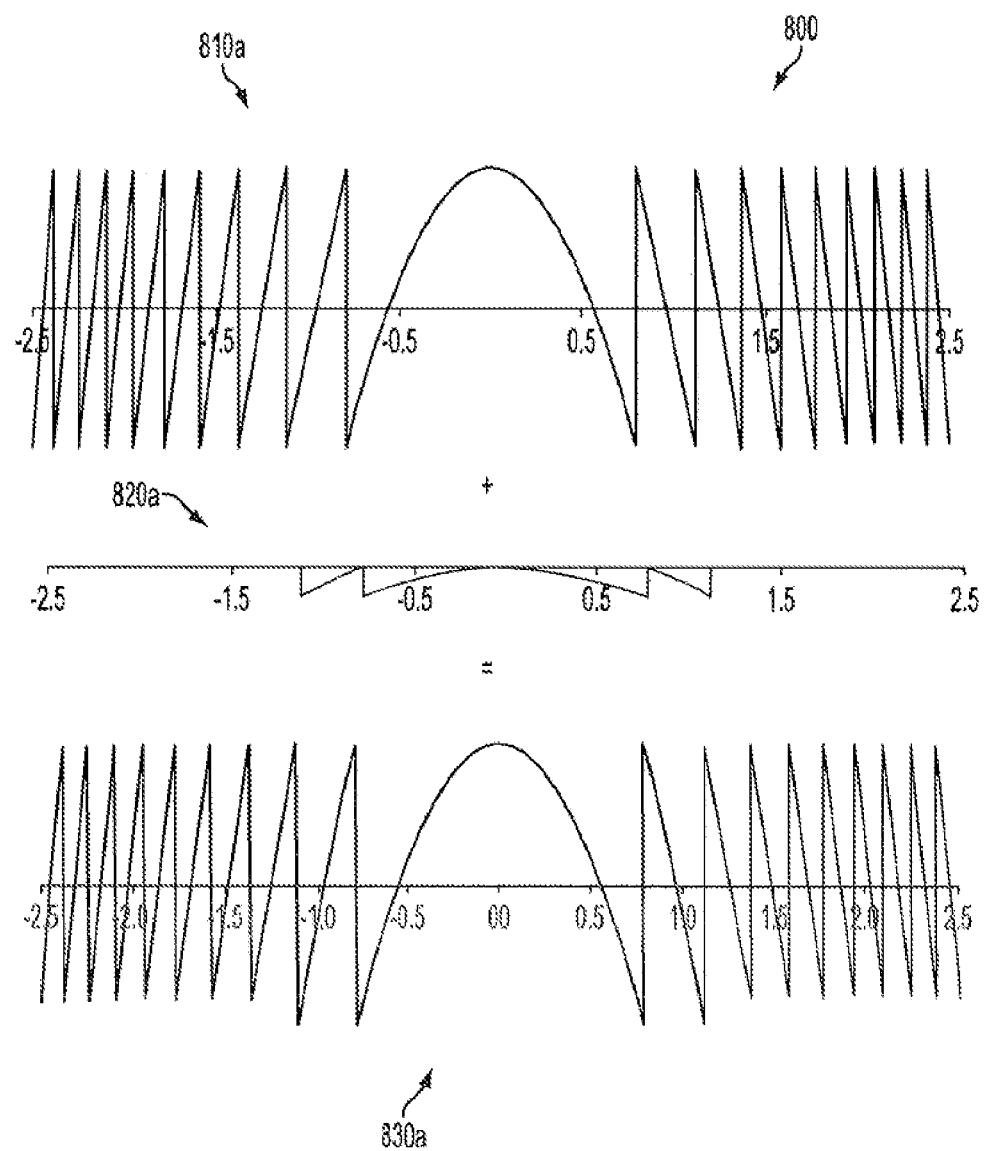
Figure 8B:
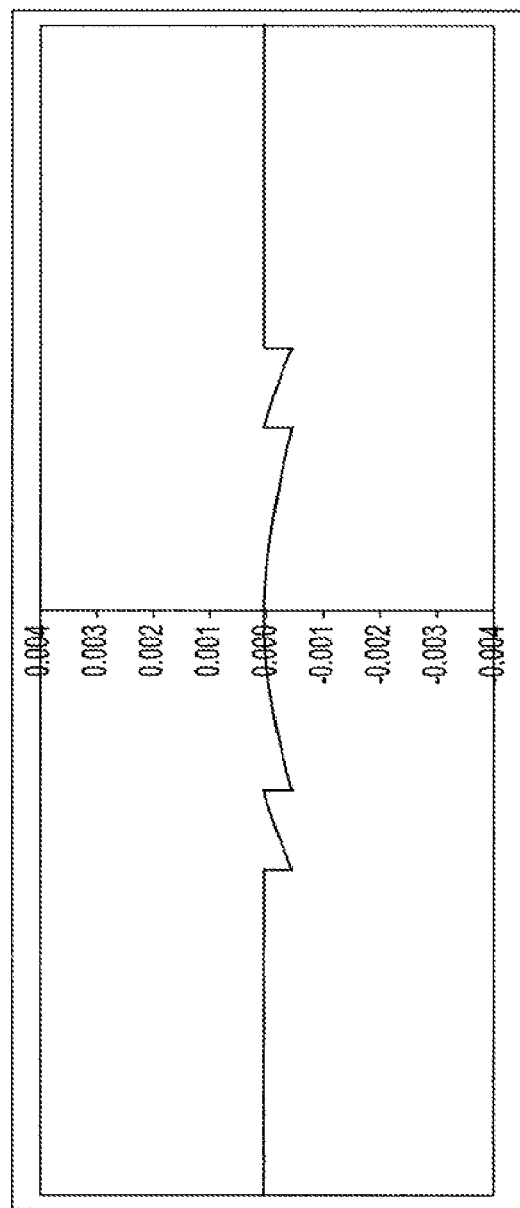
Figure 8C:
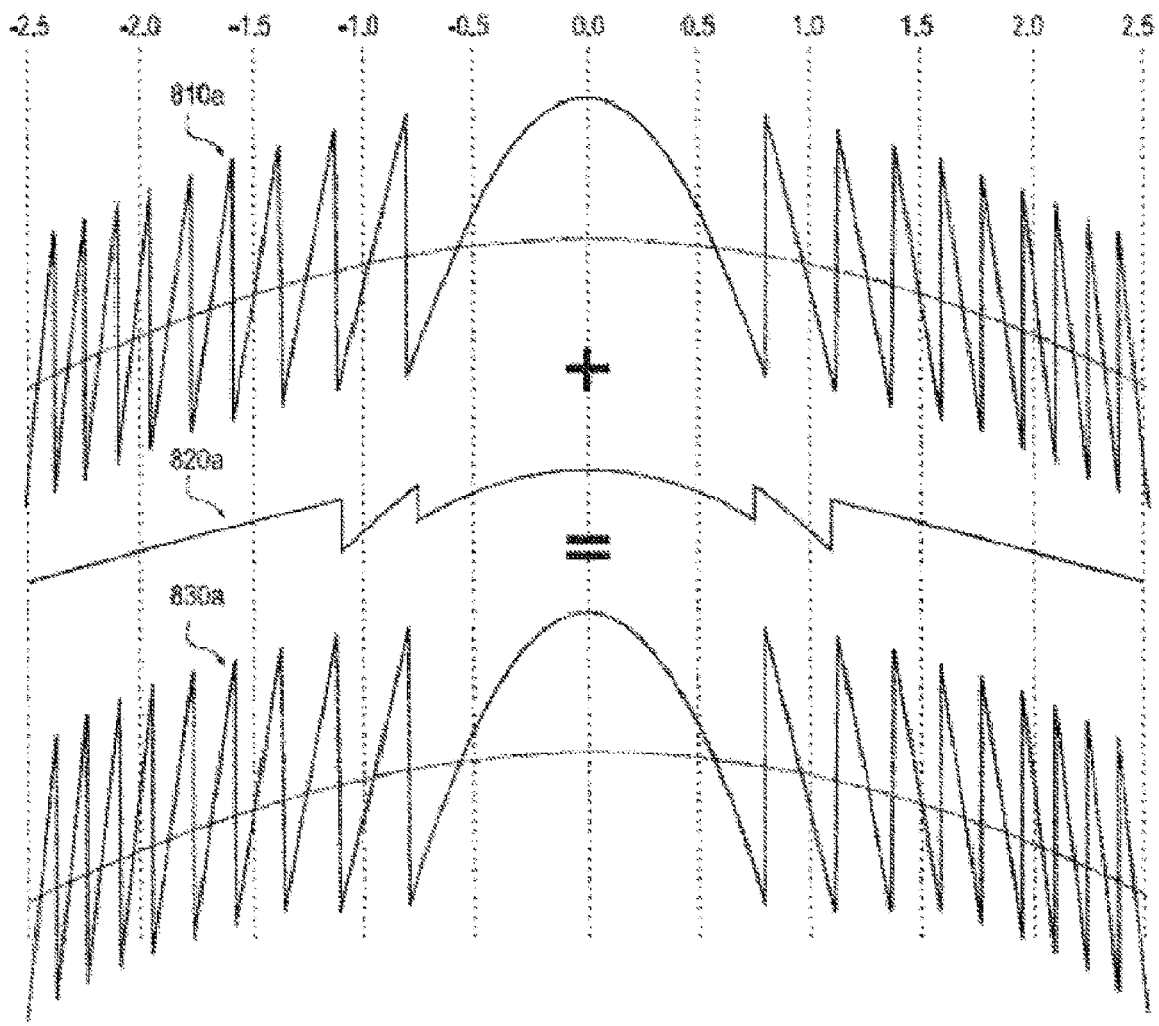
Figure 8D:
Figure 8E:
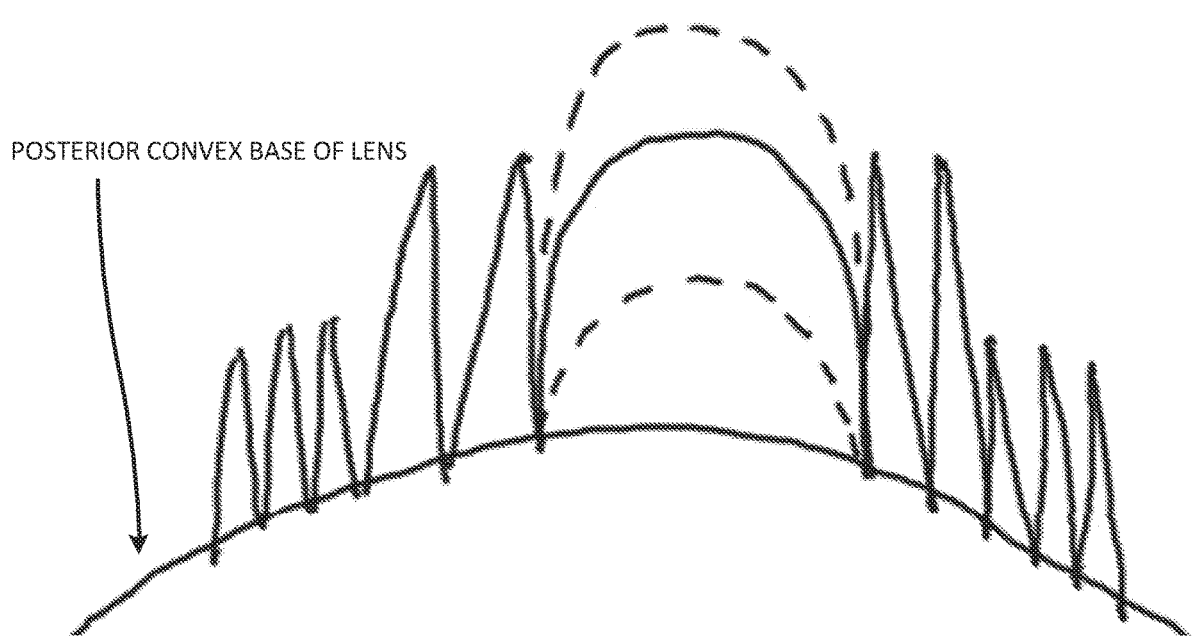

In some embodiments, the diffractive profile 800 can be represented as the incorporation of two diffractive echelettes 802 and 810 on top of a base ophthalmic lens configuration. FIG. 8A provides a schematic illustration of such a construction. Here, the upper graph 810a corresponds to a first or base diffractive profile having an equal step height across the entire optical surface, and the middle graph 820a corresponds to a second diffractive profile having two central echelettes or rings (which may also have equal step heights). A similar second diffractive profile is depicted in FIG. 8B (the base is shown having a convex shape, and the central echelettes are below the base radius). The lower graph 830a corresponds to a third diffractive profile based on the combination of the first and second diffractive profiles. Relatedly, FIG. 8C provides a schematic illustration of a final diffractive profile that combines two diffractive profiles. FIGS. 8D and 8E also show aspects of exemplary diffractive profiles, according to embodiments of the present invention. In FIG. 8D, the echelettes of the central zone may extend into or anterior to the convex base. The first (center) echelette and the second echelette can both extend similar or equal distances from the posterior base. Or, the first echelette can extend posterior to the second echelette. Or, the second echelette can extend posterior to the first echelette. As seen in FIG. 8E, the first echelette may extend posterior to the posterior base at various distances relative to the second or other peripheral echelettes. It is also envisioned that some or all of the echelettes will extend into (or anterior to) the convex base.

A base ophthalmic lens configuration may include a diffractive surface profile such as that described in U.S. Pat.

No. 6,830,332, incorporated herein by reference. For example, the base lens configuration may include an achromatic design having a profile height that is equal to one wavelength, as discussed at column 4, lines 42-43 of the '332 patent. Embodiments of the present invention encompass designs that include extended depth of focus (EDOF) step heights that are placed on top of such an achromatic design.

In some instances, a base ophthalmic lens configuration may incorporate a pupil independent diffractive profile over the entire optic. Hence, the lens can continue to provide excellent intermediate vision properties as the pupil widens in low light conditions. This pupil independent diffractive profile may have the same ring structure (add power) as the two echelettes. As a result, the two echelettes show up as two central echelettes having higher profile height (step height) on an otherwise constant-height diffractive profile.

In some instances, each echelette or ring has a step height or profile height that is larger than one wavelength. For example, a wavelength can be 550 nm, as that described in U.S. Pat. No. 6,830,332, incorporated herein by reference. Accordingly, the diffractive profile can operate to distribute incident or incoming light substantially or predominately to the first and second diffractive orders, for example to far focus 730 and intermediate focus 740 of FIG. 7, respectively.

Figure 9A:
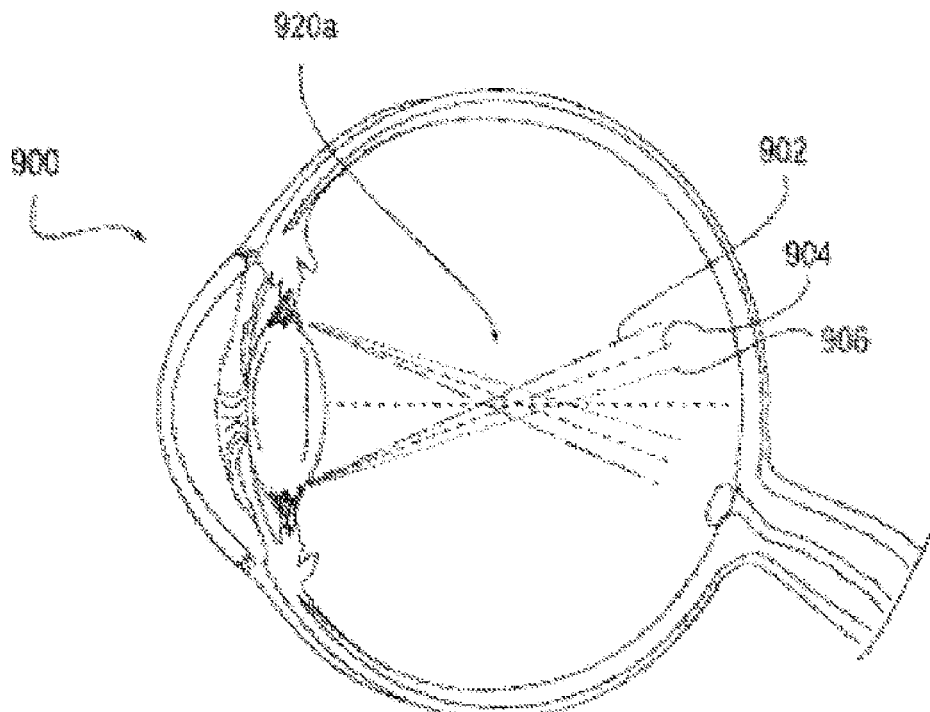
FIGS. 9A and 9B depict aspects of ophthalmic lenses according to embodiments of the present invention.

In some instances, a diffractive profile of an ophthalmic lens produces chromatic aberration in light directed to the first and second diffractive orders that is opposite in sign to the chromatic aberration produced by the natural eye (e.g. a natural phakic or aphakic eye into which an intra-ocular lens is eventually placed). Hence, the diffractive profile can operate to at least partially correct, offset, or otherwise treat the eye's natural chromatic aberration. For example, optical parts of a patient's aphakic eye 900 may introduce chromatic aberration as depicted in FIG. 9A by focusing different wavelengths of light (e.g. blue light 902, green light 904, and red light 906) to different focal positions, respectively. Hence, it can be seen that the patient's own eye can produce chromatic aberration, where the chromatic aberration produced by the eye causes different wavelengths of light to have differing focal lengths.

Figure 9B:
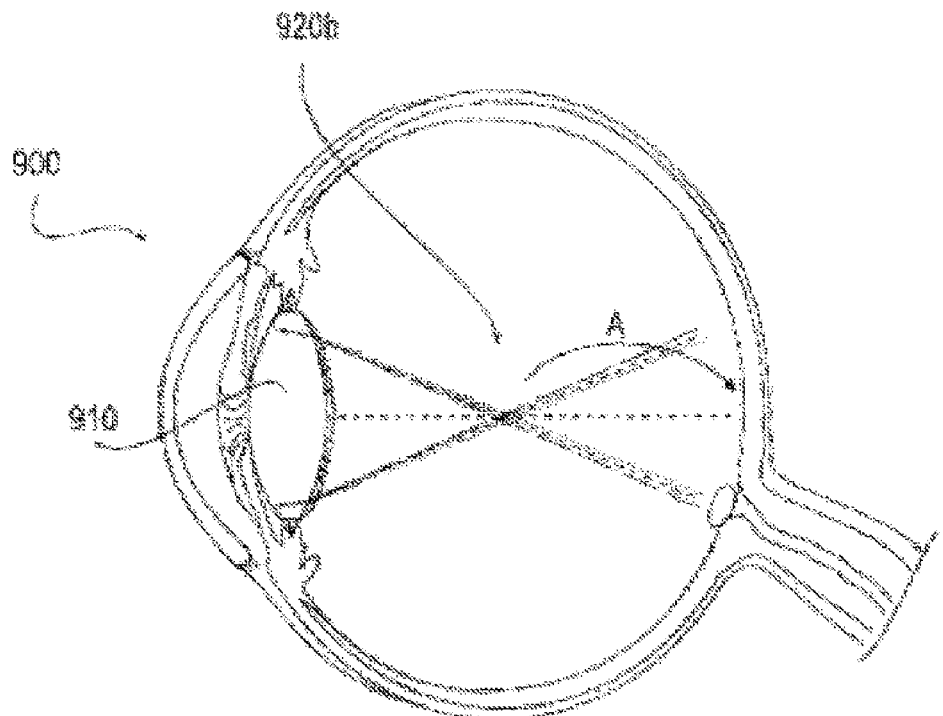

As depicted here, FIGS. 9A and 9B are schematic drawings, and the focal points or regions (e.g. 920a, 920b respectively) are shown at the center of the eye for purposes of clarity. Normally, the focal point or area is at, or close to, the retina at the posterior of the eye.

By introducing an ophthalmic lens 910 as depicted in FIG. 9B, it is possible to counteract the natural chromatic aberration of the eye, and as a result bring multiple wavelengths of the visible spectrum toward a single focal point (e.g. 920b). Hence, the pseudophakic eye of FIG. 9B provides an improvement in the quality of images seen by the patient. The light at different wavelengths is now aligned, or more aligned, as compared with FIG. 9A. In this way, the ophthalmic lens 910 operates to compensate for chromatic aberration produced by the eye (e.g. ocular chromatic aberration). It is understood that ophthalmic lenses as disclosed herein can correct or treat chromatic aberration at one or more diffractive orders or foci.

In some instances, light rays at the periphery of the patient eye (e.g. cornea) may be over-refracted, thus producing a region of defocused light that decreases image quality, for example due to spherical aberration. In some cases, the cornea, optionally in combination with other optical parts of the eye, can produce spherical aberration. Hence, spherical aberration may in various instances be referred to as corneal spherical aberration or ocular spherical aberration. An aspheric surface of the ophthalmic lens can compensate for such spherical aberration, by reducing the amount by which the peripheral light rays are refracted. For example, as shown in FIG. 9B, an aspheric optical surface of the lens 910 can compensate for a region of defocused light and thereby create a properly or improved focused point of light toward the retina or posterior of the eye, as indicated by arrow A. As shown here, in addition to compensating for ocular chromatic aberration, the ophthalmic lens also operates to compensate for ocular spherical aberration, and delivers more accurately focused light toward the posterior of the eye.

According to some embodiments, an ophthalmic lens 900 can operate to treat or correct chromatic aberration over a range of foci, or over an extended depth of focus. For example, an ophthalmic lens can provide a partial correction or treatment of chromatic aberration in the far focus (e.g. focus 730 of FIG. 7), and a substantially larger or full correction or treatment of chromatic aberration in the intermediate focus (e.g. focus 740 of FIG. 7). Such treatment of chromatic aberration can be achieved by using a specific diffractive power.

For example, let the $n^{th}$ diffractive order be associated with the far focus of the ophthalmic lens, and the $j^{th}$ diffractive order be associated with the intermediate focus (focus range) of the ophthalmic lens. The difference between the orders is j−n. For an extended depth of focus lens, the difference in lens power (e.g. in unit of Diopters) between the intermediate and the far vision denotes the range of extended depth of focus.

Relatedly, let the chromatic aberration of the ophthalmic lens in the $n^{th}$ diffractive order, or far focus, be characterized as $LCA_f$ with the following equation:

$$LCA_f = LCA_r + n*LCA_d$$

Here, $LCA_r$ refers to the longitudinal chromatic aberration of the refractive base lens and $LCA_d$ refers to the longitudinal chromatic aberration of the diffractive profile. It is noted that the above equation includes a "+" sign, however the value of $LCA_d$ in the equation is negative.

Similarly, the chromatic aberration of the diffractive focus for the $j^{th}$ diffractive order, or intermediate vision, can be characterized as LCA, with the following equation:

$$LCA_i = LCA_r + j*LCA_d.$$

For designs having correction of ocular chromatic aberration, $LCA_f$ and $LCA_i$ should have negative values.

Let the chromatic aberration of the aphakic eye be $LCA_{ae}$. Correction of the ocular chromatic aberration, without overcorrection is obtained if:

$$-LCA_f \leq LCA_{ae}$$

and $$-LCA_i \leq LCA_{ae}$$

Or:

$$n \leq (LCA_{ae} + LCA_r)/(-LCA_d)$$

$$j \leq (LCA_{ae} + LCA_r)/(-LCA_d)$$

For example, with a diffractive profile having positive diffractive orders, $LCA_{ae}=2$ D, $LCA_r=1.5$ D and $LCA_d=-1.75$ D. Full chromatic aberration is obtained in the intermediate vision for the diffraction order of j=(2+1.5)/1.75=2. In such a case, the first diffractive order leaves the eye with a LCA of (2+1.5−1*1.75)=1.75 D, and giving a reduction of LCA by 1.75 D of the pseudophakic eye (e.g. artificial lens implanted), and 0.25 D reduction of the aphakic eye (e.g. natural lens removed).

Table 4 provides step height, diameter, optical path difference (OPD in wavelength λ) and light distribution values for an exemplary diffractive profile, according to embodiments of the present invention.

TABLE 4

| Echelette | Step Height | Outer Diameter | OPD | Light Distribution ($1^{ST}:2^{ND}$) |
|---|---|---|---|---|
| 1st/Center | $h_1$ = 0.0062 mm | 1.60 mm | 1.5 λ | two combined echelettes |
| 2nd | $h_2$ = 0.0062 mm | 2.20 mm | 1.5 λ | provide 41% to $1^{st}$ order and 41% to $2^{nd}$ order (for a distribution between $1^{st}$ and $2^{nd}$ of 50:50) |
| 3rd | $h_3$ = 0.0062 mm | 2.75 mm | 1.5 λ | seven combined echelettes |
| 4th | $h_4$ = 0.0056 mm | 3.17 mm | 1.366 λ | provide 63% to first order |
| 5th | $h_5$ = 0.0056 mm | 3.55 mm | 1.366 λ | and 21% to $2^{nd}$ order (for |
| 6th | $h_6$ = 0.0056 mm | 3.88 mm | 1.366 λ | a distribution between $1^{st}$ |
| 7th | $h_7$ = 0.0056 mm | 4.20 mm | 1.366 λ | and $2^{nd}$ of 75:25) |
| 8th | $h_8$ = 0.0056 mm | 4.48 mm | 1.366 λ | |
| 9th | $h_9$ = 0.0056 mm | 4.76 mm | 1.366 λ | |

According to some embodiments, the step heights are configured so that the lens generally functions using the $1^{st}$ and $2^{nd}$ diffractive orders. The specific step heights used may depend on the refractive index of the material present in the lens, and/or the wavelength considered. Typically, each step height creates a difference in optical path length. Hence, assuming that the refractive index of the aqueous of the eye is 1.336, and considering an ophthalmic lens material having a refractive index 1.47, an approximately four micron step height introduces an optical path difference of one wavelength. In some instances, embodiments of the present invention encompass lens designs having step height values greater than four microns. In some instances, embodiments of the present invention encompass lens designs having step height values within a range between four and 8 microns. In some instances, embodiments of the present invention encompass lens designs having echelette step heights that introduce optical path difference values that are greater than one.

As indicated in Table 4, an exemplary ophthalmic lens can include a central zone having two echelettes that operate to direct light between far and intermediate foci at a 50:50 relative ratio for an EDOF effect at small and medium pupil sizes. The further peripheral echelettes operate in combination to direct light between far and intermediate foci at a 75:25 relative ratio, which can maintain an EDOF effect for larger pupil sizes.

Figure 10A:
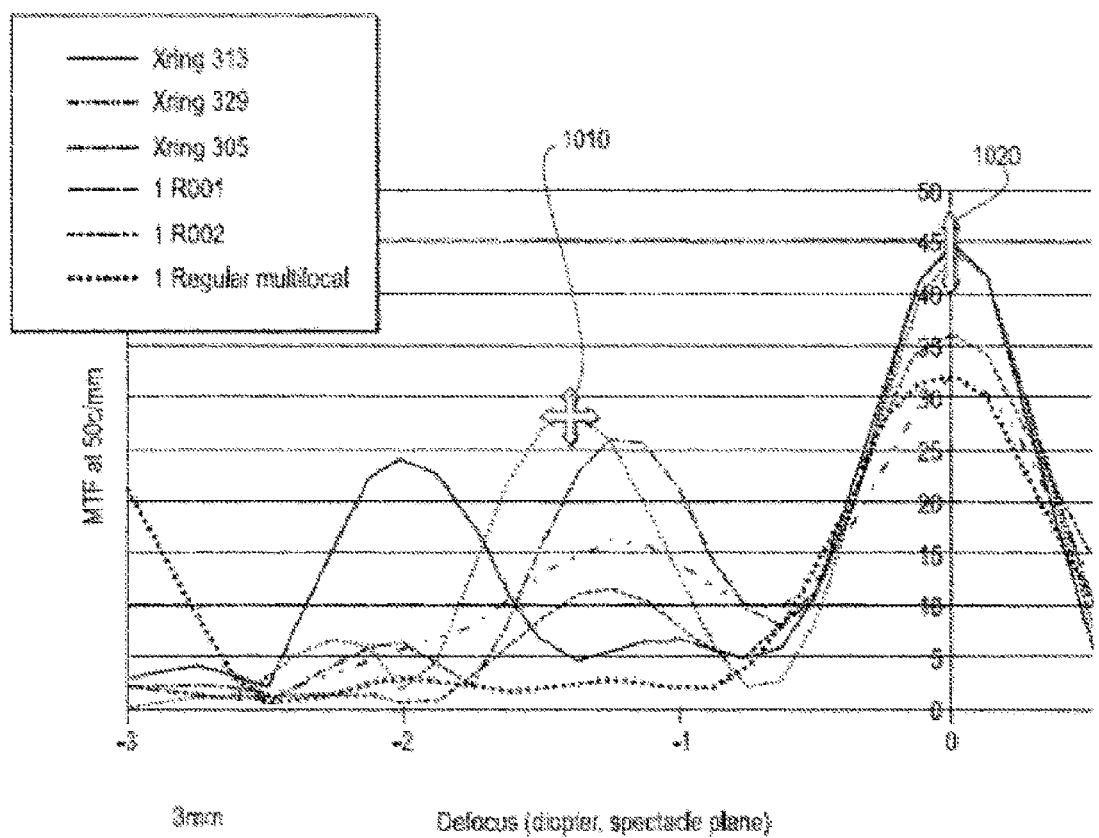
FIGS. 10A and 10B depict aspects of ophthalmic lenses according to embodiments of the present invention.
Figure 10B:
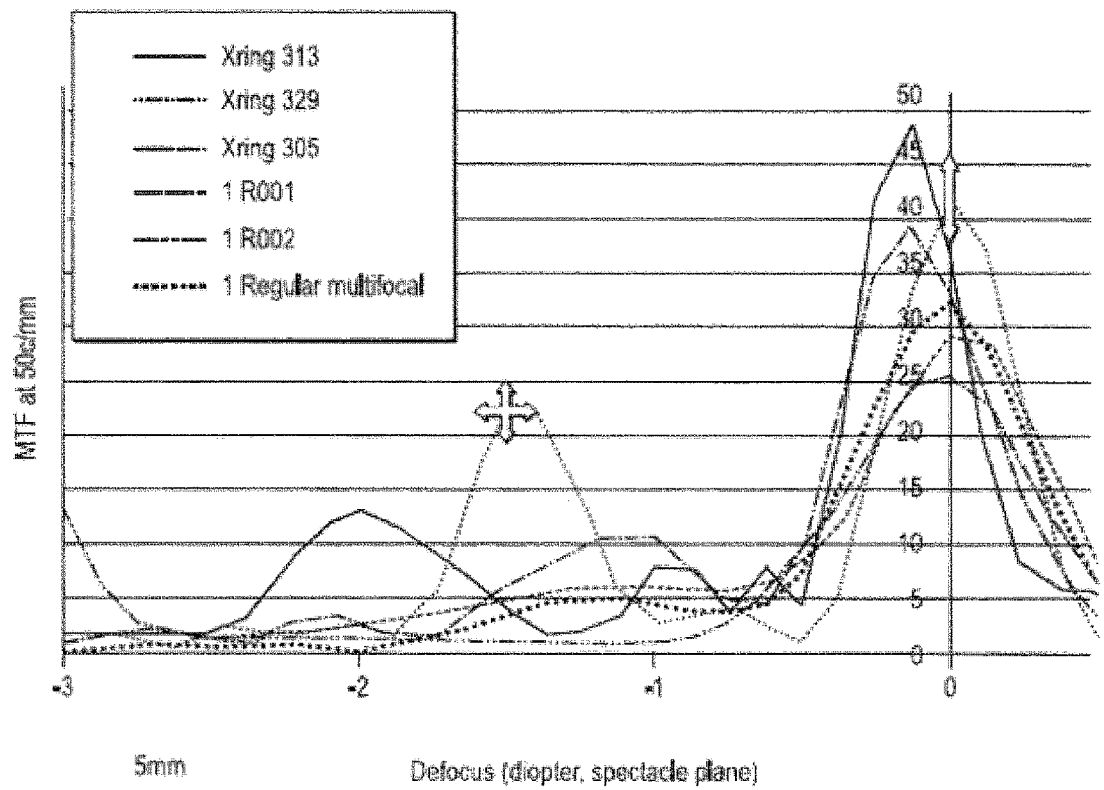

FIGS. 10A and 10B show modulation transfer function (MTF) curves for ophthalmic lens configurations according to embodiments of the present invention (i.e. Xring 313, Xring 329, and Xring 305), as compared with other single ring intraocular lens designs (i.e. 1R001 and 1R002) and standard multifocal intraocular lens designs. Exemplary single ring designs are described in previously incorporated U.S. Patent Application No. 61/288,255 filed Dec. 18, 2009. Hence, the through focus performance, in white light, of the various designs can be compared. These graphs are based on measurements of prototype lenses, placed in an eye model that is similar to a modified ISO model, as described in Norrby et al., "Model eyes for evaluation of intraocular lenses" Appl. Opt. 46 (26): 6595-605 (2007), the content of which is incorporated herein by reference. FIG. 10A illustrates the through focus performance of the lenses at a pupil diameter of 3 mm (e.g. medium pupil size), and FIG. 10B illustrates the through focus performance of the lenses at a pupil diameter of 5 mm (e.g. large pupil size). The large pupil size represents a pupil size under low light conditions. The vertical axis denotes the modulation (MTF) at 50 cycles per millimeter. The horizontal axis denotes the defocus in the spectacle plane. Defocus in the spectacle plane can be translated into viewing distance, roughly by the equation (viewing distance in centimeters)=100/(defocus in the spectacle plane). For instance, a defocus of 1.33 Diopters in the spectacle plane corresponds with 100/1.33=75 centimeters viewing distance.

As shown here, the peak 1010 at intermediate focus (about 1.3 Diopters in the spectacle plane) can change in the horizontal position, by changing the diffractive add power of the ophthalmic lens. For example, adjusting the echelette diameters of the central and outer diffractive zones (e.g. as shown in FIG. 7) can operate to change the diffractive add power. The peak 1010 at the intermediate focus can also change in the vertical position, by changing the light distribution of the ophthalmic lens. For example, adjusting the step heights of the central and outer diffractive zones (e.g. as shown in FIG. 7) can operate to change the light distribution percentage at the intermediate focus.

Relatedly, the peak 1020 at far focus (0 Diopters) can change in the vertical position, by changing the light distribution of the ophthalmic lens. For example, adjusting the step heights of the central and outer diffractive zones (e.g. as shown in FIG. 7) can operate to change the light distribution percentage at the far focus. That is, directing a higher percentage of light to the far focus will increase the height of peak 1020 upward, and directing a lower percentage of light to the far focus will decrease the height of peak 1020.

Hence, according to some embodiments, variations in lens step heights can operate to change light distribution properties of the lens, and with that, the vertical positions of 1010 and 1020. Further, variations in ring diameters can operate to change the add power properties of the lens, and with that, the horizontal positions of 1010.

The result of these variations are shown in FIGS. 10A and 10B, in which three lens design embodiments according to the present invention (annotated as "Xring") having different add powers and light distributions are shown. The lens corresponding to the line labeled with "Xring 313" has 2.5 Diopter add power, the lens corresponding to the line labeled with "Xring 329 has 1.75 Diopter add power, and the lens corresponding to the line labeled with "Xring 305 has 1.5 Diopter add power. As depicted here, the 1.75 Diopter design of the Xring 329 lens has an intermediate peak at about 1.3 Diopters, as the horizontal axis denotes defocus in the spectacle plane. As a general rule, defocus in the spectacle plane is about ¾ of defocus in the intraocular lens plane (e.g. ¾*1.75≈1.3). In this sense, the intraocular lens add power of 1.75 Diopters can be distinguished from the spectacle plane defocus of 1.3 D.

Additional details regarding the use of modulation transfer function (MTF) to evaluate the performance of a visual system (e.g. ophthalmic lens and/or other optical parts of the eye) are described in U.S. Patent Publication No. 2009/0210054, which is incorporated herein by reference.

Figure 11A:
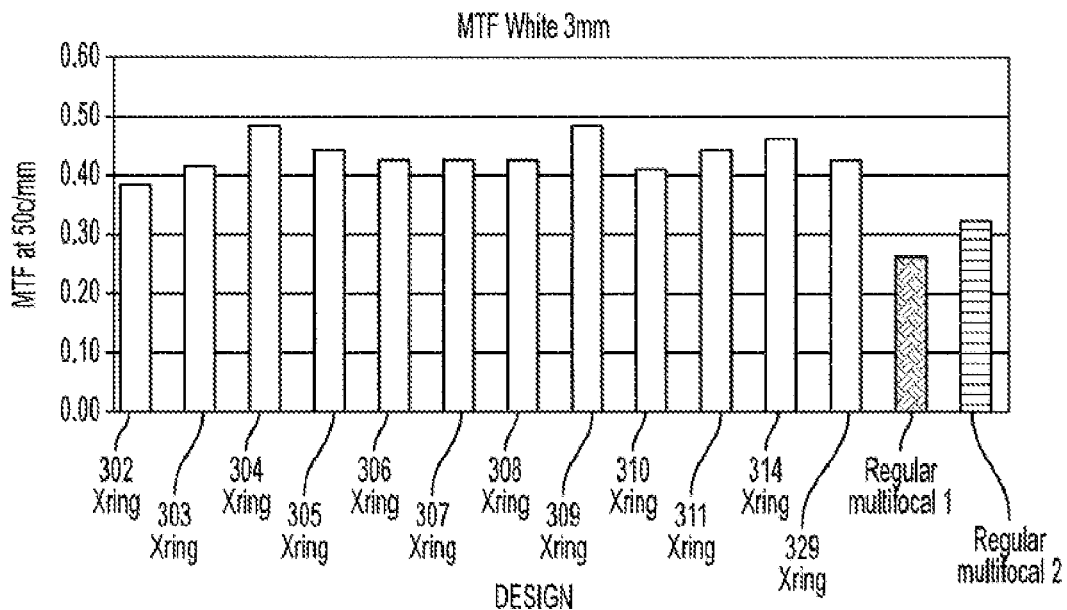
FIGS. 11A and 11B depict aspects of ophthalmic lenses according to embodiments of the present invention.
Figure 11B:
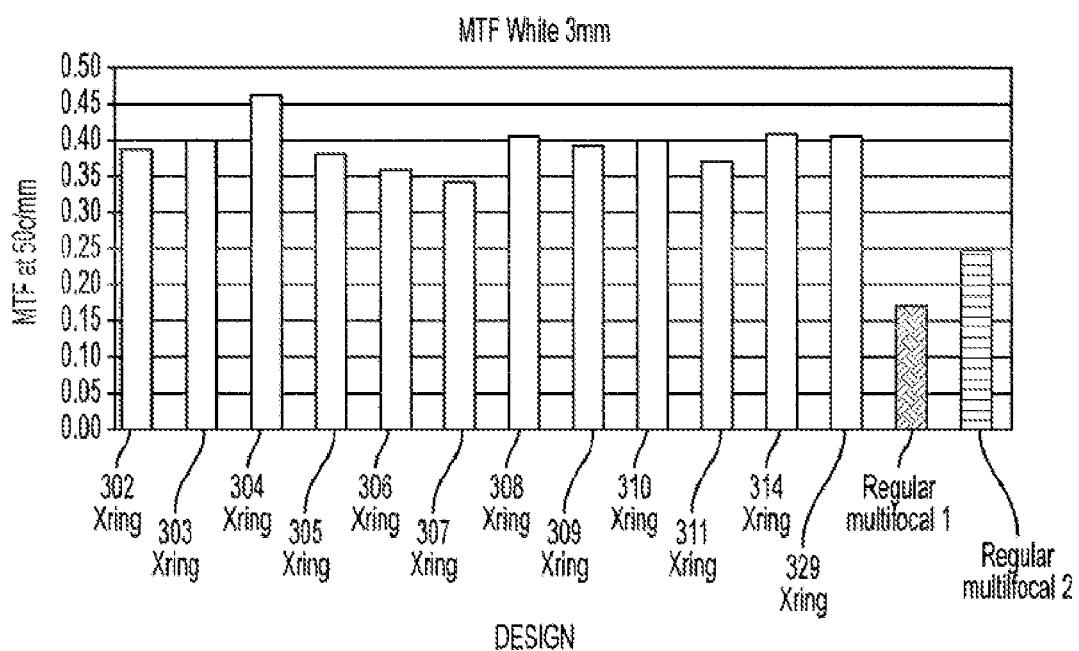

FIGS. 11A and 11B show modulation transfer function (MTF) data for various ophthalmic lens configurations according to embodiments of the present invention (e.g. Xring designs 302 to 311, 314, and 329), as compared with two regular multifocal intraocular lens designs. As shown here, the MTF values at far focus for the ophthalmic lenses according to embodiments of the present invention (e.g. Xring designs) are better than the MTF values at far focus for these multifocal intraocular lens designs. For a 3 mm pupil, the MTF of embodiments of the present invention is 18% to 83% higher than that of current regular multifocal lenses. For a 5 mm pupil, the MTF of embodiments of the present invention is 39% to 173% higher than that of current regular multifocal lenses.

FIG. 12A provides an illustration of US Air Force images by defocus for a 3-mm pupil diameter, for various lens design configurations. Defocus values are provided in Diopters, in the spectacle plane. As shown here, the Xring designs (307, 311, 314, and 329) provide better results than a multifocal intraocular lens design, a monofocal lens design, and two single ring designs (1R001 and 1R002). The four different Xring designs depicted here each have different add power and light distributions. Xring 307 has an add power of 1.5 Diopters, Xring 311 has an add power of 2.0 Diopters, Xring 314 has an add power of 2.5 Diopters, and Xring 329 has an add power of 1.75 Diopters.

Model eye data demonstrating that a single ring ophthalmic lens design can provide an extended depth of field effect is provide in previously incorporated U.S. Patent Application No. 61/288,255 filed Dec. 18, 2009. FIG. 12A provides defocus images of the U.S. Air Force target, corresponding to two intraocular lens designs according U.S. 61/288,255 (e.g. 1R001 AND 1R002) and a regular monofocal aspheric intraocular lens design ("Monofocal" in FIG. 12), in a modified ISO eye model as described in the previously incorporated Norrby et al., "Model eyes for evaluation of intraocular lenses" Appl. Opt. 46 (26): 6595-605 (2007). As depicted here, under defocus, the images corresponding to the 1R001 and 1R002 IOL designs are less blurred when the eye is defocused, as compared to those of the monofocal lens design. Up to at least −2.00 Diopters of defocus, some of the horizontal and vertical bars can still be distinguished with the 1R001 and 1R002 designs. In contrast, for the regular monofocal IOL design, the horizontal and vertical bars can be distinguished only up to less than −1.00 Diopters. These pictures were taken with white light. It may be helpful to evaluate or refer to clinical results in terms of the size of the EDOF effect. The Xring designs are intended to provide an enhanced EDOF effect. FIG. 12B show the area under the MTF curve, up to 25 c/mm, when an exemplary lens of the current invention is measured in this same modified ISO eye model. The exemplary lens in FIG. 12B has a base lens configuration with an achromatic design on the posterior side of the lens. The achromatic design has a profile height that is equal to one wavelength. The EDOF design is placed on top of the achromatic design. The EDOF design of FIG. 12B is seen in Table 4. Finally, an aspheric shape on the anterior side of the lens reduces spherical aberration. The combination results in the MTF curve seen in FIG. 12B. FIG. 12B also shows the measurement results of a regular multifocal lens. The graph illustrates that, as opposed to a regular multifocal lens, which has two distinct peaks with a valley in between representing two distinct focal points, the current design has one broad peak over an extended range of vision representing a gradual change of image quality over the extended range. This illustrates that IOLs according to the present invention behave in a well-defined different manner compared to regular multifocal lenses.

The images of FIG. 12 show only part of the range of the exemplary lens according to embodiments of the present invention. In some cases, a multifocal lens has a second sharp image at about −3 Diopters defocus. In between the best focus (0 Diopter) and the second focus at −3 Diopters, the multifocal lens may show highly blurred images. However, it should be realized that for a multifocal lens, the visual function at intermediate distances is still at a functional level, with a visual acuity that is often better than 20/40. This observation can be held in mind when evaluating the images, as well as those representing designs according to embodiments of the present invention.

For example, with the Xring 311 design, the USAF image at −1.50 Diopter defocus is sharper than the image at −1.0 Diopter defocus. The magnitude of this feature is much smaller than what is observed for a multifocal lens. That is, the sharpness difference between −1.50 Diopters and −1.00 Diopter is smaller for the Xring design and larger for the multifocal design. Moreover, the overall sharpness throughout this range is higher for the Xring design as compared to the multifocal design. Therefore, it can be expected that in clinical terms, functional vision at the entire intermediate range is comparable to that at best focus, with a visual acuity of around 20/20. For example, for Xring 311, the intermediate range is estimated to run from 0 to at least −1.75 Diopters.

Various techniques for evaluating the depth of focus in a visual system (e.g. ophthalmic lens and/or other optical parts of the eye) are described in U.S. Patent Publication No. 2009/0210054, which is incorporated herein by reference.

Ophthalmic lens embodiments of the present invention can be configured to compensate for various aberrations produced by a patient eye, such as spherical and chromatic aberration, which may derive from the cornea and/or other optical parts of the patient eye. Hence, methods of designing and/or fabricating such lenses may involve obtaining or using data related to aberrations of the patient eye. Any of a variety of aberrometers, including wavefront measurement systems, may be used to obtain such aberration data. The components of an exemplary wavefront measurement system for measuring the eye and aberrations may comprise elements of a WaveScan® system, available from AMO MANUFACTURING USA, LLC, Milpitas, Cali. One embodiment includes a WaveScan system with a deformable mirror. An alternate embodiment of a wavefront measuring system is described in U.S. Pat. No. 6,271,915, the full disclosure of which is incorporated herein by reference. It is appreciated that any wavefront aberrometer could be employed for use with embodiments of the present invention. Relatedly, embodiments of the present invention encompass the implementation of any of a variety of optical instruments provided by AMO WAVEFRONT SCIENCES, LLC, including the COAS wavefront aberrometer, the ClearWave contact lens aberrometer, the CrystalWave IOL aberrometer, and the like.

In some cases, embodiments of the present invention encompass systems, kits, and computer program products for manufacturing or fabricating ophthalmic lenses as disclosed herein. Ophthalmic lenses can be fabricated using laser ablation processes, and/or may incorporate standard techniques for the manufacture of intraocular lenses, aspects of which are described in U.S. Pat. Nos. 4,856,234, 5,322, 649, and 5,888,122, as well as U.S. Patent Publication No. 2002/0082690. The content of each of these patent publications is incorporated herein by reference. Relatedly, in some instances manufacturing or fabrication processes may include aspects of molding, polishing, measuring of the power, quality control, modeling, and the like.

FIG. 13 depicts aspects of an exemplary method 1300 for generating an ophthalmic lens prescription according to embodiments of the present invention. In some cases, the method may include measuring spherical and/or aberrations of a patient eye. As shown here, the method may include inputting a patient parameter data profile as indicated by step 1330. The data profile may include (a) a patient spherical aberration parameter corresponding to a measured patient spherical aberration 1310 and (b) a patient chromatic aberration parameter corresponding to a measured patient chromatic aberration 1320. Further, the method may include generating the ophthalmic lens prescription for the patient as indicated by step 1340. The ophthalmic lens prescription may be configured to compensate for the measured patient spherical and chromatic aberrations and to provide an extended depth of focus. In some cases, so as to provide the extended depth of focus, the prescription may provide a far focus corresponding to a base power and an intermediate focus corresponding to an add power, where a difference between the base power and the add power defines an extended depth of focus for the ophthalmic lens prescription. In some cases, so as to provide the extended depth of focus, the prescription may provide a modulation transfer function value at 50 cycles per millimeter of at least 10, for an intermediate focus, at 3 mm and 5 mm pupil diameters.

FIG. 14 depicts aspects of an exemplary method 1400 for fabricating an ophthalmic lens according to embodiments of the present invention. As shown here, the method includes inputting an ophthalmic lens prescription for a patient as indicated by step 1410, and fabricating the ophthalmic lens based on the prescription as indicated by step 1420. The ophthalmic lens prescription may be configured to compensate for a measured patient spherical aberration, compensate for a measured patient chromatic aberration, and provide an extended depth of focus. Relatedly, the lens may be configured to compensate for patient spherical and chromatic aberrations, and to provide an extended depth of focus. In some cases, so as to provide the extended depth of focus, the lens may provide a far focus corresponding to a base power and an intermediate focus corresponding to an add power, where a difference between the base power and the add power defines an extended depth of focus for the ophthalmic lens. In some cases, so as to provide the extended depth of focus, the lens may provide a modulation transfer function value at 50 cycles per millimeter of at least 10, for an intermediate focus, at 3 mm and 5 mm pupil diameters.

FIG. 15 illustrates an exemplary system 1500 for generating an ophthalmic lens prescription for an eye of a patient, according to embodiments of the present invention. The system includes an input 1510 that accepts a patient parameter data profile specific for the patient eye. The patient parameter data profile may include a patient spherical aberration parameter corresponding to a measured spherical aberration of the patient eye, and a patient chromatic aberration parameter corresponding to a measured chromatic aberration of the patient eye. The system also includes a module 1520 having a tangible medium embodying machine-readable code that generates the ophthalmic lens prescription for the eye. As shown here, the prescription is for a lens that compensates for the measured spherical and chromatic aberrations and that provides an extended depth of focus. In some cases, so as to provide the extended depth of focus, the lens may provide a far focus corresponding to a base power and an intermediate focus corresponding to an add power, where a difference between the base power and the add power defines an extended depth of focus for the ophthalmic lens. In some cases, so as to provide the extended depth of focus, the lens may provide a modulation transfer function value at 50 cycles per millimeter of at least 10, for an intermediate focus, at 3 mm and 5 mm pupil diameters.

FIG. 16 depicts an exemplary system 1600 for fabricating an ophthalmic lens for an eye of a patient. The system includes an input 1610 that accepts an ophthalmic lens prescription for the patient eye. The prescription is for a lens that compensates for measured spherical and chromatic aberrations of the eye of the patient, and that provides an extended depth of focus to the eye of the patient. The system also includes a manufacturing assembly 1620 in connectivity with the input that fabricates an ophthalmic lens according to the lens prescription.

Each of the calculations, operations, methods, and processes described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

The embodiments described above, including accompanying drawings, figures, functions and tables, are for illustrative purposes to explain aspects of the present invention. Hence, while the exemplary embodiments have been described in some detail, by way of example and for clarity of understanding, those of skill in the art will recognize that a variety of modification, adaptations, and changes may be employed. Hence, the scope of the claims should not be limited to the description of the preferred versions contained herein.

What is claimed is:

1. An ophthalmic lens, comprising:
 a first surface and a second surface, the first and second surfaces disposed about an optical axis;
 an aspherical refractive profile imposed on the first surface;

a diffractive profile imposed on the first or second surface and including a central zone and a peripheral zone, the central zone configured to distribute a first non-zero percentage of light toward a far focus and a second non-zero percentage of light toward an intermediate focus, wherein the first non-zero percentage of light is between 41% and 63% and the second non-zero percentage of light is between 21% and 41% the peripheral zone configured to distribute a third non-zero percentage of light toward the far focus and a fourth non-zero percentage of light toward the intermediate focus, wherein the third non-zero percentage of light is greater than the first non-zero percentage of light.

2. The ophthalmic lens of claim 1, wherein a ratio of the third non-zero percentage of light to the fourth non-zero percentage of light is greater than a ratio of the first non-zero percentage of light to the second non-zero percentage of light.

3. The ophthalmic lens of claim 2, wherein the ratio of the third non-zero percentage of light to the fourth non-zero percentage of light is 3:1.

4. The ophthalmic lens of claim 2, wherein the ratio of the first non-zero percentage of light to the second non-zero percentage of light is 1:1.

5. The ophthalmic lens of claim 1, wherein the third non-zero percentage of light is between 41% and 100% and the fourth non-zero percentage of light is between greater than 0% and 41%.

6. The ophthalmic lens of claim 1, wherein the ophthalmic lens is an intraocular lens and the intermediate focus corresponds to an intraocular add power within a range between 1 Diopter and 2.5 Diopters.

7. The ophthalmic lens of claim 1, wherein the central zone includes at least two echelettes.

8. The ophthalmic lens of claim 1, wherein the diffractive profile is configured to compensate for ocular chromatic aberration, and the aspherical refractive profile is configured to compensate for ocular spherical aberration, and the aspherical refractive profile and the diffractive profile when combined provide an extended depth of focus for the ophthalmic lens.

9. A method for manufacturing an ophthalmic lens for a patient, the method comprising:
inputting an ophthalmic lens prescription for the patient; and
manufacturing the ophthalmic lens based on the ophthalmic lens prescription,
wherein the ophthalmic lens includes a first lens surface having an aspherical profile and a diffractive profile including a central zone and a peripheral zone on the first lens surface or a second lens surface, the central zone configured to distribute a first non-zero percentage of light toward a far focus and a second non-zero percentage of light toward an intermediate focus, wherein the first non-zero percentage of light is between 41% and 63% and the second non-zero percentage of light is between 21% and 41%, and the peripheral zone configured to distribute a third non-zero percentage of light toward the far focus and a fourth non-zero percentage of light toward the intermediate focus, wherein the third non-zero percentage of light is greater than the first non-zero percentage of light.

10. The method of claim 9, wherein the ophthalmic lens is configured to provide a partial correction of a patient chromatic aberration in the far focus and a larger correction of the patient chromatic aberration in the intermediate focus.

11. The method of claim 10, wherein the ophthalmic lens is configured to compensate for a patient spherical aberration.

12. The method of claim 9, wherein a ratio of the third non-zero percentage of light to the fourth non-zero percentage of light is greater than a ratio of the first non-zero percentage of light to the second non-zero percentage of light.

13. The method of claim 9, wherein the third non-zero percentage of light is between 41% and 100% and the fourth non-zero percentage of light is between greater than 0% and 41%.

14. An ophthalmic lens, comprising:
a first surface and a second surface, the first and second surfaces disposed about an optical axis;
an aspherical refractive profile imposed on the first surface;
a diffractive profile imposed on the first or second surface and including a central zone and a peripheral zone, the central zone configured to distribute a first non-zero percentage of light toward a far focus and a second non-zero percentage of light toward an intermediate focus, and the peripheral zone configured to distribute a third non-zero percentage of light toward the far focus and a fourth non-zero percentage of light toward the intermediate focus, wherein the third non-zero percentage of light is between 41% and 100% and the fourth non-zero percentage of light is between greater than 0% and 41%, and wherein the third non-zero percentage of light is greater than the first non-zero percentage of light.

15. The ophthalmic lens of claim 14, wherein a ratio of the third non-zero percentage of light to the fourth non-zero percentage of light is greater than a ratio of the first non-zero percentage of light to the second non-zero percentage of light.

16. The ophthalmic lens of claim 15, wherein the ratio of the third non-zero percentage of light to the fourth non-zero percentage of light is 3:1.

17. The ophthalmic lens of claim 15, wherein the ratio of the first non-zero percentage of light to the second non-zero percentage of light is 1:1.

18. The ophthalmic lens of claim 14, wherein the first non-zero percentage of light is between 41% and 63% and the second non-zero percentage of light is between 21% and 41%.

19. The ophthalmic lens of claim 14, wherein the ophthalmic lens is an intraocular lens and the intermediate focus corresponds to an intraocular add power within a range between 1 Diopter and 2.5 Diopters.

20. The ophthalmic lens of claim 14, wherein the central zone includes at least two echelettes.

21. A method for manufacturing an ophthalmic lens for a patient, the method comprising:
inputting an ophthalmic lens prescription for the patient; and
manufacturing the ophthalmic lens based on the ophthalmic lens prescription,
wherein the ophthalmic lens includes a first lens surface having an aspherical profile and a diffractive profile including a central zone and a peripheral zone on the first lens surface or a second lens surface, the central zone configured to distribute a first non-zero percentage of light toward a far focus and a second non-zero percentage of light toward an intermediate focus, and the peripheral zone configured to distribute a third non-zero percentage of light toward the far focus and a fourth non-zero percentage of light toward the intermediate focus, wherein the third non-zero percentage of light is between 41% and 100% and the fourth non-zero percentage of light is between greater than 0% and 41%, and wherein the third non-zero percentage of light is greater than the first non-zero percentage of light.

22. The method of claim 21, wherein the ophthalmic lens is configured to provide a partial correction of a patient chromatic aberration in the far focus and a larger correction of the patient chromatic aberration in the intermediate focus.

23. The method of claim 22, wherein the ophthalmic lens is configured to compensate for a patient spherical aberration.

24. The method of claim 21, wherein a ratio of the third non-zero percentage of light to the fourth non-zero percentage of light is greater than a ratio of the first non-zero percentage of light to the second non-zero percentage of light.

25. The method of claim 21, wherein the first non-zero percentage of light is between 41% and 63% and the second non-zero percentage of light is between 21% and 41%.

* * * * *